US010876135B2

(12) United States Patent
Sanchez-Fernandez et al.

(10) Patent No.: US 10,876,135 B2
(45) Date of Patent: Dec. 29, 2020

(54) IN PLANTA RECOMBINATION

(71) Applicant: BASF Plant Science Company GmbH, Ludwigshafen (DE)

(72) Inventors: Rocio Sanchez-Fernandez, Limburgerhof (DE); Christian Biesgen, Quedlinburg (DE); Holger Puchta, Karlsruhe (DE); Nadine Roth, Winden (DE); Friedrich Fauser, Karlsruhe (DE); Michael Pacher, Quedlinburg (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 595 days.

(21) Appl. No.: 14/368,662

(22) PCT Filed: Jan. 4, 2013

(86) PCT No.: PCT/IB2013/050080
§ 371 (c)(1),
(2) Date: Jun. 25, 2014

(87) PCT Pub. No.: WO2013/102875
PCT Pub. Date: Jul. 11, 2013

(65) Prior Publication Data
US 2015/0150160 A1      May 28, 2015

Related U.S. Application Data

(60) Provisional application No. 61/583,651, filed on Jan. 6, 2012.

(30) Foreign Application Priority Data

Jan. 6, 2012   (EP) ..................................... 12150383

(51) Int. Cl.
C12N 15/82      (2006.01)
C12N 15/90      (2006.01)

(52) U.S. Cl.
CPC ....... C12N 15/902 (2013.01); C12N 15/8213 (2013.01)

(58) Field of Classification Search
None
See application file for complete search history.

(56) References Cited

U.S. PATENT DOCUMENTS

2010/0025768 A1   10/2010   Cai et al.

FOREIGN PATENT DOCUMENTS

| CN | 101528924 | 9/2009 |
| WO | WO2005085417 | 9/2005 |
| WO | WO2006032426 | 3/2006 |
| WO | WO2011154927 | 12/2011 |

OTHER PUBLICATIONS

Islan Nature Methods 2012 9: p. 32-34.*
Chevalier et al 2005 (Nucleic Acids and Molecular Biology 16: 33-47).*
Taylor et al 2012 (Nucleic Acids Research 40: p. W110-W116).*
Gisler et al 2002 (The Plant Journal 32: p. 277-284).*
Puchta 1999 (Genetics 152: p. 1173-1181).*
Argast et ai.,"I-Ppol and I-Crei Homing Site Sequence Degeneracy Determined by Random Mutagenesis and Sequential in vitro Enrichment," J. Mol. Biol., vol. 280, (1998), pp. 345-353.
Barzel et al., "Native Homing Endonucleases can Target Conserved Genes in Humans and in Animal Models," Nucleic Acids Research, vol. 39, No. 15, (2011), pp. 6646-6659.
Cai et al., "Targeted Transgene Integration in Plant Cells Using Designed Zinc Finger Nucleases," Plant Mol Biol, vol. 69, (2009), pp. 699-709.
Chen et al., "Directed Evolution of Homing Endonuclease I-Scel with Altered Sequence Specificity," Protein Engineering, Design & Selection, vol. 22, No. 4, (2009), pp. 249-256.
Chevalier and Stoddard, "Homing Endonucleases: Structural and Functional Insight into the Catalysis of Intron/Intein Mobility," Nucleic Acids Research, vol. 29, No. 18, (2001), pp. 3757-3774.
Chevalier et al., "Flexible DNA Target Site Recognition by Divergent Homing Endonuclease Isoschizomers I-Crel and I-Msol," J. Mol. Biol., vol. 329, (2003), pp. 253-269.
Curtin et al., "Targeted Mutagenesis of Duplicated Genes in Soybean and Zinc-Finger Nucleases," Plant Physiology, vol. 156, (Jun. 2011), pp. 466-473.
Doyon et al., "Directed Evolution and Substrate Specificity Profile of Homing Endonuclease I-Scel," J. Am. Chem. Soc., vol. 128, (2006), pp. 2477-2484.
Endo et al, "Molecular Characterization of True and Ectopic Gene Targeting Events at the Acetolactate Synthase Gene in *Arabidopsis*," Plant Cell Physiol, vol. 47, No. 3, (2006), pp. 372-379.
European Search Report, issued in EP12150383, dated Jul. 4, 2012.
Fauser et al., "In Planta Gene Targeting," Proceedings of the National Academy of Sciences, vol. 109, No. 19, (May 8, 2012), pp. 7535-7540.
International Preliminary Report on Patentability, issued in PCT/IB2013/050080, dated Jul. 17, 2014.
International Search Report, issued in PCT/IB2013/050080, dated May 30, 2013.
Marcaida et al., "Crystal Structure of I-Dmol in Complex with its Target DNA Provides New Insights into Meganuclease Engineering," PNAS, vol. 105, No. 44, (Nov. 4, 2008), pp. 16888-16893.

(Continued)

*Primary Examiner* — Matthew R Keogh
(74) *Attorney, Agent, or Firm* — Marshall, Gerstein & Borun LLP

(57) ABSTRACT

The present invention relates to methods to modify at least one target locus in a plant cell, comprising, providing a plant cell with one or more target loci and one or more donor loci, followed by induction of homologous recombination between homologous regions of at least one target locus and at least one donor locus by at least one rare cleaving nuclease. The present invention related also to target loci, donor loci and nuclease loci used in these methods, and plant cells, plants and plant parts comprising these target loci, donor loci, nuclease loci and/or the recombined loci.

23 Claims, 27 Drawing Sheets

Specification includes a Sequence Listing.

(56) References Cited

OTHER PUBLICATIONS

Orel et al., "Different Pathways of Homologous Recombination are Used for the Repair of Double-Strand Breaks within Tandemly Arranged Sequences in the Plant Genome," The Plant Journal, vol. 35, (2003), pp. 604-612.

Pacher et al., "Two Unlinked Double-Strand Breaks can Induce Reciprocal Exchanges in Plant Genomes via Homologous Recombination and Nonhomologous End Joining," Genetics, vol. 175, (Jan. 2007), pp. 21-29.

Salomon and Puchta, "Capture of Genomic and T-DNA Sequences During Double-Strand Break Repair in Somatic Plant Cells," The EMBO Journal, vol. 17, No. 20, (1998), pp. 6088-6095.

Shaked et al., "High-Frequency Gene Targeting in *Arabidopsis* Plants Expressing the Yeast RAD54 Gene," PNAS, vol. 102, No. 34, (Aug. 23, 2005), pp. 12265-12269.

Shukla et al., "Precise Genome Modification in the Crop Species *Zea mays* Using Zinc-Finger Nucleases," Nature, vol. 459, (May 21, 2009), pp. 437-443.

Spiegel et al., "The Structure of I-CeuI Homing Endonuclease: Evolving Asymmetric DNA Recognition from a Symmetric Protein Scaffold," vol. 14, (May 2006), pp. 869-880.

Takeuchi et al., "Optimization of in vivo Activity of a Bifunctional Homing Endonuclease and Maturase Reverses Evolutionary Degradation," Nucleic Acids Research, vol. 37, No. 3, (2009), pp. 877-890.

Tanaka et al., "High Efficient Gene Targeting on the *AGAMOUS* Gene in an *Arabidopsis AtLIG4* Mutant," Biochemical and Biophysical Research Communications, vol. 395, (2010), pp. 289-293.

Townsend et al., "High Frequency Modification ot Plant Genes Using Engineered Zinc-Finger Nucleases," Nature, vol. 459, (May 21, 2009), pp. 442-446.

Van Roey et al., "Catalytic Domain Structure and Hypothesis for Function of GIY-YIG Intron Endonuclease I-TevI," Natural Structural Biology, vol. 9, No. 11, (Nov. 2002) pp. 806-811.

Weinthal et al., "Genome Editing in Plant Cells by Zinc Finger Nucleases," Trends in Plant Science, vol. 15, No. 6, (Jun. 1, 2010). pp. 308-321.

Wright et al., "High-Frequency Homologous Recombination in Plants Mediated by Zinc-Finger Nucleases," The Plant Journal, vol. 44, (2005), pp. 693-705.

\* cited by examiner

SEQUENCE LISTING

```
<160> NUMBER OF SEQ ID NOS: 26

<210> SEQ ID NO 1
<211> LENGTH: 34
<212> TYPE: PRT
<213> ORGANISM: Artificial Sequence
<220> FEATURE:
<223> OTHER INFORMATION: 34 amino acid repeat unit of TALE nucleases

<400> SEQUENCE: 1

Leu Thr Pro Glu Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 2
<211> LENGTH: 35
<212> TYPE: PRT
<213> ORGANISM: Artificial Sequence
<220> FEATURE:
<223> OTHER INFORMATION: 35 amino acid repeat unit of TALE nuclease

<400> SEQUENCE: 2

Leu Thr Pro Glu Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

Pro His Asp
        35

<210> SEQ ID NO 3
<211> LENGTH: 19
<212> TYPE: DNA
<213> ORGANISM: Artificial Sequence
```

```
<220> FEATURE:
<223> OTHER INFORMATION: AvBS3 binding site
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t

<400> SEQUENCE: 3
tctntaaacc tnnccctct                                            19

<210> SEQ ID NO 4
<211> LENGTH: 23
<212> TYPE: DNA
<213> ORGANISM: Artificial Sequence
<220> FEATURE:
<223> OTHER INFORMATION: Hax2 binding site

<400> SEQUENCE: 4
tgttattctc acactctcct tat                                       23

<210> SEQ ID NO 5
<211> LENGTH: 13
<212> TYPE: DNA
<213> ORGANISM: Artificial Sequence
<220> FEATURE:
<223> OTHER INFORMATION: Hax3 binding site
<220> FEATURE:
<221> NAME/KEY: misc_feature
<222> LOCATION: (8)..(10)
<223> OTHER INFORMATION: n is a, c, g, or t

<400> SEQUENCE: 5
tacacccnnn cat                                                  13

<210> SEQ ID NO 6
<211> LENGTH: 16
<212> TYPE: DNA
<213> ORGANISM: Artificial Sequence
<220> FEATURE:
<223> OTHER INFORMATION: Hax4 binding site
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 6
tacctnnact anatat                                               16

<210> SEQ ID NO 7
<211> LENGTH: 18
<212> TYPE: DNA
<213> ORGANISM: Artificial Sequence
<220> FEATURE:
<223> OTHER INFORMATION: rare cleaving nuclease cutting site of I-SceI

<400> SEQUENCE: 7
tagggataac agggtaat                                             18
```

```
<210> SEQ ID NO 8
<211> LENGTH: 22
<212> TYPE: DNA
<213> ORGANISM: Artificial Sequence
<220> FEATURE:
<223> OTHER INFORMATION: rare cleaving nuclease cutting site of I-CreI

<400> SEQUENCE: 8
caaaacgtcg tgagacagtt tc                                           22

<210> SEQ ID NO 9
<211> LENGTH: 22
<212> TYPE: DNA
<213> ORGANISM: Artificial Sequence
<220> FEATURE:
<223> OTHER INFORMATION: rare cleaving nuclease cutting site of I-CeuI

<400> SEQUENCE: 9
ataacggtcc taaggtagcg aa                                           22

<210> SEQ ID NO 10
<211> LENGTH: 30
<212> TYPE: DNA
<213> ORGANISM: Artificial Sequence
<220> FEATURE:
<223> OTHER INFORMATION: rare cleaving nuclease cutting site of I-DmoI

<400> SEQUENCE: 10
atgccttgcc gggtaagttc cggcgcgcat                                   30

<210> SEQ ID NO 11
<211> LENGTH: 22
<212> TYPE: DNA
<213> ORGANISM: Artificial Sequence
<220> FEATURE:
<223> OTHER INFORMATION: rare cleaving nuclease cutting site of I-MsoI

<400> SEQUENCE: 11
cagaacgtcg tgagacagtt cc                                           22

<210> SEQ ID NO 12
<211> LENGTH: 30
<212> TYPE: DNA
<213> ORGANISM: Artificial Sequence
<220> FEATURE:
<223> OTHER INFORMATION: rare cleaving nuclease cutting site of PI-PsiI

<400> SEQUENCE: 12
atctatgtcg ggtgcggaga aagaggtaat                                   30

<210> SEQ ID NO 13
<211> LENGTH: 31
<212> TYPE: DNA
<213> ORGANISM: Artificial Sequence
<220> FEATURE:
<223> OTHER INFORMATION: rare cleaving nuclease cutting site of I-AniI

<400> SEQUENCE: 13
gcgcgctgag gaggtttctc tgtaaagcgc a                                 31

<210> SEQ ID NO 14
<211> LENGTH: 18
<212> TYPE: DNA
<213> ORGANISM: Artificial Sequence
<220> FEATURE:
<223> OTHER INFORMATION: probe A primer1
```

```
<400> SEQUENCE: 14
gttgtgggag gtgatgtc                                                 18

<210> SEQ ID NO 15
<211> LENGTH: 18
<212> TYPE: DNA
<213> ORGANISM: Artificial Sequence
<220> FEATURE:
<223> OTHER INFORMATION: probe A primer2

<400> SEQUENCE: 15
ccgagaacgt catcaccg                                                 18

<210> SEQ ID NO 16
<211> LENGTH: 24
<212> TYPE: DNA
<213> ORGANISM: Artificial Sequence
<220> FEATURE:
<223> OTHER INFORMATION: probe B1 primer1

<400> SEQUENCE: 16
cttggattga acaagatgga ttgc                                          24

<210> SEQ ID NO 17
<211> LENGTH: 23
<212> TYPE: DNA
<213> ORGANISM: Artificial Sequence
<220> FEATURE:
<223> OTHER INFORMATION: probe B primer 2

<400> SEQUENCE: 17
cagaagaact cgtcaagaag gcg                                           23

<210> SEQ ID NO 18
<211> LENGTH: 24
<212> TYPE: DNA
<213> ORGANISM: Artificial Sequence
<220> FEATURE:
<223> OTHER INFORMATION: kanamycin-specific probe primer1

<400> SEQUENCE: 18
ctagattcga cggtatcgat aagc                                          24

<210> SEQ ID NO 19
<211> LENGTH: 23
<212> TYPE: DNA
<213> ORGANISM: Artificial Sequence
<220> FEATURE:
<223> OTHER INFORMATION: kanamycin-specific probe primer2

<400> SEQUENCE: 19
gattggttat gaaattcaga tgc                                           23

<210> SEQ ID NO 20
<211> LENGTH: 21
<212> TYPE: DNA
<213> ORGANISM: Artificial Sequence
<220> FEATURE:
<223> OTHER INFORMATION: upstream HR-mediated integration primer1

<400> SEQUENCE: 20
gaccacttcg tacaacacta g                                             21
```

```
<210> SEQ ID NO 21
<211> LENGTH: 23
<212> TYPE: DNA
<213> ORGANISM: Artificial Sequence
<220> FEATURE:
<223> OTHER INFORMATION: upstream HR-mediated integration primer2

<400> SEQUENCE: 21
ctactaatca tcatctatct gtg                                              23

<210> SEQ ID NO 22
<211> LENGTH: 20
<212> TYPE: DNA
<213> ORGANISM: Artificial Sequence
<220> FEATURE:
<223> OTHER INFORMATION: restored GUS gene primer1

<400> SEQUENCE: 22
gttcatttca tttggagagg                                                  20

<210> SEQ ID NO 23
<211> LENGTH: 20
<212> TYPE: DNA
<213> ORGANISM: Artificial Sequence
<220> FEATURE:
<223> OTHER INFORMATION: restored GUS gene primer2

<400> SEQUENCE: 23
gacgaccaaa gccagtaaag                                                  20

<210> SEQ ID NO 24
<211> LENGTH: 22
<212> TYPE: DNA
<213> ORGANISM: Artificial Sequence
<220> FEATURE:
<223> OTHER INFORMATION: restored donor region primer1

<400> SEQUENCE: 24
cactagtcta gagtcgatcg ac                                               22

<210> SEQ ID NO 25
<211> LENGTH: 21
<212> TYPE: DNA
<213> ORGANISM: Artificial Sequence
<220> FEATURE:
<223> OTHER INFORMATION: restored donor region primer2

<400> SEQUENCE: 25
gggcaatgca gatccggatg c                                                21

<210> SEQ ID NO 26
<211> LENGTH: 9
<212> TYPE: PRT
<213> ORGANISM: Artificial Sequence
<220> FEATURE:
<223> OTHER INFORMATION: conserved motif of endonucleases

<400> SEQUENCE: 26

Leu Ala Gly Leu Ile Asp Ala Asp Gly
1               5
```

IN PLANTA RECOMBINATION

This application is a National Stage application of International Application No. PCT/IB2013/050080, filed Jan. 4, 2013, which claims the benefit of U.S. Provisional Application No. 61/583,651, filed Jan. 6, 2012. This application also claims priority under 35 U.S.C. § 119 to European Patent Application No. 12150383.3, filed Jan. 6, 2012.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "Seq_List.txt" created on Jan. 4, 2013, and is 8,192 bytes in size. The sequence listing contained in this .txt file is part of the specification and is hereby incorporated by reference herein in its entirety.

FIELD OF THE INVENTION

The present invention relates to methods to modify at least one target locus in a plant cell, comprising, providing a plant cell with one or more target loci and one or more donor loci, followed by induction of homologous recombination between homologous regions of at least one target locus and at least one donor locus by at least one rare cleaving nuclease. The present invention related also to target loci, donor loci and nuclease loci used in these methods, and plant cells, plants and plant parts comprising these target loci, donor loci, nuclease loci and/or the recombined loci.

BACKGROUND OF THE INVENTION

Modern transgenic techniques allow to integrate new genetic information in genomes of plants. Despite the general success of this technology, many applications suffer from the fact that the integration site of the transgenic sequences in the genome, as well as their copy number can not be predicted and appear to be random. Thus, it is basically impossible to integrate a particular nucleotide sequence at a predetermined locus in the genome or to exchange one genomic nucleotide sequence with another nucleotide sequence at a particular genomic locus, if not more sophisticated technologies are used. Those technologies usually involve the application of enzymes to enhance the probability that the new nucleotide sequence is integrated at a predetermined genomic locus. Enzymes which have been applied for those purposes are for example recombinases and resolvases, which have the ability to integrate polynucleotides at a given locus, if this locus comprises recombination sites which can be recognized by those enzymes and used for the recombination reaction. An alternative technology uses homologous recombination (HR) to integrate or exchange nucleotide sequences at genomic loci, whereby the frequency of homologous recombination is enhanced by induced DNA-double strand breaks at, or close by the targeted genomic locus. The necessary DNA-double strand breaks are usually induced by providing the cell with sequence specific nucleases, which recognize nucleotide sequences of more than 10 base pairs. DNA-recognition sites of this length should for statistical reasons occur only once or a few times per genome, which has the advantage that unintended DNA cleavage at other genomic loci is reduced to a minimum. Because of the huge variety of available nucleases of natural and engineered origin, basically every sequence of a given genome can be addressed with a nuclease being specific for such a sequence. This can be used to induce DNA double strand breaks in order to exchange or delete DNA sequences between chromosomes or to break linkage groups of genes, as disclosed for example in WO10143917 or US2011203012.

While the use of induced DNA-double strand breaks at the target locus helped to improve the frequency of successful events of targeted integration (TI) or targeted exchange (TE) of DNA sequences, the frequency is still very low. Thus, several further approaches have been used in order to raise the number of successful TI- and TE-events. For example: WO2005/049842 provides methods for the directed introduction of a foreign DNA fragment at a preselected insertion site in the genome of a plant, wherein the foreign DNA fragment is introduced in the target cell via direct transformation methods like PEG mediated DNA uptake in protoplast, microprojectile bombardment or silicon whisker mediated transformation.

WO2006/1105946, WO 2008/148559, WO 2008/037436 and WO 2008/145731 disclose methods which allow for the efficient removal, or exchange of a selected part of a DNA sequence of interest wherein the sequence specific nuclease is provided via crossing of two plants, thereby avoiding tissue culture effects. A further problem of TI integration approaches is an unintended repair of the induced DNA double strand break via the Non-Homologous-End-Joining (NHEJ) DNA repair mechanism. NHEJ frequently leads to unwanted mutations at the target locus, but will in most cases lead to the loss of the nuclease cutting site, resulting in the loss of the positive effect on the frequency of HR with the DNA sequence to be integrated. As stated in WO2011/091317, NHEJ is usually more frequent than HR. One further approach to achieve a higher frequency of TI events is to amplify the copy number of the DNA sequence to be integrated, for example as disclosed in WO02077246.

Another problem of TI techniques is the integration of the DNA sequence of interest at one or more genomic loci which are not the predetermined locus, thereby creating so called ectopic events. These ectopic events are usually unwanted and will therefore have to be deleted via segregation during further crossings, which can be very time consuming and add considerable costs. Ectopic events can be avoided by integrating detrimental or toxic genes in the construct comprising the DNA sequence to be integrated, in such a way that these detrimental or toxic genes are not integrated at the predetermined locus, but will only be integrated in ectopic events. Such techniques have been disclosed for example in WO04022745 or in Endo et al. (2006) "Molecular Characterization of True and Ectopic Gene Targeting Events at the Acetolactate Synthase Gene in *Arabidopsis*"; Plant Cell Physiol.; Vol. 47(3); Pages 372 to 379. However, integration of detrimental or toxic genes might lead to a lower frequency of TI events, because many cells comprising a TI event will also comprise one or more ectopic events facing the detrimental or toxic effect.

Despite the already achieved improvements due to the technologies described above, there is still a need to improve the frequency of successful integrations at the predetermined locus, as well as to lower the frequency of unintended truncations of the integrated or exchanged polynucleotide and/or to lower the frequency of unintended mutations at the predetermined locus due to NHEJ. There is further a need to reduce the number of ectopic integrations, in order to avoid costly and time consuming crossings to eliminate these superfluous copies by segregation.

The present invention provides new methods for homologous recombination and new designs of target as well as donor loci capable to enhance the frequency of successful targeted integration of non-truncated sequences of interest and to reduce the frequency of ectopic integrations, thereby enhancing the feasibility of targeted integration technologies.

SUMMARY OF THE INVENTION

Encompassed by the invention is a method for modifying at least one target locus in a plant cell, comprising the following steps: a) providing a plant cell comprising at least one target locus comprising at least one homologous region A and at least one homologous region B and comprising at least one nucleotide sequence Z located between at least one homologous region A and at least one homologous region B and comprising at least one donor locus comprising at least one homologous region C and at least one homologous region D and comprising at least one nucleotide sequence X located between at least one homologous region C and at least one homologous region D, wherein homologous region(s) A and homologous region(s) C have sufficient sequence identity to be able to recombine via homologous recombination and homologous region(s) B and homologous region(s) D have sufficient sequence identity to be able to recombine via homologous recombination and wherein the at least one target locus and the at least one donor locus are integrated in the chromosomal DNA of the plant cell and wherein the at least one target locus comprises one or more rare cleaving nuclease cutting site(s) located between at least one homologous region A and at least one homologous region B and wherein the at least one donor locus comprises one or more rare cleaving nuclease cutting site(s) flanking a nucleotide sequence of the donor locus comprising at least one homologous region C and at least one homologous region D, b) providing the plant cell of step a) with at least one rare cleaving nuclease being able to nick or cut at least one rare cleaving nuclease cutting site located in the at least one target locus or located in the at least one donor locus or located in the at least one target locus and at least one donor locus, c) allowing the rare cleaving nuclease to nick or cleave at least one of the rare cleaving cutting sites of step a), d) allowing homologous region A and homologous region C of step a) to recombine and allowing homologous region B and homologous region D of step a) to recombine.

A further embodiment of the invention is a method for modifying at least one target locus in a plant cell, comprising the following steps: a) providing a plant cell comprising at least one target locus integrated in the chromosomal DNA of the plant cell wherein the at least one target locus comprises at least one homologous region A and at least one homologous region B and comprising at least one nucleotide sequence Z located between at least one homologous region A and at least one homologous region B and wherein nucleotide sequence Z is flanked by at least one rare cleaving nuclease cutting site on each side of nucleotide sequence Z, and b) providing the plant cell of step a) with at least one donor locus comprising at least one homologous region C and at least one homologous region D and comprising at least one nucleotide sequence X located between at least one homologous region C and at least one homologous region D, wherein homologous region(s) A and homologous region(s) C have sufficient sequence identity to be able to recombine via homologous recombination and homologous region(s) B and homologous region(s) D have sufficient sequence identity to be able to recombine via homologous recombination and wherein the at least one donor locus comprises one or more rare cleaving nuclease cutting site(s) flanking a nucleotide sequence of the donor locus comprising at least one homologous region C and at least one homologous region D, c) providing the plant cell of step a) or step b) with at least one rare cleaving nuclease being able to nick or cut at least one rare cleaving nuclease cutting site located in the at least one target locus or located in the at least one donor locus or located in the at least one target locus and at least one donor locus, d) allowing the rare cleaving nuclease to nick or cleave at least one of the rare cleaving cutting sites of step a) and step b), e) allowing homologous region A and homologous region C of step a) and step b) to recombine and allowing homologous region B and homologous region D of step a) and step b) to recombine.

A further embodiment of the invention is a method as described above, wherein the at least one rare cleaving nuclease is provided to a plant cell comprising at least one target locus and comprising at least one donor locus integrated in the chromosomal DNA of the plant cell, or wherein the at least one rare cleaving nuclease is provided together with a donor locus to a plant cell comprising at least one target locus integrated in the chromosomal DNA. An even further embodiment of the invention is a method as described above, wherein the rare cleaving nuclease is provided to a plant cell comprising at least one target locus and comprising at least one donor locus integrated in the chromosomal DNA of the plant cell, or wherein the at least one rare cleaving nuclease is provided together with a donor locus to a plant cell comprising at least one target locus integrated in the chromosomal DNA via crossing or fusion with another plant or plant cell comprising at least one expression cassette being able to express the at least one rare cleaving nuclease, or via stable or transient transformation with at least one expression cassette being able to express the at least one rare cleaving nuclease in the plant cell or a progeny cell thereof, or via infection with a viral vector comprising at least one expression cassette being able to express the at least one rare cleaving nuclease in the plant cell or a progeny cell thereof, or via inducing expression of at least one rare cleaving nuclease in the plant cell or a progeny cell thereof, or via introduction of mRNA coding for the at least one rare cleaving nuclease in the plant cell, or via introduction of at least one rare cleaving nuclease via particle bombardment, or bacterial SecIII or SecIV secretion systems, or peptide mediated cell-membrane transfer, in the plant cell.

Further embodiments of the invention are methods as described above, wherein the at least two rare cleaving nucleases are provided to the plant cell comprising at least one target locus and comprising at least one donor locus integrated in the chromosomal DNA of the plant cell, or are provided together with a donor locus to the plant cell comprising at least one target locus integrated in the chromosomal DNA of the plant cell, wherein one rare cleaving nuclease is able to nick or cut at least one rare cleaving nuclease cutting site of the at least one target locus and the other rare cleaving nuclease is able to nick or cut at least one rare cutting nuclease cutting site of the at least one donor locus.

An additional embodiment of the invention is any method as described above, wherein the target locus is provided together with at least one rare cleaving nuclease being able to cut or nick at least one rare cleaving nuclease cutting site located in the at least one donor locus, but not being able to cut or nick a rare cleaving nuclease cutting site located in the at least one target locus, or the donor locus is provided together with at least one rare cleaving nuclease being able to cut or nick at least one rare cleaving nuclease cutting site located in the at least one target locus, but not being able to cut or nick a rare cleaving nuclease cutting site located in the at least one donor locus, or wherein the target locus is provided together with at least one rare cleaving nuclease being able to cut or nick at least one rare cleaving nuclease cutting site located in the at least one donor locus, but not being able to cut or nick a rare cleaving nuclease cutting site located in the at least one target locus and the donor locus is provided together with at least one rare cleaving nuclease being able to cut or nick at least one rare cleaving nuclease cutting site located in the at least one target locus, but not being able to cut or nick a rare cleaving nuclease cutting site located in the at least one donor locus An even further embodiment of the invention is any method as described above, wherein at least one rare cleaving nuclease is a meganuclease, or a TALE-nuclease, or a Zinc-finger nuclease, or a chimeric nuclease, and has nicking or cutting activity.

Also encompassed by the invention are any kind of methods as described above, wherein at least one donor locus comprises at least one homologous region E and at least one homologous region F, wherein homologous region(s) E and homologous region(s) F have sufficient sequence identity to be able to recombine via homologous recombination and wherein the at least one homologous region E and the least one homologous region F flank the at least one homologous region C and the at least one homologous region D.

A further embodiment of the invention is any method as described above, wherein the donor locus comprises an expression cassette for a selection marker, suitable to be expressed in the plant cells described above. Preferably the expression cassette for the selection marker is located between at least one homologous region C and at least one homologous region D, or between at least one homologous region E and at least one homologous region F, but outside of at least one homologous region C and at least one homologous region D, or outside of at least one homologous region E and at least one homologous region F and outside of at least one homologous region C and at least one homologous region D.

Even further embodiments of the invention is any method as described above, wherein the at least one donor locus comprises at least one rare cleaving nuclease cutting site, which cannot be cut by the or any of the nucleases provided to the plant cells described above, or wherein the at least one donor locus comprises at least two recombination sites capable to undergo a recombination reaction, in case the recombinase recognizing those sites is provided, or wherein the at least one donor locus comprises at least one rare cleaving nuclease cutting site, which cannot be cut by the or any of the nucleases provided to the plant cells described above and comprises at least two recombination sites capable to undergo a recombination reaction, in case the recombinase recognizing those sites is provided.

An additional embodiment of the invention are methods as described above, wherein no donor locus comprises a lethal gene or conditional lethal gene suitable to be expressed in the plant cell described above or their progeny cells, located outside homologous region C and homologous region D and outside of region X.

In a further embodiment of the invention, the methods as described above employ at least one target locus comprising an expression cassette for a selection marker being able to express the selection marker in a plant cell described above or a progeny cell thereof.

Another embodiment of the invention are methods as described above, wherein the expression cassette for the selection marker is located between at least one homologous region A and at least one homologous region B, or outside of at least one homologous region A and at least one homologous region B. In a preferred embodiment of the methods being described above, the expression cassette for the selection marker or at least a part of the expression cassette for the selection marker is located between two rare cleaving nuclease cutting sites.

Further embodiments of the invention are any kind of methods as described above, wherein the at least one target locus or at least one donor locus or at least one target locus and at least one donor locus comprise one or more genes other than marker genes. Preferably those genes are HR modifying sequences or male sterility restorer genes or genes which are in a functional relationship, wherein the functional relationship is an additional or synergistic effect on a plant trait, or cooperation of these genes or the products of those genes in a signaling pathway, or a metabolic pathway, or a defense reaction to a plant pathogen or a group of plant pathogens.

Another embodiment of the invention is any method described above, wherein the rare cleaving nuclease cutting site(s) of at least one target locus and the rare cleaving nuclease cutting site(s) of the at least one donor locus, can be nicked or cut with a single rare cleaving nuclease provided to the plant cells.

An even further embodiment of the invention is any method described above, wherein at least one target locus and at least one donor locus are located on homologous chromosomes, or in homologous regions of non-homologous chromosomes.

An additional embodiment of the invention are methods as described above, the least one target locus and the at least one donor locus are allelic or are not allelic to each other.

Also part of the invention are methods as described above, wherein at least one target locus or at least one donor locus, or wherein at least one target locus and at least one donor locus comprise an expression cassette for the rare cleaving nuclease used to induce the homologous recombination. Preferably the expression cassette for the rare cleaving nuclease is located, between at least one homologous region A and at least one homologous region B, or outside of at least one homologous region A and at least one homologous region B, or between at least one homologous region C and at least one homologous region D, or between at least one homologous region E and at least one homologous region F, but outside of at least one homologous region C and at least one homologous region D, or outside of at least one homologous region E and at least one homologous region F.

In a further embodiment of the invention, the rare cleaving nuclease used in any of the methods described above, is provided via a nuclease locus. Preferably the nuclease locus comprises at least one homologous region I and at least one homologous region J, or comprises at least one rare cleaving nuclease cutting site, which can be cut or nicked by the rare cleaving nuclease encoded on the nuclease locus, or comprises a homologous region I and a homologous region J and at least one rare cleaving nuclease cutting site, which can be cut or nicked by the rare cleaving nuclease encoded on the nuclease locus.

An additional embodiment of the invention are methods as described above, wherein the at least one rare cleaving nuclease is expressed via a constitutive promoter, or an inducible promoter, or a tissue specific promoter, or an organ specific promoter, or a developmental stage specific promoter, or is transported inside the cell nucleus upon an external, or tissue specific, or organ specific, or developmental stage specific stimulus, preferably the specific stimulus is provision of a chemical being able to induce the nuclear import of a nuclear receptor domain, even more preferred the nuclear receptor domain is a glucocorticoid receptor domain.

Further embodiments of the invention are methods as described above, wherein the plant cell comprises two or more target loci each comprising at least one homologous region A and at least one homologous region B, or two or more donor loci each comprising at least one homologous region C and at least one homologous region D, or two or more target loci each comprising at least one homologous region A and at least one homologous region B and two or more donor loci each comprising at least one homologous region C and at least one homologous region D, and wherein all homologous region(s) A and all homologous region(s) C have sufficient sequence identity to be able to recombine via homologous recombination and all homologous region(s) B and all homologous region(s) D have sufficient sequence identity to be able to recombine via homologous recombination.

In even further embodiments of the invention, the methods described above use plant cells being homozygous for at least one target locus, or being homozygous for at least one donor locus, or being homozygous for at least one target locus and homozygous for at least one donor locus.

In additional embodiments of the invention, the methods described above comprise plant cells, wherein the proportion of the target locus to the donor loci or the proportion of the target loci to the donor locus or the proportion of the target loci to the donor loci, is 1:1, 1:2, 1:3, 1:4, 1:5, 1:6, or 6:1, 5:1, 4:1, 3:1, 2:1.

Additional embodiments of the invention comprise any kind of method described above, wherein the nucleotide sequence between homologous region(s) A and homologous region(s) B of at least two target loci is not identical, or the nucleotide sequence between homologous region(s) C and homologous region(s) D of at least two donor loci is not identical, or the nucleotide sequence between homologous region(s) A and homologous region(s) B of the at least two target loci is not identical and the nucleotide sequence between homologous region(s) C and homologous region(s) D of at least two donor loci is identical or is not identical.

Further embodiments comprise methods as described above, wherein at least one target locus, or at least one donor locus, or at least one target locus and at least one donor locus is a transgenic locus, or a naturally occurring locus.

Further embodiments of the invention encompass methods as described above, wherein the at least one target locus and the at least one donor locus in the plant cells described above, or wherein the at least one target locus and the at least one donor locus in cells of a plant used to provide the plant cell described above are combined via co-transformation of polynucleotides comprising the at least one target locus or comprising the at least one donor locus, or comprising the at least one target locus and comprising the at least one donor locus, or wherein the at least one target locus and the at least one donor locus in the plant cells described above, or the at least one target locus and the at least one donor locus in cells of a plant used to provide the plant cell described above are combined via transformation with at least one polynucleotide comprising the at least one target locus or comprising the at least one donor locus, or comprising the at least one target locus and comprising the at least one donor locus.

A further embodiment of the invention is any method as described above, wherein the at least one target locus and the at least one donor locus of the plant cell described above, or of cells of a plant used to provide the plant cell described above, are combined via crossing of a plant comprising the least one target locus in pollen or egg cells with another plant comprising the at least one donor locus in pollen or egg cells.

Also encompassed by the present invention are embodiments of any method described above, wherein the plant used to provide the plant cell described above, or the plants being crossed in order to provide a plant able to provide the plant cells described above, are checked for integrity or chromosomal localization or checked for integrity and chromosomal localization, of the at least one target locus or the at least one donor locus or for integrity of the at least one target locus and the at least one donor locus.

Further embodiments encompass a method as described above, wherein the plant cells used for homologous recombination are homozygous, or are heterozygous. In one embodiment, they are double-haploid cells.

Also comprised by the invention are methods as described above, comprising the step of growing progeny cells of the plant cells used for homologous recombination into a plant, preferably into a fertile plant. In additional embodiments, the fertile plant is used for further crossings or for the production of double haploid plant cells or double haploid plants.

Additional embodiments of the invention comprise methods as described above, comprising the step of out-crossing or excision of at least one donor locus or of at least one target locus, or of at least one nuclease locus, or of at least one recombined locus, e.g. a new donor locus, or a new nuclease locus.

Even further embodiments of the invention comprise DNA constructs and/or plant chromosomes comprising one or more target loci, and/or one or more donor loci, and/or one or more nuclease loci, and/or one or more recombined loci being described above, as well as plant cells, plant nuclei, plant parts and plants comprising one or more target loci, and/or one or more donor loci, and or one or more nuclease loci, and/or one or more recombined loci. In an preferred embodiment of the invention the DNA constructs, plant chromosomes, plant cells, plant nuclei, plant parts and plants comprise one or more target loci, and/or one or more donor loci, and/or one or more nuclease loci, and/or one or more recombined loci, described in FIGS. 1 to 18, including the description of FIGS. 1 to 18. Further embodiments comprise plant chromosomes, plant cells, plant nuclei, plant parts and plants comprising a combination of target loci, donor loci and/or nuclease loci as described in FIGS. 19 to 22, including the description of FIG. 19 to A further embodiment of the invention are plant chromosomes, plant cells, plant nuclei, plant parts and plants produced by any one of the methods described herein.

Even further embodiments comprise plant cells or plant cell nuclei comprising at least one target locus, which comprises at least one homologous region A and at least one homologous region B and comprises at least one donor locus comprising at least one homologous region C and at least one homologous region D, wherein homologous region(s) A and homologous region(s) C have sufficient sequence identity to be able to recombine via homologous recombination and homologous region(s) B and homologous region(s) D have sufficient sequence identity to be able to recombine via homologous recombination and wherein the at least one target locus and the at least one donor locus are integrated in the chromosomal DNA of the plant cell and wherein the at least one target locus comprises one or more rare cleaving nuclease cutting site(s) located between at least one homologous region A and at least one homologous region B and wherein the at least one donor locus comprises one or more rare cleaving nuclease cutting site(s) flanking a nucleotide sequence of the donor locus comprising at least one homologous region C and at least one homologous region D.

Another embodiment of the invention are plant cells or plant cell nuclei comprising at least one target locus integrated in the chromosomal DNA of the plant cell, wherein the at least one target locus comprises at least one homologous region A and at least one homologous region B and comprises at least one nucleotide sequence Z located between the at least one homologous region A and the at least one homologous region B and wherein the nucleotide sequence Z is flanked by at least one rare cleaving nuclease cutting site on each side of nucleotide sequence Z.

Preferably the plant cells or plant nuclei described above comprise at least one nuclease locus.

Further embodiments comprises plant cell nuclei, plant cells, or plants comprising a combination of target loci or a combination of target loci and nuclease loci, or a combination of donor loci or a combination of target loci and donor loci, or a combination of target loci, donor loci and nuclease loci as described in FIGS. 19 to 22, including the description of FIGS. 19 to 22.

BRIEF DESCRIPTION OF THE DRAWINGS

FIG. 6 uses the same symbols having the same meaning as in FIG. 5. The main difference to the alternative donor loci designs of FIG. 5 is that the expression cassette for a selection marker (M) is located close to homologous region F (donor locus I of FIG. 6) or located close to homologous region E (donor locus II of FIG. 6). Both donor loci of FIG. 6 comprise at least one or two rare cleaving nuclease cutting sites located between homologous regions E and C or homologous regions D and F or located between homologous regions E and C and homologous regions E and F.

FIG. 13 describes an alternative design, in which the rare cleaving nuclease expressed from the expression cassette of the target locus (Nucl. II) cuts or nicks preferably the one, two, three or more rare cleaving nuclease cutting sites of the alternative donor loci (II.1, II.2 and if present II.3), while the rare cleaving nuclease expressed from the expression cassette of the donor locus (Nucl. I) cuts or nicks preferably the one, two, three or more rare cleaving nuclease cutting sites of the target locus (I.1 and I.2).

FIG. 14 comprises two additional regions in the donor locus (region O and region P). Both regions comprise not sufficient sequence identity to allow for homologous recombination between each other, but comprise elements which are operatively linked to the sequence of homologous region E and homologous region F, so that region O, recombined homologous region E/F and region P form a functional unit, e.g. region O may be a promoter, recombined homologous region E/F may be a coding region for a protein and region P may be a terminator sequence, in a further example region O may be a first part of a coding region, recombined homologous region E/F may be an intron and region P may be a second part of a coding region. A person skilled in the art will readily imagine further variations of this principle.

FIG. 20 is intended to represent also a design of target loci and donor loci, which comprise rare cleaving nuclease cutting sites, which can be nicked or cut by a single rare cleaving nuclease, or may comprise different rare cleaving nuclease cutting sites, in order to induce e.g. targeted integration or targeted exchange at target locus I, in case one rare cleaving nuclease is used or to induce targeted integration or targeted exchange at target locus II if another rare cleaving nuclease is used. FIG. 20 is intended to represent also a design of target loci and donor loci, which comprise similar or identical homologous regions, e.g. target locus I may comprise homologous regions A and B which could undergo homologous recombination with the homologous regions C and D of donor locus I but not with donor locus II, which may only be able to undergo homologous recombination with target locus II, but in a different situation, target locus I may comprise homologous regions A and B which could undergo homologous recombination with the homologous regions C and D of donor locus I and with donor locus II. Further variations of targeting donor locus I or donor locus II to either target locus I or target locus II or to both are also included. The target loci and donor loci of all those designs represented by FIG. 20 may be located at any place or chromosome of the plant cell, for example donor loci and target loci may be located on non-homologous chromosomes or may be located at the same, on homologous chromosomes or located on a chromosome and on a region of a non-homologous chromosome, wherein this region is homologous to the first chromosome. Preferably at least one donor locus is located on a homologous chromosome to the chromosome, wherein the respective target locus is located, or is located in a chromosomal region of a non-homologous chromosome, wherein this region is homologous to a region of a different chromosome wherein the respective target locus is located.

FIG. 21 is also intended to represent a situation, wherein the target locus comprises rare cleaving nuclease cutting sites for several rare cleaving nucleases, while the donor loci comprise rare cleaving nuclease cutting sites or only one rare cleaving nuclease per donor locus, so that different donor loci might be directed to the same target locus depending on the rare cleaving nuclease being used to induce homologous recombination. This may be used to test the effect of different regions X at the same target locus or to stack different regions X of different donor loci at one target locus.

FIG. 22 is also intended to represent a situation, wherein donor locus I comprises rare cleaving nuclease cutting sites for several rare cleaving nucleases, while the different target loci comprise rare cleaving nuclease cutting sites or only one rare cleaving nuclease per target locus, so that region X of donor locus I might be directed to the different target loci, depending on the rare cleaving nuclease being used to induce homologous recombination. This may for example be used to test the effect of region X of donor locus I at different target loci or to combine region X of donor locus I with different genes located close to the different target loci in order to create new linkage groups for further crossings or to replace different regions Z of the different target loci with the same region X of the donor locus I in order to test the effect of deletions of different regions Z.

GENERAL DEFINITIONS

Figure 1:
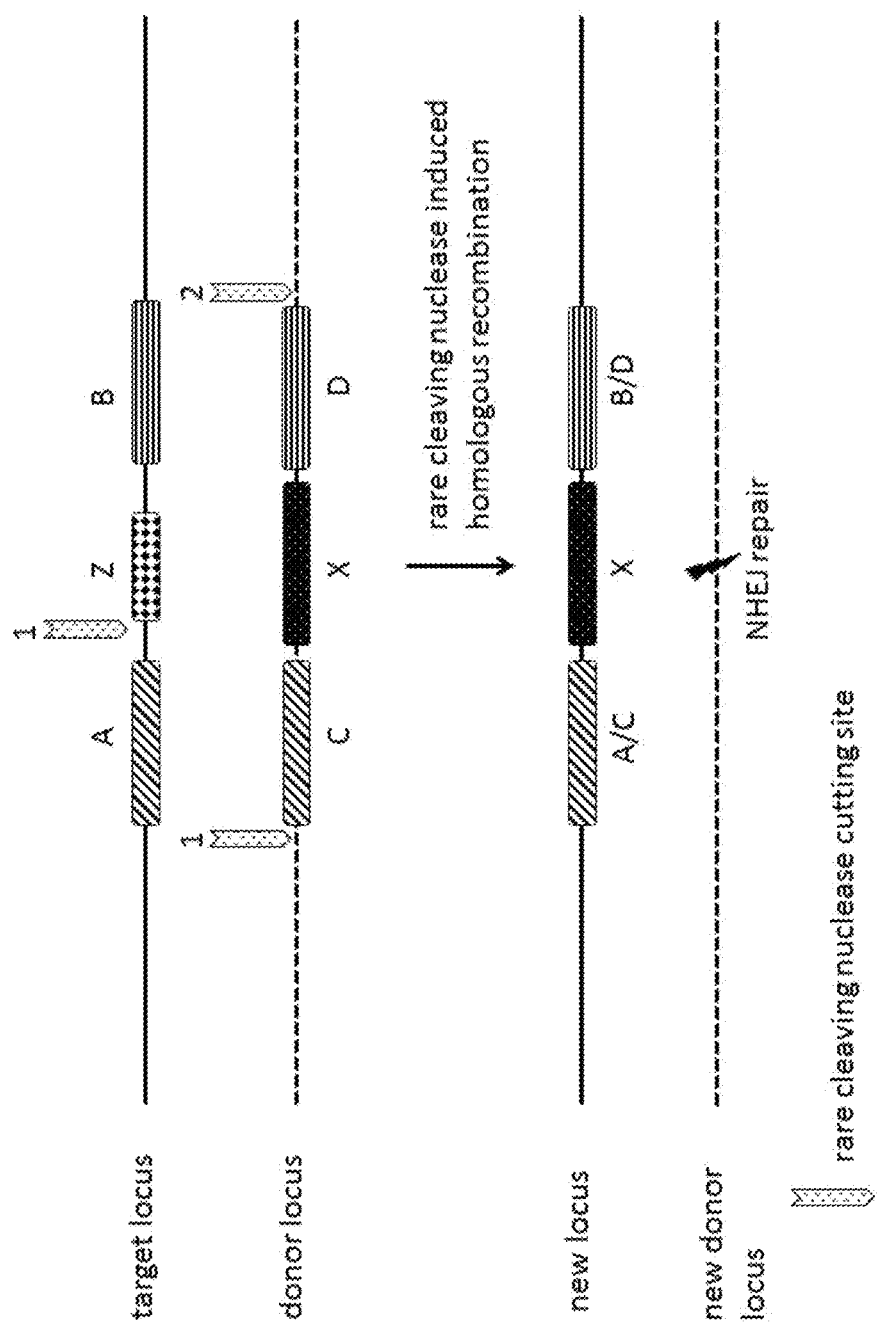
FIG. 1 depicts a schematic representation of a target locus being integrated in a nuclear genome and comprising a homologous region A and a homologous region B, which flank a rare cleaving nuclease cutting site. The rare cleaving nuclease cutting site is close to a region Z and may be upstream or downstream of region Z or may be located in region Z. Also depicted is a schematic representation of a donor locus being integrated in the nuclear genome and comprising a homologous region C and a homologous region D, which are flanked by at least one rare cleaving nuclease cutting site 1 or 2, but are preferably flanked by at least two rare cleaving nuclease cutting sites 1 and 2. The donor locus comprises also a region X, which is located between homologous region C and homologous region D. An arrow represents cleavage of rare cleaving nuclease cutting sites followed by homologous recombination between homologous region A and homologous region C as well as homologous region B and homologous region D, resulting in a new locus and a new donor locus. The new locus depicted in FIG. 1 comprises region A/C, representing the resulting sequence of the homologous recombination of homologous region A and homologous region C, and comprises region B/D, representing the resulting sequence of the homologous recombination of homologous region B and homologous region D, thereby exchanging region Z with region X. The lightning symbol depicted in the new donor locus represents a new sequence resulting from DNA repair via non homologous end joining (NHEJ).
Figure 2:
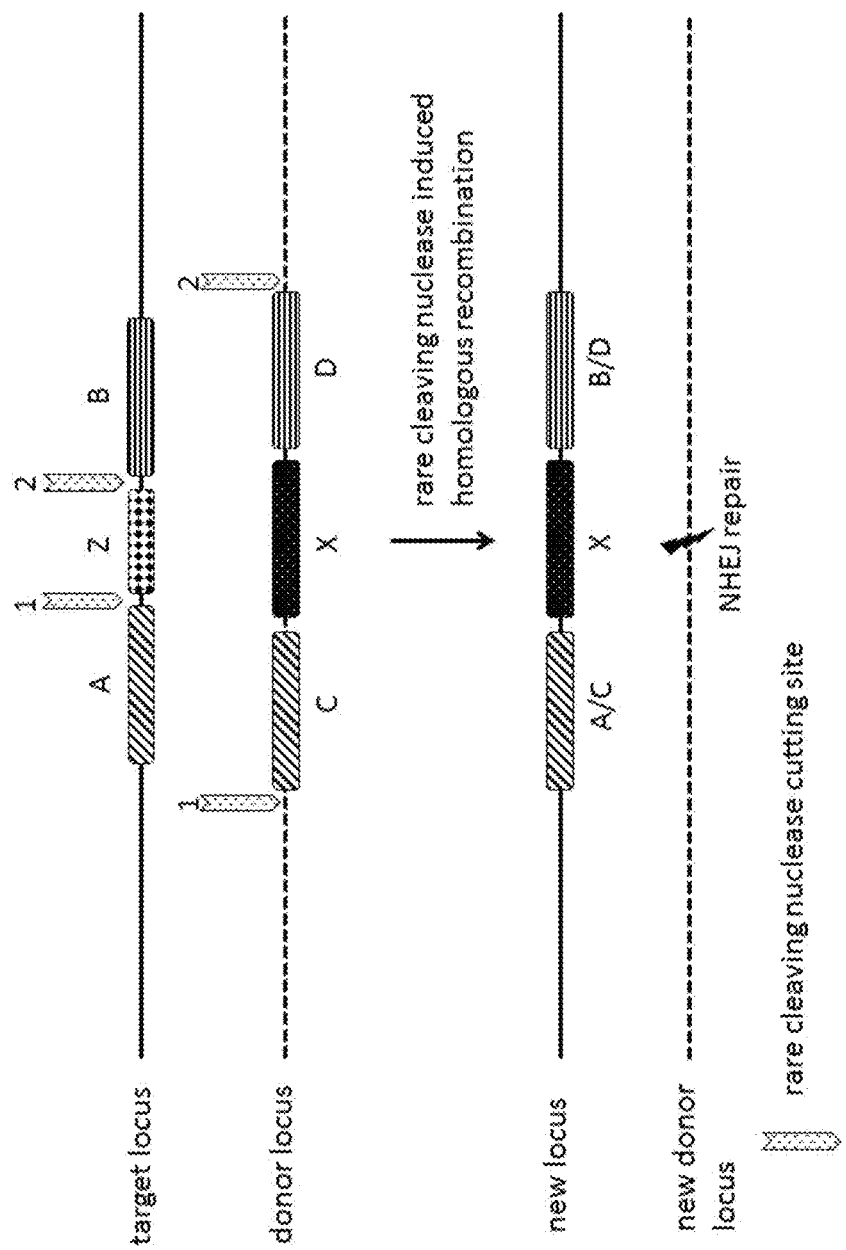
FIG. 2 depicts a very similar design as FIG. 1, meaning that all symbols used have the same meaning as described for FIG. 1. Different to the design of FIG. 1 is that the target locus comprises a region Z, which is flanked on both sites by rare cleaving nuclease cutting sites.
Figure 3:
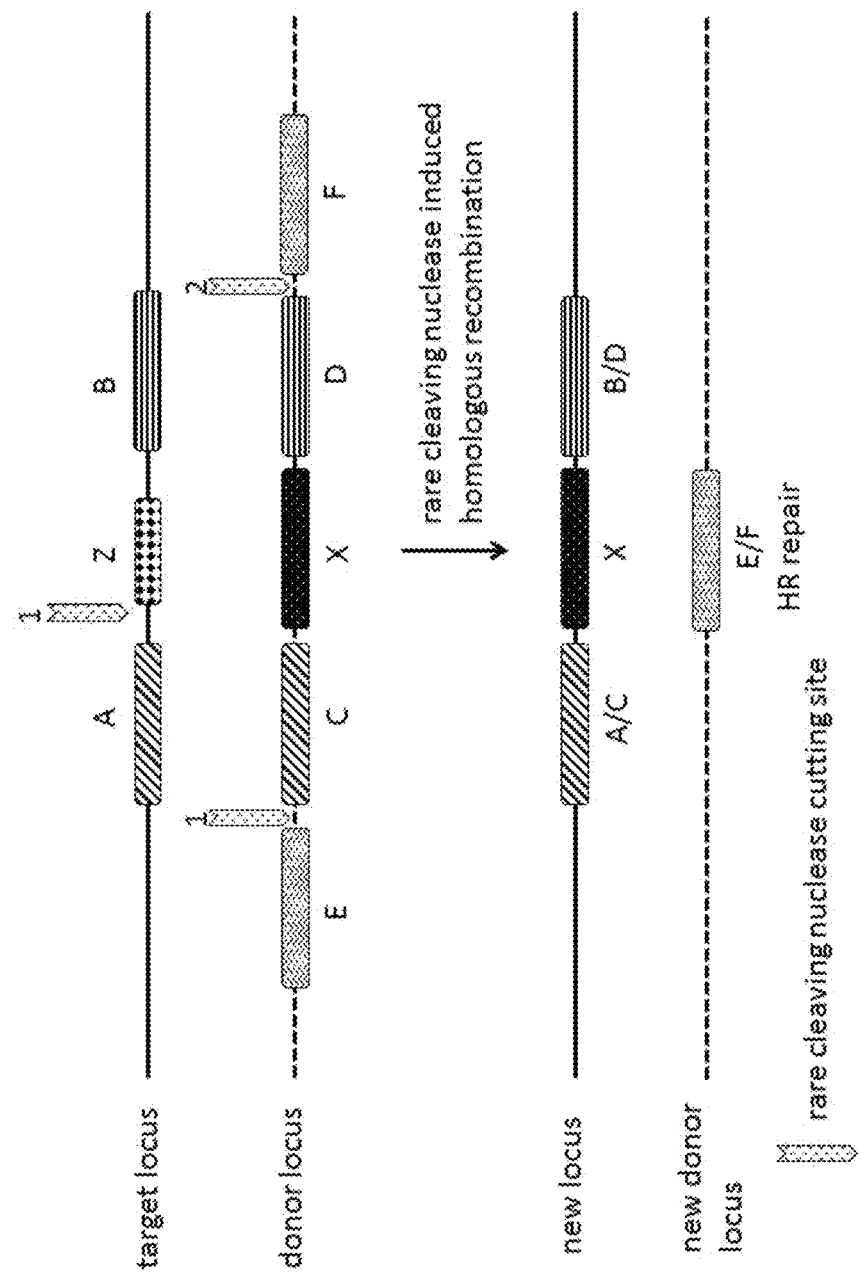
FIG. 3 depicts a very similar design as FIG. 1, meaning that all symbols used have the same meaning as described for FIG. 1. Different to the design of FIG. 1 is that the donor locus comprises additional homologous regions E and F, which have sufficient sequence similarity to allow for DNA repair via homologous recombination (HR) between each other, resulting in a region E/F of the new donor locus.
Figure 4:
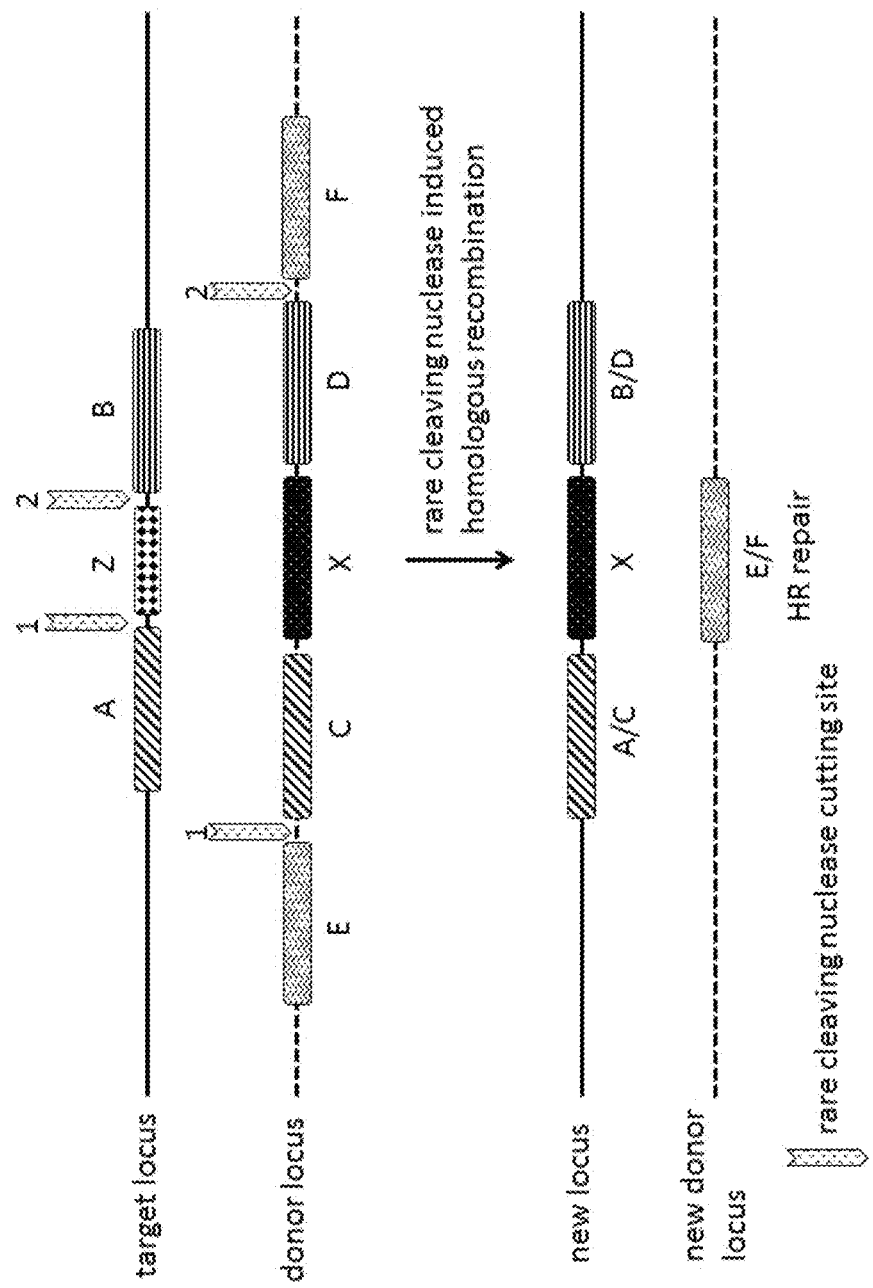
FIG. 4 depicts a very similar design as FIG. 3, meaning that all symbols used have the same meaning as described for FIG. 1. Different to the design of FIG. 3 is that the target locus of FIG. 4 comprises two rare cleaving nuclease cutting sites, flanking region Z.
Figure 5:
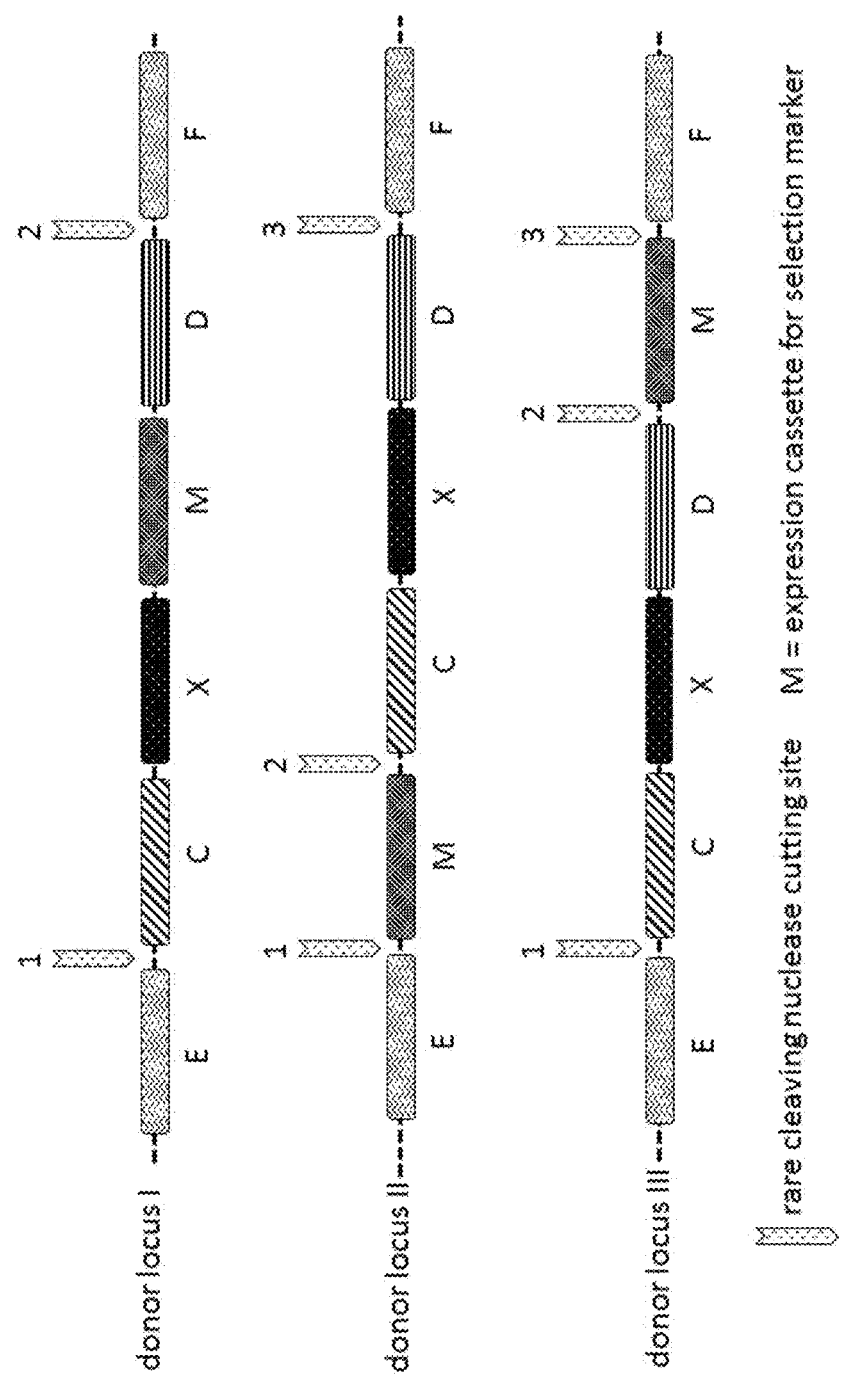
FIG. 5 depicts three examples of alternative designs of a donor locus (donor locus I, donor locus II and donor locus III), which are suited to be combined with any design of a target locus described herein. All three donor loci comprise homologous regions C and D, which allow for homologous recombination with respective homologous regions A and B of a target locus, as well as homologous regions E and F, which have sufficient sequence similarity to allow for homologous recombination between each other as described for homologous regions E and F of FIG. 3. All three donor loci comprise also an expression cassette for a selection marker (M) as well as one, two, three or more rare cleaving nuclease cutting sites. The rare cleaving nuclease cutting sites being located between homologous region E and homologous region F, but not between homologous region C and homologous region D. For example, donor locus I comprises at least one rare cleaving nuclease cutting site, but preferably at least two rare cleaving nuclease cutting sites, being located between homologous regions E and C or homologous regions D and F or between homologous regions E and C and homologous regions D and F. For example, donor locus II comprises at least one, but preferably at least two or three rare cleaving nuclease cutting sites, being located between homologous regions E and M, M and C or D and F. Preferably being located between E and M, M and C and D and F. Donor locus III has a very similar design to donor locus II, but has a different location of the expression cassette for a selection marker, which is located between homologous regions E and F and is preferably flanked by one or two rare cleaving nuclease cutting sites. Donor locus III comprises at least one, but preferably at least two or three rare cleaving nuclease cutting sites, being located between homologous regions E and C, D and M, or M and F. Preferably being located between E and C, D and M and M and F.
Figure 6:
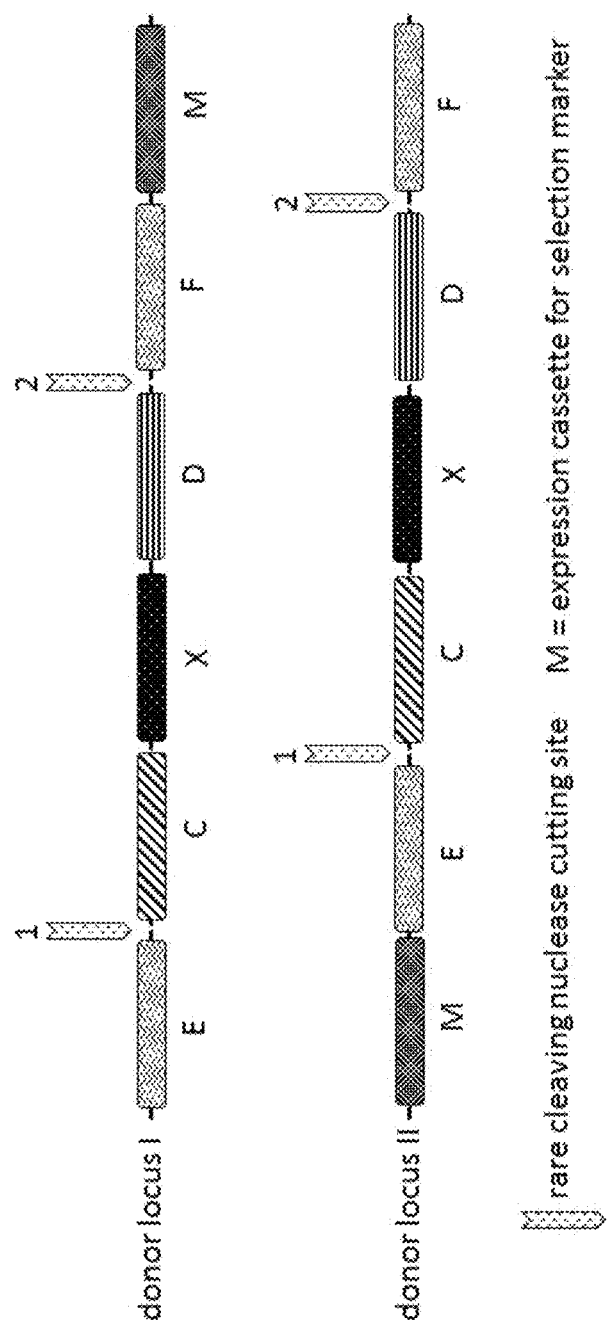
FIG. 6 depicts two further exemplary designs of alternative donor loci, which can be used as the alternative donor loci depicted in FIG. 5.
Figure 7:
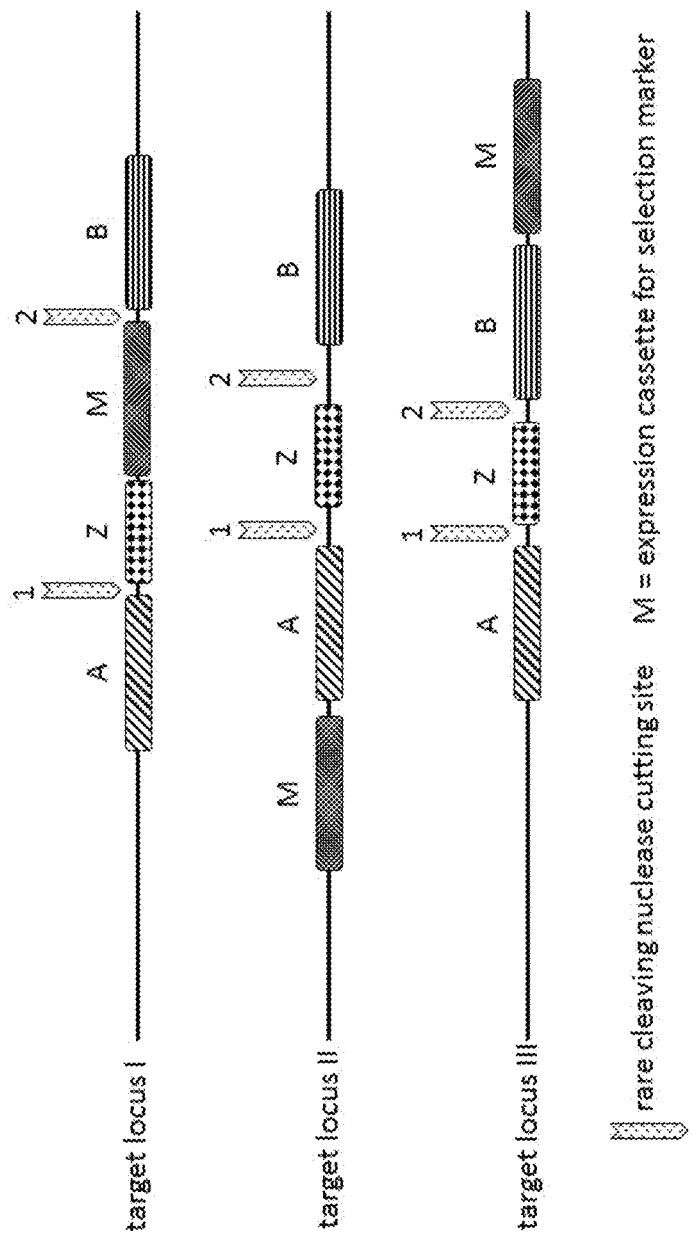
FIG. 7 depicts three different designs of alternative target loci (target locus I, target locus II and target locus III), which can be used in combination with any donor locus described herein. All three target loci comprise homologous regions A and B, which allow for homologous recombination with respective homologous regions C and D of a donor locus, as well as regions Z and an expression cassette for a selection marker (M) as well as rare cleaving nuclease cutting sites. All three target loci comprise at least one rare cleaving nuclease cutting site, preferably two rare cleaving nuclease cutting sites, located between homologous regions A and B. The target loci depicted in FIG. 7 differ by a different location of the expression cassette for a selective marker, which may be located between homologous regions A and B, e.g. between region Z and homologous region B, or between region Z and homologous region A (target locus I) or may be located outside of homologous region A and B e.g. close to homologous region A (target locus II) or close to homologous region B (target locus III).

The term "about" is used herein to mean approximately, roughly, around, or in the region of. When the term "about" is used in conjunction with a numerical range, it modifies that range by extending the boundaries above and below the numerical values-set forth. In general, the term "about" is used herein to modify a numerical value above and below the stated value by a variance of 20 percent up or down (higher or lower), preferably 15 percent, more preferably 10 percent and most preferably 5 percent.

The term "genome" or "genomic DNA" is referring to the heritable genetic information of a host organism. Said genomic DNA comprises the entire genetic material of a cell or an organism, including the DNA of the nucleus (chromosomal DNA), extrachromosomal DNA, and organellar DNA (e.g. of mitochondria and plastids like chloroplasts). Preferably, the terms genome or genomic DNA is referring to the chromosomal DNA of the nucleus.

The term "chromosomal DNA" or "chromosomal DNA sequence" is to be understood as the genomic DNA of the cellular nucleus independent from the cell cycle status. Chromosomal DNA might therefore be organized in chromosomes or chromatids, they might be condensed or uncoiled. An insertion into the chromosomal DNA can be demonstrated and analyzed by various methods known in the art like e.g., polymerase chain reaction (PCR) analysis, Southern blot analysis, fluorescence in situ hybridization (FISH), in situ PCR and next generation sequencing (NGS).

The term "plant" as used herein can, depending on context, be understood to refer to whole plants, plant cells, plant organs, plant seeds, and progeny of the same. The word "plant" also refers to any plant, particularly, to seed plant, and may include, but not limited to, crop plants. Plant parts include, but are not limited to, stems, roots, shoots, fruits, ovules, stamens, leaves, embryos, meristematic regions, callus tissue, gametophytes, sporophytes, pollen, microspores, hypocotyls, cotyledons, anthers, sepals, petals, pollen, seeds and the like.

The term "promoter" refers to regions or sequences located upstream and/or down-stream from the start of transcription and which are involved in recognition and binding of RNA polymerase and other proteins to initiate transcription.

The term "close to" when used in reference to the location of one element of a target locus or a donor locus in respect to another element of a target locus or a donor locus, e.g. a rare cleaving nuclease cutting site, a homologous region, a region Z or an expression cassette for a marker gene or rare cleaving nuclease or any other element of a target locus or donor locus, means a distance of not more than 50 bp, 100 bp, 200 bp, 300 bp, 400 bp, 500 bp, 600 bp, 700 bp, 800 bp, 900 bp, 1000 bp, 2000 bp, 3000 bp, 4000 bp, 5000 bp, 6000 bp 7000 bp, 8000 bp, 9000 bp, or not more than 10000 bp. Preferably it means a distance of not more than 50 bp, 100 bp, 200 bp, 300 bp, 400 bp, 500 bp, 600 bp, 700 bp, 800 bp, 900 bp, 1000 bp.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e. g. a genetically engineered coding sequence or an allele from a different ecotype or variety).

"Transgene", "transgenic" or "recombinant" refers to a polynucleotide manipulated by man or a copy or complement of a polynucleotide manipulated by man. For instance, a transgenic expression cassette comprising a promoter operably linked to a second polynucleotide may include a promoter that is heterologous to the second polynucleotide as the result of manipulation by man (e.g., by methods described in Sambrook et al., Molecular Cloning-A Laboratory Manual, Cold Spring Harbor Laboratory, Cold Spring Harbor, N.Y., (1989) or Current Protocols in Molecular Biology Volumes 1-3, John Wiley & Sons, Inc. (1994-1998)) of an isolated nucleic acid comprising the expression cassette. In another example, a recombinant expression cassette may comprise polynucleotides combined in such a way that the polynucleotides are extremely unlikely to be found in nature. For instance, restriction sites or plasmid vector sequences manipulated by man may flank or separate the promoter from the second polynucleotide. One of skill will recognize that polynucleotides can be manipulated in many ways and are not limited to the examples above.

A polynucleotide "exogenous to" an individual organism is a polynucleotide which is introduced into the organism by any means other than by a sexual cross.

The term "expression cassette"—for example when referring to the expression cassette for the sequence specific DNA-endonuclease—means those constructions in which the DNA to be expressed is linked operably to at least one genetic control element which enables or regulates its expression (i.e. transcription and/or translation). Here, expression may be for example stable or transient, constitutive or inducible.

The terms "operable linkage" or "operably linked" are generally understood as meaning an arrangement in which a genetic control sequence is capable of exerting its function with regard to a nucleic acid sequence, for example while encoding a sequence specific DNA-endonuclease. Function, in this context, may mean for example control of the expression, i.e. transcription and/or translation, of the nucleic acid sequence, for example one encoding a sequence specific DNA-endonuclease. Control, in this context, encompasses for example initiating, increasing, governing or suppressing the expression, i.e. transcription and, if appropriate, translation. Controlling, in turn, may be, for example, tissue- and/or time-specific. It may also be inducible, for example by certain chemicals, stress, pathogens and the like. Preferably, operable linkage is understood as meaning for example the sequential arrangement of a promoter, of the nucleic acid sequence to be expressed—for example one encoding a sequence specific DNA-endonuclease—and, if appropriate, further regulatory elements such as, for example, a terminator, in such a way that each of the regulatory elements can fulfill its function when the nucleic acid sequence—for example one encoding a sequence specific DNA-endonuclease—is expressed. An operably linkage does not necessarily require a direct linkage in the chemical sense. Genetic control sequences such as, for example, enhancer sequences are also capable of exerting their function on the target sequence from positions located at a distance or indeed other DNA molecules. Preferred arrangements are those in which the nucleic acid sequence to be expressed—for example one encoding a sequence specific DNA-endonuclease—is positioned after a sequence acting as promoter so that the two sequences are linked covalently to one another. The distance between the promoter sequence and the nucleic acid sequence—for example one encoding a sequence specific DNA-endonuclease—is preferably less than 200 base pairs, especially preferably less than 100 base pairs, very especially preferably less than 50 base pairs. The skilled worker is familiar with a variety of ways in order to obtain such an expression cassette. References for customary recombination and cloning techniques are given below. However, an expression cassette may also be constructed in such a way that the nucleic acid sequence to be expressed (for example one encoding a selection marker, a rare cleaving nuclease, or a HR modifying sequence) is brought under the control of an endogenous genetic control element, for example an endogenous promoter, for example by means of homologous recombination or else by random insertion. Such constructs are likewise understood as being expression cassettes for the purposes of the invention.

The term "homologous region" as used herein for example to describe homologous regions A, B, C, D, E, F, G, H, I, J, or K, is not limited to a given polynucleotide sequence, but may comprise parts of, or complete sequences of promoters, coding regions, terminator sequences, enhancer sequences, matrix-attachment regions, or one or more expression cassettes. The term "homologous region" gains meaning in combination with another "homologous region" by sharing sufficient sequence identity to be able to recombine via homologous recombination with such other homologous region. Such pairs of homologous regions are described below and comprise for example homologous regions A and C, B and D, E and F, B/D and G, H and I or J and K. Because a homologous region is not limited by any structural features other than its sufficient sequence identity to another homologous region, it may be that a given sequence may be a homologous region A to a homologous region C, but may at the same time be a homologous region E to a homologous region F. Thus, a homologous region of a donor locus has to be understood in context to another homologous region of a target locus or another sequence of the same donor locus, for example a given sequence may be a homologous region C of a donor locus if used in combination with a target locus comprising a homologous region A.

The term "have sufficient sequence identity to be able to recombine via homologous recombination" or "having sufficient sequence identity to be able to recombine via homologous recombination" when used in reference to two homologous regions e.g. a homologous region A and C, B and D, E and F, B/D and G, H and I or J and K, means that those two homologous regions share a sequence identity of at least 70%, preferably 80%, by preference at least 90%, especially preferably at least 95%, very especially preferably at least 99%, most preferably 100%, over a sufficient length. Wherein a sufficient length means a length of at least 100 base pairs, at least 250 base pairs, at least 500 base pairs, at least 800 bp, at least 1000 bp, at least 2000 bp. Also preferred is a length of more than 2000 bp up to 10000 bp. It is preferred to use shorter length for recombinant sequences, preferably length of at least 100 bp to 2000 bp, preferably 250 bp to 2000 bp, more preferred of at least 500 bp to 1500 bp.

The term "sequence identity" between two nucleic acid sequences is understood as meaning the percent identity of the nucleic acid sequence over in each case the entire sequence length which is calculated by alignment with the aid of the program algorithm GAP (Wisconsin Package Version 10.0, University of Wisconsin, Genetics Computer Group (GCG), Madison, USA), setting the following parameters:
Gap Weight: 12 Length Weight: 4
Average Match: 2,912 Average Mismatch:—2,003

DETAILED DESCRIPTION OF PREFERRED EMBODIMENTS

The invention described herein provides methods as well as donor loci, suited to modify target loci in a plant genome, as well as target loci especially suited to be modified by the methods and donor loci of the invention. The modification of the target locus or the target loci is supported by the use of one or more rare cleaving nucleases, which cut or nick rare cleaving nuclease cutting sites, being located at or close by the target and donor loci. After at least one rare cleaving nuclease cutting site of the target and/or donor loci has been cut or nicked by the rare cleaving nuclease, the target locus is modified via homologous recombination between at least one homologous region A of the target locus with at least one homologous region C of the donor locus and homologous recombination between at least one homologous region B of the target locus and a at least one homologous region D of the donor locus, thereby exchanging the former nucleotide sequence Z being located between the least one homologous region A and at least one homologous region B of the target locus, with a nucleotide sequence X located between at least one homologous region C and at least one homologous region D of the donor locus.

In one embodiment of the invention, the at least one target loci and the at least one donor loci are comprised in one cell and have been combined via crossing of two plants, one plant comprising at least one target locus and one plant comprising at least one donor locus, before such cell is provided with at least one rare cleaving nuclease, being able to cut or nick at least one rare cleaving nuclease cutting site comprised in at least one target and at least one donor locus.

In another embodiment of the invention, the plant cell comprising at least one target locus is provided with at least one donor locus via crossing with a plant cell comprising the at least one donor locus, or via transformation with a polynucleotide construct comprising the at least one donor locus, wherein the at least one target loci comprise a nucleotide sequence Z which is flanked by at least one rare cleaving nuclease cutting site located between nucleotide sequence Z and homologous region A and at least one rare cleaving nuclease cutting site located between nucleotide sequence Z and homologous region B.

Accordingly, the invention encompasses a method for modifying a target locus in a plant cell, comprising the following steps: a) providing a plant cell comprising at least one target locus comprising at least one homologous region A and at least one homologous region B and comprising at least one nucleotide sequence Z located between at least one homologous region A and at least one homologous region B and comprising at least one donor locus comprising at least one homologous region C and at least one homologous region D, wherein homologous region(s) A and homologous region(s) C have sufficient sequence identity to be able to recombine via homologous recombination and homologous region(s) B and homologous region(s) D have sufficient sequence identity to be able to recombine via homologous recombination and wherein the at least one target locus and the at least one donor locus are integrated in the chromosomal DNA of the plant cell and wherein the at least one target locus comprises one or more rare cleaving nuclease cutting site(s) located between at least one homologous region A and at least one homologous region B and wherein the at least one donor locus comprises one or more rare cleaving nuclease cutting site(s) flanking a nucleotide sequence of the donor locus comprising at least one homologous region C and at least one homologous region D, b) providing the plant cell of step a) with at least one rare cleaving nuclease being able to nick or cut at least one rare cleaving nuclease cutting site located in the at least one target locus or located in the at least one donor locus or located in the at least one target locus and at least one donor locus, c) allowing the rare cleaving nuclease to nick or cut at least one of the rare cleaving cutting sites of step a), d) allowing homologous region A and homologous region C of step a) to recombine and allowing homologous region B and homologous region D of step a) to recombine.

The invention encompasses a further method for modifying a target locus in a plant cell, comprising the following steps: a) providing a plant cell comprising at least one target locus integrated in the chromosomal DNA of the plant cell wherein the at least one target locus comprises at least one homologous region A and at least one homologous region B and comprising at least one nucleotide sequence Z located between at least one homologous region A and at least one homologous region B and wherein nucleotide sequence Z is flanked by at least one rare cleaving nuclease cutting site on each side of nucleotide sequence Z, and b) providing the plant cell of step a) with at least one donor locus comprising at least one homologous region C and at least one homologous region D and comprising at least one nucleotide sequence X located between at least one homologous region C and at least one homologous region D, wherein homologous region(s) A and homologous region(s) C have sufficient sequence identity to be able to recombine via homologous recombination and homologous region(s) B and homologous region(s) D have sufficient sequence identity to be able to recombine via homologous recombination and wherein the at least one donor locus comprises one or more rare cleaving nuclease cutting site(s) flanking a nucleotide sequence of the donor locus comprising at least one homologous region C and at least one homologous region D, c) providing the plant cell of step a) or step b) with at least one rare cleaving nuclease being able to nick or cut at least one rare cleaving nuclease cutting site located in the at least one target locus or located in the at least one donor locus or located in the at least one target locus and at least one donor locus, d) allowing the rare cleaving nuclease to nick or cut at least one of the rare cleaving cutting sites of step a) and step b), e) allowing homologous region A and homologous region C of step a) and step b) to recombine and allowing homologous region B and homologous region D of step a) and step b) to recombine.

The plant cell of the methods of the invention can be any plant cell. Preferably the plant cell is a plant cell which can either directly or via its descendants contribute to form a seed embryo, either by being a cell in tissue culture having the potential to be regenerated to a fertile plant, or by being part of a plant tissue which will potentially give rise to cells able to form a seed embryo, such as, but not excluding others: cells of primary or secondary meristems, egg-cells, egg mother cells, pollen cells, pollen mother cells, zygotic cells.

The plant cell can be of any plant species. Preferred plant species are selected from the group consisting of maize, wheat, barley, sorghum, rye, triticale, rice, sugarcane, citrus trees, pineapple, coconut, banana, coffee, tea, tobacco, sunflower, pea, alfalfa, soybean, carrot, celery, tomato, potato, cotton, tobacco, eggplant, pepper, oilseed rape, canola, beet, cabbage, cauliflower, broccoli, lettuce, Lotus sp., *Medicago truncatula*, prerennial grass, ryegrass, castor bean, Jatropha spec. and *Arabidopsis thaliana*. In another embodiment the plant can be from a genus selected from the group consisting of citrus trees, pineapple, coffee, tea, tobacco, sunflower, pea, alfalfa, soybean, carrot, celery, tomato, potato, cotton, tobacco, eggplant, pepper, oilseed rape, canola, beet, cabbage, cauliflower, broccoli, lettuce, Lotus sp., *Medicago truncatula* and *Arabidopsis thaliana*. In another embodiment the plant can be from a genus selected from the group consisting of, tobacco, sunflower, pea, alfalfa, soybean, tomato, potato, cotton, tobacco, eggplant, pepper, oilseed rape, canola, beet, cabbage, cauliflower, broccoli, lettuce, Lotus sp., *Medicago truncatula* and *Arabidopsis thaliana*. In another embodiment the plant cell can be from a genus selected from the group consisting of maize, wheat, barley, sorghum, rye, triticale, rice, sugarcane, pineapple, coconut, banana, perennial grass and ryegrass.

Preferably, the plant cell used in the methods of the invention have an enhanced capacity to perform homologous recombination. Examples for such plant cells are plant cells overexpressing a bacterial RecA gene or a yeast Rad54 gene as for example disclosed in U.S. Pat. No. 6,583,336 and Shaked et al. 2005; High-frequency gene targeting in *Arabidopsis* plants expressing the yeast RAD54 gene; PNAS, Vol. 102, Nr. 34, page 12265 to 12269. In another embodiment of the invention the plant cells have a reduced expression of the AtLIG4 gene or its respective homolog Tanaka et al. 2010; High efficient gene targeting on the AGAMOUS gene in an *Arabidopsis* AtLIG4 mutant; Biochemical and Biophysical Research Communications; Vol. 396, pages 289 to 293.

In another embodiment of the invention, the plant cell has a reduced expression level or a mutation of a gene involved in the NHEJ-repair mechanism, as for example RecQ4 or in the genes being disclosed in WO11/052539, in WO11/078662 or in WO00/12716 and herein included by reference. Genes, including naturally occurring protein coding sequences or recombinant protein coding sequences, as well as Genes expressing naturally occurring or recombinant RNAs, e.g. miRNAs or dsRNAs, which have the capacity to modify the frequency or quality of homologous recombination reactions in plant cells, as for example described above, are also referred to as HR modifying sequences.

The rare cleaving nuclease used in the methods of the invention can be any nuclease which is specific enough to cleave, meaning to nick or cut DNA double strands, only rarely in an eukaryotic genome. For statistical reasons, this limits rare cleaving nucleases to nucleases having a rare cleaving nuclease cutting site of at least 10, at least 14, at least 16, at least 18, at least 20, at least 22, at least 24, at least 26, at least 28, at least 30 or more than 30 base pairs in length.

Rare cleaving nucleases can be found in several different groups of naturally occurring or artificially designed nuclease families. Preferred groups of rare cleaving nucleases are zinc-finger nucleases, TALE-nucleases and homing nucleases, in particular LAGLIDADG endonucleases.

Zinc-finger nucleases are artificially created homo- or heterodimeric nucleases comprising in each monomer an unspecific DNA cleavage domain fused to a DNA binding domain. The unspecific DNA cleavage domain of a monomer usually comprises a half-site of the FoId nuclease, but can in principle comprise any DNA-cleavage domain of an unspecific Type II-endonuclease. The DNA binding domain usually comprises three or more repeats of a zinc-finger DNA binding motive. Each of those repeats has the capacity to bind to three nucleotides and can be mutated to bind virtually any combination of three nucleotides, so that the entire zinc-finger nuclease can be designed to bind to any nucleotide sequence. Many different zinc-finger nucleases have been created. Examples of zinc-finger nucleases as well as methods how to design and use them can be found e.g. in WO0027878, WO02057293, WO03089452, WO07139898, WO08021207 and WO08076290.

TALE-nucleases are very similar in design to the zinc-finger nucleases, meaning that they are also artificially created homo- or heterodimeric nucleases comprising in each monomer an unspecific DNA cleavage domain fused to a DNA binding domain. The unspecific DNA cleavage domain of a monomer usually comprises a half-site of the FoId nuclease, but can in principle comprise any DNA-cleavage domain of an unspecific Type II-endonuclease.

The DNA binding domain usually comprises several repeat units derived from a transcription activator-like (TAL) effector. The term "repeat unit" is used to describe the modular portion of a repeat domain of a TAL effector, or an artificial version thereof, that contains one or two amino acids in positions 12 and 13 of the amino acid sequence of a repeat unit that determine recognition of a base pair in a target DNA sequence that such amino acids confer recognition of, as follows:

HD for recognition of C/G; NI for recognition of A/T; NG for recognition of T/A; NS for recognition of C/G or NT or T/A or G/C; NN for recognition of G/C or A/T; IG for recognition of T/A; N for recognition of C/G; HG for recognition of C/G or T/A; H for recognition of T/A; and NK for recognition of G/C (the amino acids H, D, I, G, S, K are described in one-letter code, whereby A, T, C, G refer to the DNA base pairs recognized by the amino acids).

The number of repeat units to be used in a repeat domain can be ascertained by one skilled in the art by routine experimentation. The repeat units do not have to be complete repeat units, as repeat units of half the size can be used.

A typical consensus sequence of a repeat unit with 34 amino acids (in one-letter code) is shown below:

```
                                            (SEQ ID NO: 1)
     LTPEQVVAIASNGGGKQALETVQRLLPVLCQAHG
```

A further consensus sequence for a repeat unit with 35 amino acids (in one-letter code) is as follows:

```
                                            (SEQ ID NO: 2)
     LTPEQVVAIASNGGGKQALETVQRLLPVLCQAPHD
```

It is possible to use a naturally occurring combinations of repeat units, naturally occurring proteins having combinations of repeat units are for example: AvBs3, Hax2, Hax3 and Hax4, which bind to their naturally occurring DNA binding site sequences.

The respective DNA binding site sequences are:

```
     AvBs3:
                                            (SEQ ID NO: 3)
     5'-TCTNTAAACCTNNCCCTCT-3',
     of

Hax2:
                                            (SEQ ID NO: 4)
     5'-TGTTATTCTCACACTCTCCTTAT-3',
     of,

Hax3:
                                            (SEQ ID NO: 5)
     5'-TACACCCNNNCAT-3'
     and Hax4:
                                            (SEQ ID NO: 6)
     5'-TACCTNNACTANATAT-3'
```

However, it is also possible to design new combinations of repeat units in order to create new DNA binding domains for any given DNA binding site sequence, which in turn opens the possibility to create new TALE nucleases which can recognize any given nucleotide sequence as their rare cleaving nuclease cutting site.

Examples of artificially created combinations of repeat units and artificially created TALE nucleases can be found for example in WO2010/079430, WO11072246 and WO11072246.

Another example of rare cleaving nucleases, which are suitable to be used in the methods of the invention are homing nucleases. Important groups of homing endonucleases are GIY-YIG-, His-Cys box-, HNH- or LAGLI-DADG-endonucleases. GIY-YIG endonucleases have a GIY-YIG module of 70 to 100 amino acids length, which includes four or five conserved sequence motifs with four invariant residues (Van Roey et al (2002), Nature Struct. Biol. 9:806 to 811). His-Cys box endonucleases comprise a highly conserved sequence of histidines and cysteines over a region of several hundred amino acid residues. The HNH-endonucleases are defined by sequence motifs containing two pairs of conserved histidines surrounded by asparagine residues. Further information on His-Cys box- and HNH endonucleases is provided by Chevalier et al. (2001), Nucleic Acids Res. 29(18): 3757 to 3774). LAGLIDADG endonucleases can be found in the genomes of algae, fungi, yeasts, protozoan, chloroplasts, mitochondria, bacteria and archaea. LAGLIDADG endonucleases comprise at least one conserved LAGLIDADG motif (SEQ ID NO: 26). The name of the LAGLIDADG motif (SEQ ID NO: 26) is based on a characteristic amino acid sequence appearing in all LAGLI-DADG endonucleases. The term LAGLIDADG is an acronym of this amino acid sequence according to the one-letter-code as described in the STANDARD ST.25 i.e. the standard adopted by the PCIPI Executive Coordination Committee for the presentation of nucleotide and amino acid sequence listings in patent applications.

However, LAGLIDADG motifs (SEQ ID NO: 26) are not fully conserved in all LAGLIDADG endonucleases, (see for example Chevalier et al. (2001), Nucleic Acids Res. 29(18): 3757 to 3774, or Dal-gaard et al. (1997), Nucleic Acids Res. 25(22): 4626 to 4638), so that some LAGLIDADG endonucleases comprise some amino acid changes in their LAGLIDADG motif (SEQ ID NO: 26).

LAGLIDADG endonucleases comprising only one LAGLIDADG motif (SEQ ID NO: 26) usually act as homo- or heterodimers. LAGLIDADG endonucleases comprising two LAGLIDADG motifs (SEQ ID NO: 26) act as monomers and comprise usually a pseudo-dimeric structure.

LAGLIDADG endonucleases can be found in nature, but it is also possible to design new LAGLIDADG endonucleases (so called engineered endonucleases) in order to enhance their cleavage activity or their binding specificity or to change the sequence of their rare nuclease cutting sites to any given nucleotide sequence.

Preferred LAGLIDADG endonuclease are selected from the group comprising: I-SceI, I-CreI, I-MsoI, I-CeuI, I-DmoI, I-AniI and PI-SceI, including their engineered variants.

Numerous examples of engineered endonucleases, as well as their respective rare cleaving nuclease cutting sites are known in the art and are disclosed for example in: WO 2005/105989, WO 2007/034262, WO 2007/047859, WO 2007/093918, WO 2008/093249, WO 2008/102198, WO 2008/152524, WO 2009/001159, WO 2009/059195, WO 2009/076292, WO 2009/114321, WO 2009/134714 and WO 10/001189.

Engineered endonuclease variants of I-AnII having high enzymatic activity can be found in Takeuchi et al., Nucleic Acid Res. (2009), 73(3): 877 to 890. Preferred engineered endonuclease variants of I-AnII, comprise the following mutations: F13Y and S111Y, or F13Y, S111Y and K222R, or F13Y, I55V, F9II, S92T and S111Y.

Because of the huge variety of available rare cleaving nucleases as well as the possibility to produce particular mutants and engineered variants of naturally occurring rare cleaving nucleases, basically any given polynucleotide sequence may be a rare cleaving nuclease cutting site if the respective rare cleaving nuclease is selected or created. Thus, the term "rare cleaving nuclease cutting site" has to be understood in reference to a particular rare cleaving nuclease.

Examples of polynucleotide sequences which can be bound and cut by endonucleases, i.e. which represent a DNA recognition sequence or DNA recognition site for this endonuclease, are described in Table 1: the letter N represents any nucleotide, and can be replaced by A, T, G or C).

TABLE 1

| Endo-nuclease | Organism of origin | DNA recognition sequence |
|---|---|---|
| I-SceI | S. cerevisiae | 5'-TAGGGATAACAGGG TAAT-3' (SEQ ID NO: 7) |
| I-CreI | Chlamydomonas reinhardtii | 5'-CAAAACGTCGTGAGAC AGTTTC-3' (SEQ ID NO: 8) |
| I-CeuI | Chlamydomonas eugametos | 5'-ATAACGGTCCTAAGGT AGCGAA-3' (SEQ ID NO: 9) |
| I-DmoI | Desulfurococcus mobilis | 5'-ATGCCTTGCCGGGTAA GTTCCGGCGCGCAT-3' (SEQ ID NO: 10) |
| I-MsoI | Monomastix spec. | 5'-CAGAACGTCGTGAGAC AGTTCC-3' (SEQ ID NO: 11) |
| PI-PsiI | S. cerrevisiae | 5'-ATCTATGTCGGGTGCG GAGAAAGAGGTAAT-3' (SEQ ID NO: 12) |
| I-AniI | Aspergillus nidulans | 5'-GCGCGCTGAGGAGGTT TCTCTGTAAAGCGCA-3' (SEQ ID NO: 13) |

Further important rare cleaving nucleases, as well as their respective rare cleaving nuclease cutting sites are disclosed for example in: Shukla et al. "Precise genome modification in the crop species *Zea mays* using zinc-finger nucleases"; nature, 2009; Vol 459, pages 437 to 441, in Townsend et al. "High-frequency modification of plant genes using engineered zinc-finger nucleases"; nature, 2009; Vol 459, pages 442 to 445, in Barzel et al. "Native homing endonucleases can target conserved genes in humans and in animal models"; Nucleic Acids Research, 2011, Vol. 39, No. 15, pages 6646 to 6659, in Curtin et al, "Targeted Mutagenesis of Duplicated Genes in Soybean with Zinc-Finger Nucleases"; Plant Physiology, June 2011, Vol. 156, pp. 466-473, as well as in EP2018434, in WO09042164, WO09114321, in WO10093966, WO11072246, in WO03089452, in WO09042164, and in WO11072246, all herein included by reference.

Rare cutting endonucleases may not have stringently-defined DNA recognition sequences, so that single base changes may not abolish cleavage but may reduce its efficiency to variable extents. A DNA recognition sequence listed herein for a given endonuclease represents only one site that is known to be recognized and cleaved.

Examples for deviations of a DNA recognition site are for example disclosed in Chevelier et al. (2003), J. Mol. Biol. 329, 253 to 269, in Marcaida et al. (2008), PNAS, 105 (44), 16888 to 16893 and in the Supporting Information to Marcaida et al. 10.1073/pnas.0804795105, in Doyon et al. (2006), J. AM. CHEM. SOC. 128, 2477 to 2484, in Argast et al, (1998), J. Mol. Biol. 280, 345 to 353, in Spiegel et al. (2006), Structure, 14, 869 to 880, in Posey et al. (2004), Nucl. Acids Res. 32 (13), 3947 to 3956, or in Chen et al. (2009), Protein Engineering, Design & Selection, 22 (4), 249 to 256.

It may therefore be possible to identify a naturally occurring endonuclease having a predetermined polynucleotide sequence as a DNA recognition sequence.

Methods to identify naturally occurring endonucleases, their genes and their DNA recognition sequences are disclosed for example in WO 2009/101625.

The cleavage specificity or respectively its degeneration of its DNA recognition sequence can be quantified by testing its activity on different substrates. Suitable in vivo techniques are for example disclosed in WO09074873.

Alternatively, in vitro tests can be used, for example by employing labeled polynucleotides spotted on arrays, wherein different spots comprise essentially only polynucleotides of a particular sequence, which differs from the polynucleotides of different spots and which may or may not be DNA recognition sequences of the endonuclease to be tested for its activity. A similar technique is disclosed for example in US 2009/0197775.

The term rare cleaving nucleases does also comprise further variants of the nucleases described above, e.g. a combination of a Type II-endonuclease domain with an inactive LAGLIDADG endonuclease as DNA binding domain as for example disclosed in WO09134714, or a combination of a LAGLIDADG endonuclease and a glucocorticoid receptor domain as for example disclosed in WO07135022.

Further examples of combinations of LAGLIDADG endonucleases and heterolog DNA binding domains (chimeric endonucleases) can be found for example in WO11064751, WO11064736 and WO11064750.

Further variants of rare cleaving nucleases are mutants of rare cleaving nucleases which do not produce a DNA double strand break, but cut only one DNA strand thereby producing a DNA single strand break, which is called a nicking activity.

Rare cleaving nucleases which have nicking activity or which nick DNA, respectively, are disclosed for example in WO10093966.

The rare cutting nuclease is usually selected in such a way, that the rare cutting nuclease provided to the plant cells is able to nick or cut at least one nuclease cutting site located in the at least one target locus or not more than about 100 bp, 200 bp, 300 bp, 500 bp, 700 bp, 1000 bp, 1500 bp, 2000 bp, 3000 bp, 4000 bp, 5000 bp, 6000 bp, 7000 bp, 8000 bp, 9000 bp or 10000 bp apart from the target locus. Preferably the rare cutting nuclease is selected in such a way, that it is able to nick or cut at least one nuclease cutting site being located in the at least one target locus.

It is even more preferred to select the rare cutting nuclease in such a way, that it is able to nick or cut at least two rare cleaving nuclease cutting sites located in the at least one target locus, or at least two rare cleaving nuclease cutting sites located in the at least one donor locus, or at least two rare cleaving nuclease cutting sites located in the at least one target locus and at least one rare cleaving nuclease cutting sites located in the at least one donor locus, or at least one rare cleaving nuclease cutting site located in the at least one target locus and at least two rare cleaving nuclease cutting sites located in the at least one donor locus, or at least two rare cleaving nuclease cutting sites located in the at least one target locus and at least two rare cleaving nuclease cutting sites located in the at least one donor locus.

Most preferred, the rare cutting nuclease is selected in order to be able to nick or cut at least two rare cleaving nuclease cutting sites located in the at least one target locus and at least two rare cleaving nuclease cutting sites located in the at least one donor locus.

It is possible to provide the rare cutting nuclease in several alternative ways to the plant cell used in the method.

The rare cleaving nuclease can be provided by providing the plant cell or crossing or fusing a plant cell comprising an expression cassette being able to express the rare cutting nuclease with a plant cell comprising the at least one target locus, or comprising the at least one donor locus, or preferably comprising the at least one target locus and comprising the at least one donor locus.

The cross can be performed in such a way that either the pollen cells or the egg cells comprise the expression cassette for the rare cleaving nuclease.

The rare cleaving nuclease can be expressed from the expression cassette directly in the resulting zygote of the cross, or at a later stage e.g. in cells of the developing plant embryo or stem or callus meristem or flower meristem of the resulting plant. This can be achieved by driving the expression of the rare cutting nuclease via a constitutive, tissue specific or inducible promoter.

In a further embodiment of the invention, the rare cleaving nuclease can be provided by fusing plant cells e.g. via electro-fusion. By choosing a constitutive, tissue specific or inducible promoter to drive the expression of the rare cleaving nuclease the rare cleaving nuclease can be directed to be expressed directly in the resulting fusion cell, or at a later stage during regeneration of the fusion cell to a complete fertile plant.

The rare cleaving nuclease(s) can also be provided by transforming a cell comprising the at least one target locus and the at least one donor locus with an expression cassette being able to express the rare cleaving nuclease. Preferably the expression cassette being able to express the rare cleaving nuclease comprises an intron sequence in the region coding for the nuclease in order to avoid unwanted expression in cells other than plant cells, e.g. in Agrobacteria. The transformation can be either transient or stable. In case of a transient expression, it is important to drive the expression of the rare cleaving nuclease via a promoter being active in the cell type used for the transient expression. In case the transformation is stable other promoters can be selected e.g. promoters which drive the expression of the rare cleaving nuclease at a later stage during plant regeneration or in a certain tissue or after induction of the promoter.

A further method to provide the rare cleaving nuclease is via infection with a viral vector comprising an expression cassette driving the expression of the rare cleaving nuclease in a cell being infected with the viral vector and being able either to provide cells for a floral meristem or being able to be regenerated to a fertile plant. Suitable viral vectors are for example disclosed in WO09130695.

In a further embodiment of the invention, the rare cleaving nuclease is provided via introduction of mRNA coding for at least one rare cleaving nuclease into a cell comprising the at least one target locus and comprising the at least one donor locus.

In an even further embodiment of the invention, the rare cleaving nuclease is introduced via particle bombardment or bacterial Sec III or SecIV secretion systems into a cell comprising the at least one target locus and comprising the at least one donor locus. Methods to use bacterial Sec III or SecIV secretion systems to transfer proteins from a bacterial cell to plant cells are disclosed for example in WO0002996, WO0189283 and WO05085417. Another way to provide the plant cell comprising the at least one target locus and comprising the at least one donor locus with the rare cleaving nuclease is via providing the rare cleaving nuclease with one or more peptides being able to transfer proteins trough biological membranes. Such peptides are disclosed of example in WO0058488.

In a further embodiment of the invention two different rare cleaving nucleases are provided to the cell comprising the at least one target locus and comprising the at least one donor locus, wherein one of those rare cleaving nucleases is able to nick or cut at least one rare cleaving nuclease cutting sites in the at least one target locus and the other rare cleaving nuclease is able to nick or cut at least one rare cleaving nuclease cutting site of the at least one donor locus.

In a further embodiment of the invention, the at least one target locus is provided together with at least one rare cleaving nuclease, wherein the at least one rare cleaving nuclease is able to cleave at least one rare cleaving nuclease cutting site located in the at least one donor locus, but not being able to cleave a rare cleaving nuclease cutting site located in the at least one target locus.

In another embodiment of the invention, the donor locus is provided together with at least one rare cleaving nuclease being able to cleave at least one rare cleaving nuclease cutting site located in the at least one target locus, but not being able to cleave a rare cleaving nuclease cutting site located in the at least one donor locus.

In an even further embodiment of the invention the at least one target locus is provided together with at least one rare cleaving nuclease, wherein the at least one rare cleaving nuclease is able to cleave at least one rare cleaving nuclease cutting site located in the at least one donor locus, but not being able to cleave a rare cleaving nuclease cutting site located in the at least one target locus and the donor locus is provided together with at least one rare cleaving nuclease being able to cleave at least one rare cleaving nuclease cutting site located in the at least one target locus, but not being able to cleave a rare cleaving nuclease cutting site located in the at least one donor locus.

A preferred promoter to drive the expression of a protein described herein, in particular driving the expression of a rare cleaving nuclease or a selection marker or a HR modifying sequence is, in principle, any promoter that is capable of controlling the expression of genes, in particular foreign genes, in plants.

Preferred promoters are those that enable constitutive expression in plants (Benfey et al. (1989) EMBO J. 8:2195-2202). A promoter that is preferably used is, in particular, a plant promoter or a promoter derived from a plant virus. Especially preferred is the promoter of the cauliflower mosaic virus 35s transcript (Franck et al. (1980) Cell 21:285-294; Odell et al. (1985) Nature 313:810-812; Shewmaker et al. (1985) Virology 140:281-288; Gardner et al. 1986, Plant Mol. Biol. 6, 221-228) or the 19S CaMV promoter (U.S. Pat. No. 5,352,605 and WO 84/02913). It is known that this promoter comprises a variety of recognition sequences for transcriptional effectors that, in their totality, bring about permanent and constitutive expression of the gene introduced (Benfey et al. (1989) EMBO J 8:2195-2202). A further suitable constitutive promoter is the Rubisco small subunit (SSU) promoter (U.S. Pat. No. 4,962,028). A further example of a suitable promoter is the leguminB promoter (GenBank Acc.-No.: X03677). Further preferred constitutive promoters are, for example, the *Agrobacterium* nopaline synthase promoter, the TR dual promoter, the *Agrobacterium* OCS (octopine synthase) promoter, the ubiquitin promoter (Holtorf S et al. (1995) Plant Mol Biol 29:637-649), the promoters of the vacuolar ATPase subunits, or the promoter of a wheat proline-rich protein (WO 91/13991)

Equally preferred promoters are pollen-specific promoters such as, for example, the promoter of the *B. campestris* bgpl gene (GenBank Acc.-No: X68210; Xu H et al. (1993) Mol Gen Genet 239(1-2):58-65; WO 94/13809), of the *Oryza sativa* ory s 1 gene (GenBank Acc.-No.: AJ012760; Xu H et al. (1995) Gene 164 (2):255-259), of the pollen-specific maize gene ZM13 (Hamilton D A et al. (1998) Plant Mol Biol 38(4):663-669; U.S. Pat. No. 5,086,169), and of the *Brassica napus* gene Bp10 (GenBank Acc.-No.: X64257; Albani D (1992) Plant J 2(3):331-342; U.S. Pat. No. 6,013, 859).

Other preferred promoters are the Lcg1 promoter for cell-specific expression in the male gametes (WO 99/05281; XU H et al. (1999) Proc. Natl. Acad. Sci. USA Vol. 96:2554-2558) and the promoter of the AtDMC1 gene (Klimyuk V I et al. (1997) Plant J. 11(1):1-14).

Further preferred promoters are inducible, preferably chemically inducible, promoters (Aoyama T and Chua N H (1997) Plant J 11:605-612; Caddick M X et al. (1998) Nat. Biotechnol 16:177-180; Rewiew: Gatz, Annu Rev Plant Physiol Plant Mol Biol 1997, 48:89-108), by means of which the expression of the exogenous gene in the plant can be controlled at a specific point in time. Such promoters, such as, for example, the PRP1 promoter (Ward et al., Plant. Mol. Biol. 22 (1993), 361-366), a salicylic-acid-inducible promoter (WO 95/19443), a benzenesulfonamide-inducible promoter (EP-A-0388186), a tetracyclin-inducible promoter (Gatz et al., (1992) Plant J. 2, 397-404), an abscisic acid-inducible promoter (EP-A 335528), a salicylic acid-inducible promoter (WO 95/19443) or an ethanol- (Salter M G et al. (1998) Plant J. 16:127-132) may likewise be used.

Other preferred promoters are promoters induced by biotic or abiotic stress, such as, for example, the pathogen-inducible promoter of the PRP1 gene (Ward et al., Plant Mol Biol 1993, 22: 361-366), the tomato heat-inducible hsp80 promoter (U.S. Pat. No. 5,187,267), the potato chill-inducible alpha-amylase promoter (WO 96/12814) or the wound-induced pinII promoter (EP375091).

Other preferred promoters are promoters with specificity for the anthers, ovaries, pollen, the meristem, meiotic cells, flowers or seeds.

Also preferred are seed-specific promoters such as, for example, the phaseolin promoter (U.S. Pat. No. 5,504,200, Bustos M M et al., Plant Cell. 1989; 1(9):839-53), the promoter of the 2S albumin gene (Joseffson L G et al. (1987) J Biol Chem 262: 12196-12201), the legumin promoter (Shirsat A et al. (1989) Mol Gen Genet. 215(2):326-331), the USP (unknown seed protein) promoter (Baumlein H et al. (1991) Molecular & General Genetics 225(3):459-67), the napin gene promoter (U.S. Pat. No. 5,608,152; Stalberg K, et al. (1996) L. Planta 199: 515-519), the sucrose binding protein promoter (WO 00/26388) or the legumin B4 promoter (LeB4; Baumlein H et al. (1991) Mol Gen Genet 225:121-128; Baeumlein et al. (1992) Plant Journal 2(2): 233-239; Fiedler U et al. (1995) Biotechnology (NY) 13(10):1090-1093), the Ins *Arabidopsis* oleosin promoter (WO9845461), the *Brassica* Bce4 promoter (WO 91/13980). Further suitable seed-specific promoters are those of the genes encoding the "highmolecular-weight glutenin" (HMWG), gliadin, branching enzyme, ADP-glucose pyrophosphatase (AGPase) or starch synthase. Furthermore preferred promoters are those which enable seed-specific expression in monocots such as maize, barley, wheat, rye, rice and the like. Promoters which may advantageously be employed are the promoter of the Ipt2 or Ipt1 gene (WO 95/15389, WO 95/23230) or the promoters described in WO 99/16890 (promoters of the hordein gene, the glutelin gene, the oryzin gene, the prolamine gene, the gliadin gene, the glutelin gene, the zein gene, the kasirin gene or the secalin gene).

Further suitable promoters are, for example, promoters being specific for tubers, storage roots or roots such as, for example, the class I patatin promoter (B33), the potato cathepsin D inhibitor promoter, the starch synthase (GBSS1) promoter or the sporamin promoter, and fruit-specific promoters such as, for example, the tomato fruit-specific promoter (EP-A 409625). Those promoters are especially suited to drive the expression of the rare cleaving nuclease in plant species which can be propagated via tubers, storage roots or roots, such as, for example, potato, cassava, yam or beets.

Design of Donor Loci:

The methods for targeted integration or targeted exchange of sequences disclosed herein comprise the use of one, two or more donor loci in order to provide polynucleotide sequences to be integrated in one or more target loci. The sequence of a donor locus, which is to be integrated in a target locus or is intended to replace a particular sequence of a target locus, is herein referred to as region X, while the region of the target locus that is exchanged for, i.e. replaced with the region X of the donor locus is herein referred to as region Z.

The region X of a donor locus can, in principle, be any kind of DNA sequence. A region X may be shorter or longer than the respective region Z, and can have a length of one base pair or can range up to several thousand base pairs. For example, in case it is intended to replace one or more base pairs of a region Z with one or only a few base pairs, a region X can be very short. Such short regions X may for example be used to create a point mutation at a target locus. However, in case it is intended to integrate one or more genes at a specific target locus, region X can have a length of several thousand base pairs, while the respective region Z may be comparably short e.g. having a length of one base pair. Typically a region X has a length of 1 to 50000 bps, preferably 1 to 40000 bps, 1 to 30000 bps, 1 to 20000 bps, 1 to 10000 bps, 1 to 9000 bps, 1 to 8000 bps, 1 to 7000 bps, 1 to 6000 bps, 1 to 5000 bps, 1 to 4000 bps, 1 to 3000 bps, 1 to 2000 bps, 1 to 1000 bps or 1 to 500 bps. Region X may comprise polynucleotide sequences, which have the ability to perform a certain function in a plant cell, for example, region X may comprise one or more promoters, coding regions, terminator sequences, enhancer sequences, matrix-attachment regions, or one or more expression cassettes. Alternatively, region X may also comprise parts of those sequences, which only become functional, if integrated at a target locus, for example region X may comprise part of a promoter sequence, which is not functional in plant cells, but becomes functional if integrated in a target locus, which comprises complementing parts of the promoter sequence in which the part of a promoter sequence provided by region X will fulfill its intended function. A person skilled in the art will be able to create further variants of this principle, in which for example a non-functional part of a coding region fulfills its function if integrated in complementing parts of a target locus, or in which region X provides a promoter region to a promoter-less coding region of a target locus. A further possibility is to create regions X which provide sequences to a target locus, which destroys its normal function, e.g. a region X can be created to provide a stop-codon or a frame-shift mutation to a coding region of a target locus. Again, a person skilled in the art will be able to create further variants of this principle. A donor locus comprises a homologous region C and a homologous region D, which have sufficient sequence identity to a homologous region A and a homologous region B of a target locus in order to allow for homologous recombination to occur, wherein homologous region C of the donor locus will undergo homologous recombination with homologous region A of the target locus and homologous region D of the donor locus will undergo homologous recombination with homologous region B of the target locus.

A donor locus comprises also one, two or more rare cleaving nuclease cutting sites, which flank either homologous region C or homologous region D. Even more preferred, the donor locus comprises two or more rare cleaving nuclease cutting sites, which flank homologous region C and homologous region D. Rare cleaving nuclease cutting sites flank homologous regions C or D or homologous region C and D, when they are located close to homologous regions C or D or homologous regions C and D, but are not located between homologous regions C and D.

A donor locus may comprise one or more rare cleaving nuclease cutting sites, for one or more rare cleaving nucleases.

A donor locus may be transgenic or may be a naturally occurring sequence. Preferably the donor locus is a transgenic sequence.

In a preferred embodiment, of the methods described herein, the plant cell comprises at least one donor locus, comprising at least one homologous region E and at least one homologous region F, wherein homologous region(s) E and homologous region(s) F have sufficient sequence identity to be able to recombine via homologous recombination and wherein the at least one homologous region E and the least one homologous region F flank the at least one homologous region C and the at least one homologous region D.

In another embodiment of the methods described herein, the plant cell comprises a donor locus comprising an expression cassette for a rare cleaving nuclease, being able to nick or cut one, two or more rare cleaving nuclease cutting sites of a donor locus or one, two or more rare cleaving nuclease cutting sites of a target locus, or being able to nick or cut one, two or more rare cleaving nuclease cutting sites of a donor locus and one, two or more rare cleaving nuclease cutting sites of a target locus, Suitable rare cleaving nucleases including their genes have been described above.

In a preferred embodiment of the invention, the expression cassette for the rare cleaving nuclease, is located between at least one homologous region C and at least one homologous region D, or located between at least one homologous region E and at least one homologous region F, but outside of at least one homologous region C and at least one homologous region D, or outside of at least one homologous region E and at least one homologous region F.

In another preferred embodiment, of the methods described herein, the plant cell comprises at least one donor locus, which comprises at least one expression cassette for a selection marker, wherein the expression cassette is designed to express the selection maker in the plant cell or in progeny cells thereof.

The expression cassette for a selection marker may also be referred to as "marker gene".

The selection marker may be any selection maker of the following groups:

i) Positive selection markers:
As a rule, selection markers are required for selecting cells which have successfully undergone homologous recombination or transformation. The selectable marker which has been introduced together with the expression construct confers resistance to a biocide (for example a herbicide such as phosphinothricin, glyphosate or bromoxynil), a metabolism inhibitor such as 2-deoxyglucose-6-phosphate (WO 98/45456) or an antibiotic such as, for example, tetracyclins, ampicillin, kanamycin, G 418, neomycin, bleomycin or hygromycin to the cells which have successfully undergone recombination or transformation. The selection marker permits the selection of the transformed cells from untransformed cells (McCormick et al., Plant Cell Reports 5 (1986), 81-84). Especially preferred selection markers are those which confer resistance to herbicides. Examples of selection markers which may be mentioned are:
DNA sequences which encode phosphinothricin acetyltransferases (PAT), which acetylates the free amino group of the glutamine synthase inhibitor phosphinothricin (PPT) and thus brings about detoxification of the PPT (de Block et al. 1987, EMBO J. 6, 2513-2518) (also referred to as Bialophos®resistance gene (bar)),
5-enol pyruvylshikimate-3-phosphate synthase genes (EPSP synthase genes), which confer resistance to Glyphosate® (N-(phosphonomethyl)glycine),
the gox gene, which encodes the Glyphosate®-degrading enzyme (Glyphosate oxidoreductase),
the deh gene (encoding a dehalogenase which inactivates Dalapon®),
acetolactate synthases which inactivate sulfonylurea and imidazolinone,
bxn genes which encode Bromoxynil®-degrading nitrilase enzymes,
the kanamycin, or G418, resistance gene (NPTII). The NPTII gene encodes a neomycin phosphotransferase which reduces the inhibitory effect of kanamycin, neomycin, G418 and paromomycin owing to a phosphorylation reaction,
the DOGR1 gene. The DOGR1 gene has been isolated from the yeast Saccharomyces cerevisiae (EP 0 807 836). It encodes a 2-deoxyglucose-6-phosphate phosphatase which confers resistence to 2-DOG (Randez-Gil et al. 1995, Yeast 11, 1233-1240).
ii) Negative selection markers enable for example the selection of organisms with successfully deleted sequences which encompass the marker gene (Koprek T et al. (1999) The Plant Journal 19(6):719-726). TK thymidine kinase (TK) and diphtheria toxin A fragment (DT-A), codA gene encoding a cytosine deaminase (Gleve A P et al. (1999) Plant Mol Biol. 40(2):223-35; Pereat R I et al. (1993) Plant Mol. Biol 23(4): 793-799; Stougaard J; (1993) Plant J 3:755-761), the cytochrome P450 gene (Koprek et al. (1999) Plant J. 16:719-726), genes encoding a haloalkane dehalogenase (Naested H (1999) Plant J. 18:571-576), the iaaH gene (Sundaresan V et al. (1995) Genes & Development 9:1797-1810) or the tms2 gene (Fedoroff N V & Smith D L 1993, Plant J 3: 273-289).
iii) Dual use selection markers which can be used for positive and negative selection, as for example disclosed in WO05090581 and WO03072792.
iv) Reporter genes which encode readily quantifiable proteins and which, via intrinsic color or enzyme activity, ensure the assessment of the transformation efficacy or of the location or timing of expression. Very especially preferred here are genes encoding reporter proteins (see also Schenborn E, Groskreutz D. Mol Biotechnol. 1999; 13(1):29-44) such as
"green fluorescence protein" (GFP) (Chuff W L et al., Curr Biol 1996, 6:325-330; Leffel S M et al., Biotechniques. 23(5):912-8, 1997; Sheen et al. (1995) Plant Journal 8(5):777-784; Haseloff et al. (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228).
Chloramphenicol transferase,
luciferase (Millar et al., Plant Mol Biol Rep 1992 10:324-414; Ow et al. (1986) Science, 234:856-859); permits the detection of bioluminescence,
beta-galactosidase, encodes an enzyme for which a variety of chromogenic substrates are available, beta-glucuronidase (GUS) (Jefferson et al., EMBO J. 1987, 6, 3901-3907) or the uidA gene, which encodes an enzyme for a variety of chromogenic substrates, R locus gene product: protein which regulates the production of anthocyanin pigments (red coloration) in plant tissue and thus makes possible the direct analysis of the promotor activity without the addition of additional adjuvants or chromogenic substrates (Dellaporta et al., In: Chromosome Structure and Function: Impact of New Concepts, 18th Stadler Genetics Symposium, 11:263-282, 1988), beta-lactamase (Sutcliffe (1978) Proc Natl Acad Sci USA 75:3737-3741), enzyme for a variety of chromogenic substrates (for example PADAC, a chromogenic cephalosporin), xylE gene product (Zukowsky et al. (1983) Proc Natl Acad Sci USA 80:1101-1105), catechol dioxygenase capable of converting chromogenic catechols, alpha-amylase (Ikuta et al. (1990) Bio/technol. 8:241-242), tyrosinase (Katz et al. (1983) J Gene Microbiol 129:2703-2714), enzyme which oxidizes tyrosine to give DOPA and dopaquinone which subsequently form melanine, which is readily detectable, aequorin (Prasher et al. (1985) Biochem Biophys Res Commun 126(3):1259-1268), can be used in the calcium-sensitive bioluminescence detection In a preferred embodiment of the invention, the expression cassette for the selection marker, is located between at least one homologous region C and at least one homologous region D, or between at least one homologous region E and at least one homologous region F, but outside of at least one homologous region C and at least one homologous region D, or outside of at least one homologous region E and at least one homologous region F.

In a further embodiment of the methods described herein, the plant cell comprises at least one donor locus comprising at least one rare cleaving nuclease cutting site, which cannot be cut by the or any of the nucleases provided to induce the homologous recombination between the homologous regions C and D of the at least one donor locus and homologous regions A and B of the at least one target locus.

In a further embodiment of the invention, the donor locus comprises recombination sites capable to undergo a recombination reaction, in case the recombinase recognizing those sites is provided.

In an even further embodiment of the invention, at least one donor locus comprises at least one rare cleaving nuclease cutting site, which cannot be cut by the, or any of the nucleases provided to induce the homologous recombination between the homologous regions C and D of the at least one donor locus and homologous regions A and B of the at least one target locus and comprises recombination sites capable to undergo a recombination reaction, in case the recombinase recognizing those sites is provided.

The skilled worker is familiar with a variety of recombinases and their respective recognition sites which may be used in plant cells. Examples of suitable recombinases and their respective recognition sites are:

the Cre/lox system of the bacteriophage P1 (Dale E C and Ow D W (1991) Proc Natl Acad Sci USA 88:10558-10562; Russell S H et al. (1992) Mol Gene Genet 234: 49-59; Osborne B I et al. (1995) Plant J. 7, 687-701), the yeast FLP/FRT system (Kilby N J et al. (1995) Plant J 8:637-652; Lyznik L A et al. (1996) Nucleic Acids Res 24:3784-3789), the Mu phage Gin recombinase, and the *E. coli* Pin recombinase or the R/RS system of the plasmid pSR1 (Onouchi H et al. (1995) Mol. Gen. Genet. 247:653-660.; Sugita K et al. (2000) Plant J. 22:461-469).

In another embodiment of the methods described herein, the plant cell comprises no donor locus comprising a lethal gene or conditional lethal gene which can be used to select against ectopic insertions. Examples of lethal genes or conditional lethal genes are genes described in Yamauchi et al. 2009; Homologous recombination-mediated knock-in targeting of the MET1a gene for a maintenance DNA methyltransferase reproducibly reveals dosage-dependent spatiotemporal gene expression in rice; The Plant Journal; Volume 60, Issue 2, pages 386-396 or are negative marker genes located close to homologous region C and homologous region D of a donor locus, but not between homologous region C and homologous region D.

In another embodiment of the methods described herein, the plant cell comprises a donor locus comprising an expression cassette for a HR modifying sequence.

A HR modifying sequence is a sequence for overexpression or downregulation of genes involved in homologous recombination or non-homologous-end-joining. Preferably a HR modifying sequence is a sequence which enhances the capacity of a plant cell to perform homologous recombination or is a sequence which reduces the capacity of a plant cell to perform non-homologous-end-joining or is a sequence which enhances the capacity of a plant cell to perform homologous recombination and reduces the capacity of a plant cell to perform non-homologous-end-joining.

Genes which can be used to enhance homologous recombination in plant cells or to reduce the capacity of a plant cell to perform non-homologous-end-joining are known in the art and described above and include for example genes for overexpressing of a bacterial RecA gene or a yeast Rad54 gene as for example disclosed in U.S. Pat. No. 6,583,336 and Shaked et al. 2005; High-frequency gene targeting in *Arabidopsis* plants expressing the yeast RAD54 gene; PNAS, Vol. 102, Nr. 34, page 12265 to 12269. Other HR modifying sequences are the AtLIG4 gene and its respective homologs, or genes providing a reduced expression level of a gene involved in the NHEJ-repair mechanism, as for example RecQ4 or other genes being disclosed in WO11/052539, in WO11/078662, in WO0012716, in WO0222811, in WO04070035, in WO11078662 or in WO00/12716. HR modifying sequence include genes, which are naturally occurring protein coding sequences or recombinant protein coding sequences, as well as genes expressing naturally occurring or recombinant RNAs, e.g. miRNAs or dsRNAs, which have the capacity to modify the frequency or quality of homologous recombination reactions in plant cells.

In another embodiment of the methods described herein, the plant cell comprises a donor locus comprising an expression cassette for male fertility restorer gene. Naturally occurring and recombinant male fertility restorer genes are known in the art and are disclosed of example in CA2290883, in WO 03/006622, in WO 2004/006655, in WO 2004/018639, in WO03072792, WO02099111, in WO07047016, in WO08007854, in WO9429465, in WO9904023, WO9913089 or in WO9942598. Further examples are disclosed in Wang et al. "A chimeric Rfo gene generated by intergenic recombination co-segregates with the fertility restorer phenotype for cytoplasmic male sterility in radish"; Mol Breeding; 2010; vol. 25, pages 339-349, in Itabashi et al. "The fertility restorer gene, Rf2, for Lead Rice-type cytoplasmic male sterility of rice encodes a mitochondrial glycine-rich protein"; The Plant Journal (2011);

vol 65, pages 359 to 367, in Kempe and Gils; "Pollination control technologies for hybrid breeding"; Mol Breeding; (2011); Vol. 27; pages 417 to 437 and in the references cited therein.

The expression cassette for the male fertility restorer gene may be located either between at least one homologous region C and at least one homologous region D, or between at least one homologous region E and at least one homologous region F, but outside of at least one homologous region C and at least one homologous region D, or outside of at least one homologous region E and at least one homologous region F.

Especially preferred donor loci are described in FIGS. 1 to 18, including the description of FIGS. 1 to 18.

Design of Target Loci:

The methods for targeted integration or targeted exchange of sequences disclosed herein comprise the use of one, two or more target loci, comprising a region Z, which is intended to be replaced by or exchanged with a region X of a donor locus.

The region Z of a target locus can, in principle, be any kind of DNA sequence. A region Z may be shorter or longer than the respective region X, and can have a length of one base pair or can range up to several thousand base pairs. Typically a region Z has a length of 1 to 50000 bps, preferably 1 to 40000 bps, 1 to 30000 bps, 1 to 20000 bps, 1 to 10000 bps, 1 to 9000 bps, 1 to 8000 bps, 1 to 7000 bps, 1 to 6000 bps, 1 to 5000 bps, 1 to 4000 bps, 1 to 3000 bps, 1 to 2000 bps, 1 to 1000 bps or 1 to 500 bps.

Region Z may comprise polynucleotide sequences, which have the ability to perform a certain function in a plant cell, for example, region Z may comprise one or more promoters, coding regions, terminator sequences, enhancer sequences, matrix-attachment regions, or one or more expression cassettes. Alternatively, region Z may comprise sequences which block such functions. For example a sequence of a target locus may become functional in a plant cell if a region Z is replaced or exchanged with a region X of a donor locus. For example region X may comprise part of a promoter sequence, which is not functional in plant cells, but becomes functional if integrated in a target locus, which comprises complementing parts of the promoter sequence in which the part of a promoter sequence provided by region X will fulfill its intended function. A person skilled in the art will be able to create further variants of this principle, which is similar to the situation described above for region X of the donor locus.

A target locus comprises a homologous region A and a homologous region B, which have sufficient sequence identity to a homologous region C and a homologous region D of a donor locus in order to allow for homologous recombination to occur, wherein homologous region C of the donor locus will undergo homologous recombination with homologous region A of the target locus and homologous region D of the donor locus will undergo homologous recombination with homologous region B of the target locus.

A target locus comprises also one, two or more rare cleaving nuclease cutting sites, which flank region Z or are located in region Z. Rare cleaving nuclease cutting sites flank region Z, when they are located between homologous regions A and region Z or between homologous region B and region Z or between region Z and homologous regions A and homologous region B.

A target locus may comprise one or more rare cleaving nuclease cutting sites, for one or more rare cleaving nucleases.

A target locus may be transgenic or may be a naturally occurring sequence. Preferably the target locus is a transgenic sequence.

In another embodiment of the methods described herein, the plant cell comprises a target locus comprising an expression cassette for a rare cleaving nuclease, being able to nick or cut one, two or more rare cleaving nuclease cutting sites of a donor locus or one, two or more rare cleaving nuclease cutting sites of a target locus, or being able to nick or cut one, two or more rare cleaving nuclease cutting sites of a donor locus and one, two or more rare cleaving nuclease cutting sites of a target locus, Suitable rare cleaving nucleases including their genes have been described above.

In a preferred embodiment of the invention, the expression cassette for the rare cleaving nuclease, is located between at least one homologous region A and at least one homologous region B.

In a preferred embodiment, of the methods described herein, the plant cell comprises at least one target locus, comprising an expression cassette for a selection marker, which is suitable express the selection marker in the plant cell or in progeny cells thereof, or in the plant cell and in progeny cells thereof, Preferably the expression cassette for the selection marker is located between at least one homologous region A and at least one homologous region B, or outside of at least one homologous region A and at least one homologous region B.

In an even more preferred embodiment the expression cassette for the selection marker is located between at least two rare cleaving nuclease cutting sites.

Suitable selection markers have already been described above in context of the design of donor loci.

In another embodiment of the methods described herein, the plant cell comprises a target locus comprising an expression cassette for a HR modifying sequence.

Suitable HR modifying sequences have already been described above in context of the design of donor loci.

In a preferred embodiment, the expression cassette for HR modifying sequence is located between at least one homologous region A and at least one homologous region B.

In a further embodiment of the methods described herein, the plant cell comprises a target locus comprising an expression cassette for a male fertility restorer gene.

Suitable male fertility restorer genes have already been described above in context of the design of donor loci.

In a preferred embodiment, the expression cassette for the male fertility restorer is located between at least one homologous region A and at least one homologous region B.

Especially preferred target loci are described in FIGS. 1 to 18, including the description of FIGS. 1 to 18.

Design of Nuclease Loci:

In some embodiments of the invention, the plant cell comprises at least one target locus, at least one donor locus and a nuclease locus.

A nuclease locus comprises an expression cassette for a rare cleaving nuclease. Suitable rare cleaving nucleases including their genes have been described above.

In a preferred embodiment of the invention, the nuclease locus comprises an expression cassette for a rare cleaving nuclease and a homologous region J and a homologous region K, which have sufficient sequence identity in order to be able to undergo homologous recombination between each other, and comprises at least one rare cleaving nuclease cutting site, which can be nicked or cut by the rare cleaving nuclease encoded by the expression cassette for the rare cleaving nuclease.

In a further embodiment of the invention, the nuclease locus comprises further an expression cassette for a selection marker, or an expression cassette for a HR modifying sequence or an expression cassette for a selection marker and an expression cassette for a HR modifying sequence. The expression cassette for the selection marker or the expression cassette for a HR modifying sequence or the expression cassette for a selection marker and the expression cassette for a HR modifying sequence is preferably located between homologous region J and homologous region K.

Preferably the rare cleaving nuclease is expressed via an inducible, or tissue specific promoter.

Figure 8:
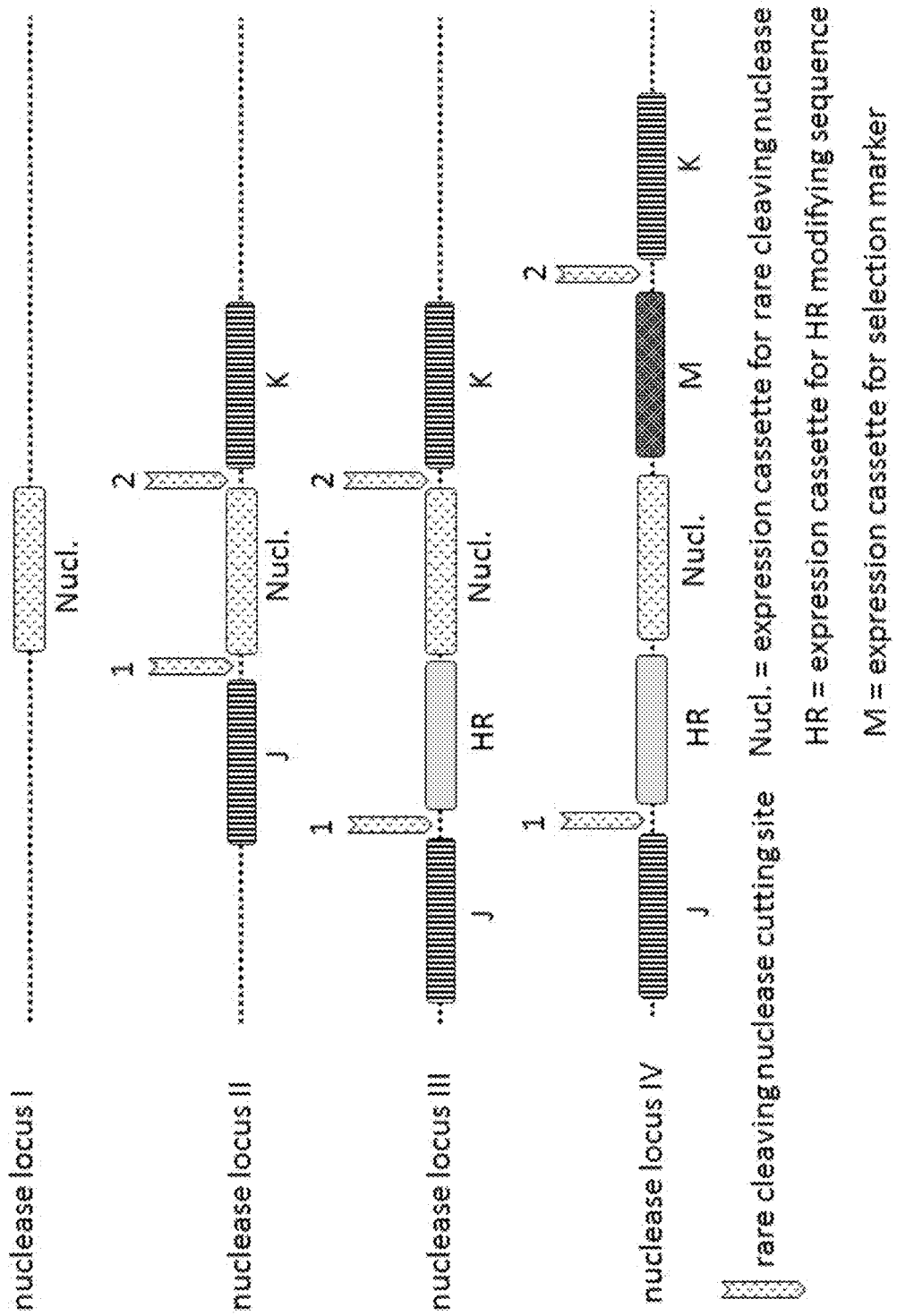
FIG. 8 depicts exemplary designs of loci used to provide the rare cleaving nuclease (nuclease locus I, nuclease locus II, nuclease locus III and nuclease locus IV), which may be used in combination with any target locus or donor locus described herein. Nuclease locus I is preferably integrated in the nuclear genome of a plant cell and comprises an expression cassette for induced, tissue specific or constitutive expression of a rare cleaving nuclease. Nuclease locus II comprises an expression cassette as described for Nuclease locus II, is preferably integrated in the nuclear genome of a plant cell and comprises an expression cassette for induced, tissue specific or constitutive expression, preferably induced or tissue specific expression, of a rare cleaving nuclease, flanked by one or two rare cleaving nuclease cutting sites of the nuclease expressed from the expression cassette, located between homologous regions J and K, which have sufficient sequence identity to be able to recombine via homologous recombination. Nuclease locus III comprise all elements already described for nuclease locus II, but comprises also at least one expression cassette for a sequence which has the capacity to modify the frequency of homologous recombination in plant cells (HR modifying sequence). The expression cassette for the HR modifying sequence is preferably located between homologous regions J and homologous region K. Nuclease locus IV comprises all elements already described for nuclease locus III, but does also comprise an expression cassette for a selection marker M. The expression cassette for a selection marker is preferably located between homologous region J and homologous region K.
Figure 9:
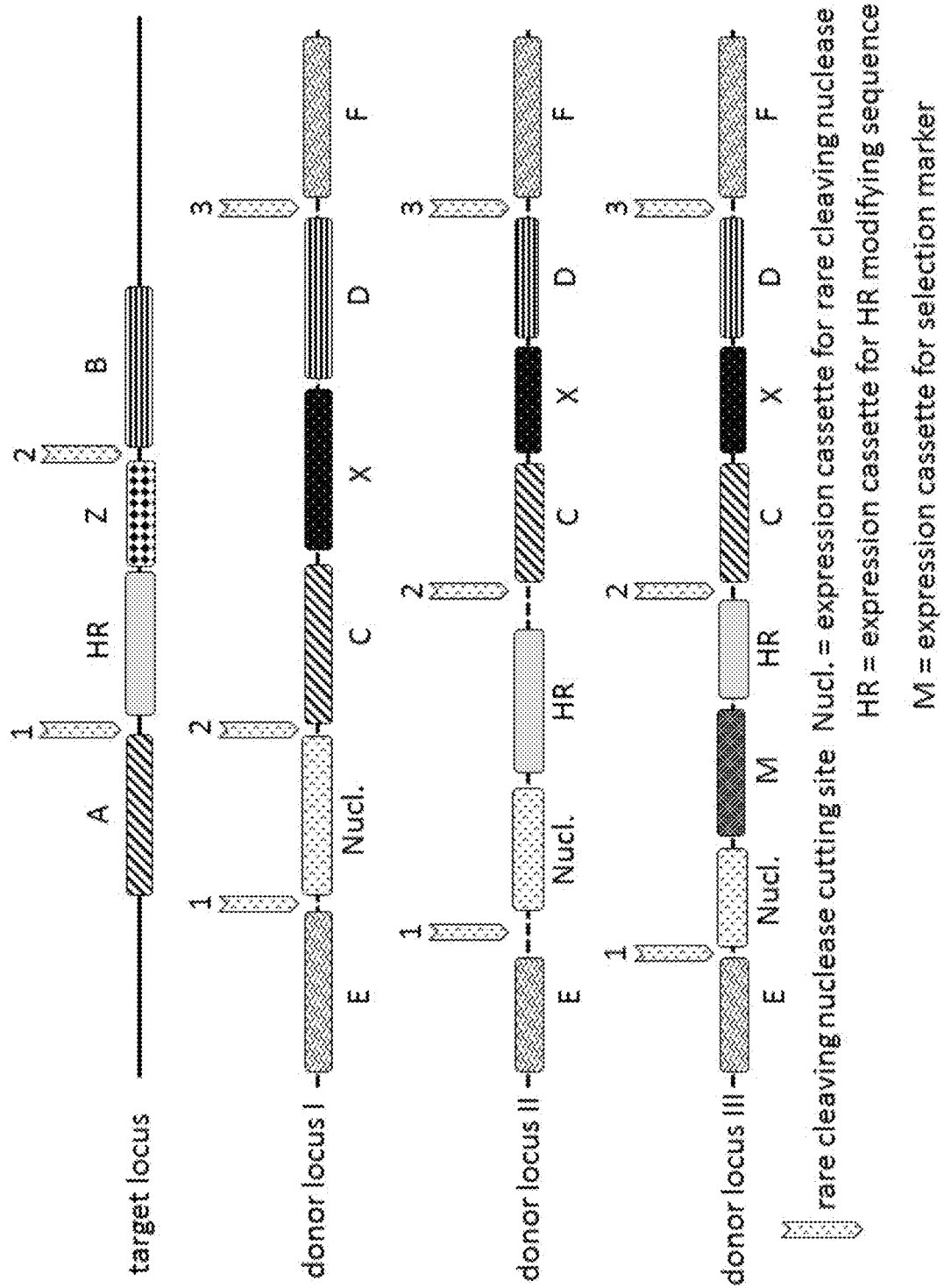
FIG. 9 depicts further alternative designs of target and donor loci (target locus, donor locus I, donor locus II and donor locus III). The target locus of FIG. 9 comprises all elements described for the target locus of FIG. 2. In addition thereto it comprises an expression cassette for at least one expression cassette for a sequence which has the capacity to modify the frequency of homologous recombination in plant cells (HR modifying sequence). The expression cassette for the HR modifying sequence is preferably located between homologous regions A and homologous region B. The donor locus I of FIG. 9 comprises all elements described for the donor locus of FIG. 4, but comprises also an expression cassette for induced, tissue specific or constitutive expression, preferably induced or tissue specific expression, of a rare cleaving nuclease, located between homologous region E and homologous region F. The donor locus I of FIG. 9 comprises also one, two, three or more rare cleaving nuclease cutting sites of the nuclease expressed from the expression cassette. Those rare cleaving nuclease cutting sites being located between homologous region E and homologous region J, but not between homologous region C and homologous region D. The donor locus II of FIG. 9 comprises all elements described for the donor locus I of FIG. 9. In addition to that, donor locus II comprises also an expression cassette for a HR modifying sequence (HR) which is preferably located between homologous region E and homologous region F, but not between homologous region C and homologous region D. Donor locus II comprises also one, two, three or more rare cleaving nuclease cutting sites, located between homologous region E and homologous region F, but not between homologous region C and homologous region D, preferably located between homologous region E and homologous region C and homologous region D and homologous region F. Donor locus III of FIG. 9 comprises all elements already described for donor locus II of FIG. 9, but comprises in addition to that an expression cassette for a selection marker, which is preferably located between homologous region E and homologous region F, but not between homologous region C and homologous region D.
Figure 10:
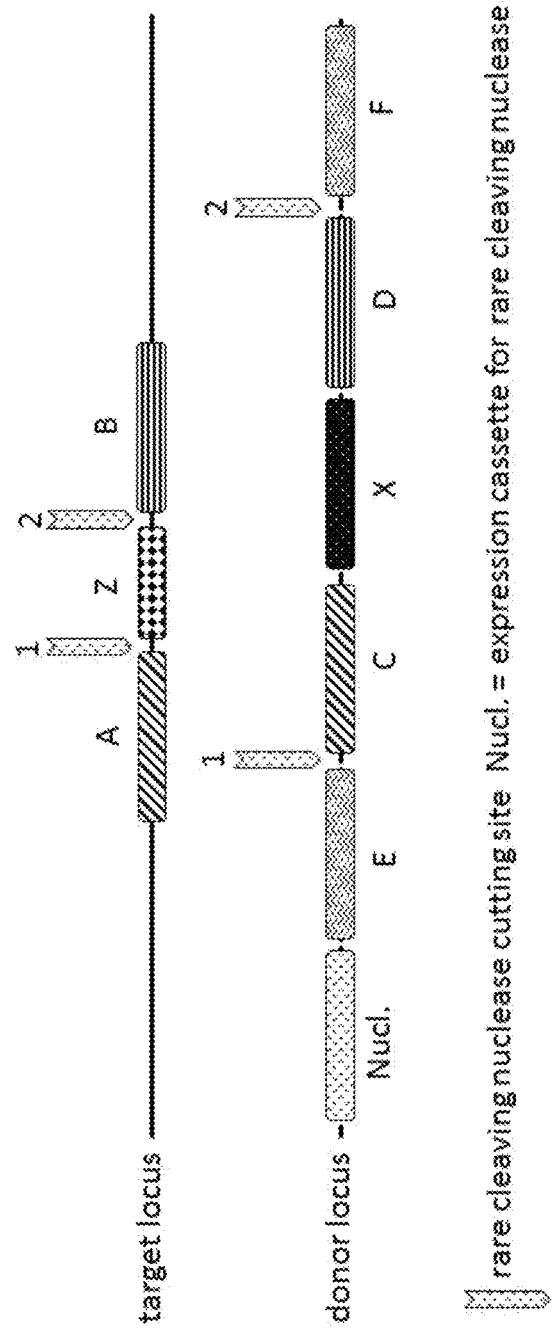
FIG. 10 depicts an exemplary combination of a target locus and a donor locus. The target locus comprises all elements described for the target locus of FIG. 2. The donor locus comprises all elements described for the donor locus of FIG. 4, but does also comprise an expression cassette for induced, tissue specific or constitutive expression, preferably induced or tissue specific expression, of a rare cleaving nuclease, located close to homologous region E or homologous region F, but not between homologous region E and homologous region F.
Figure 11:
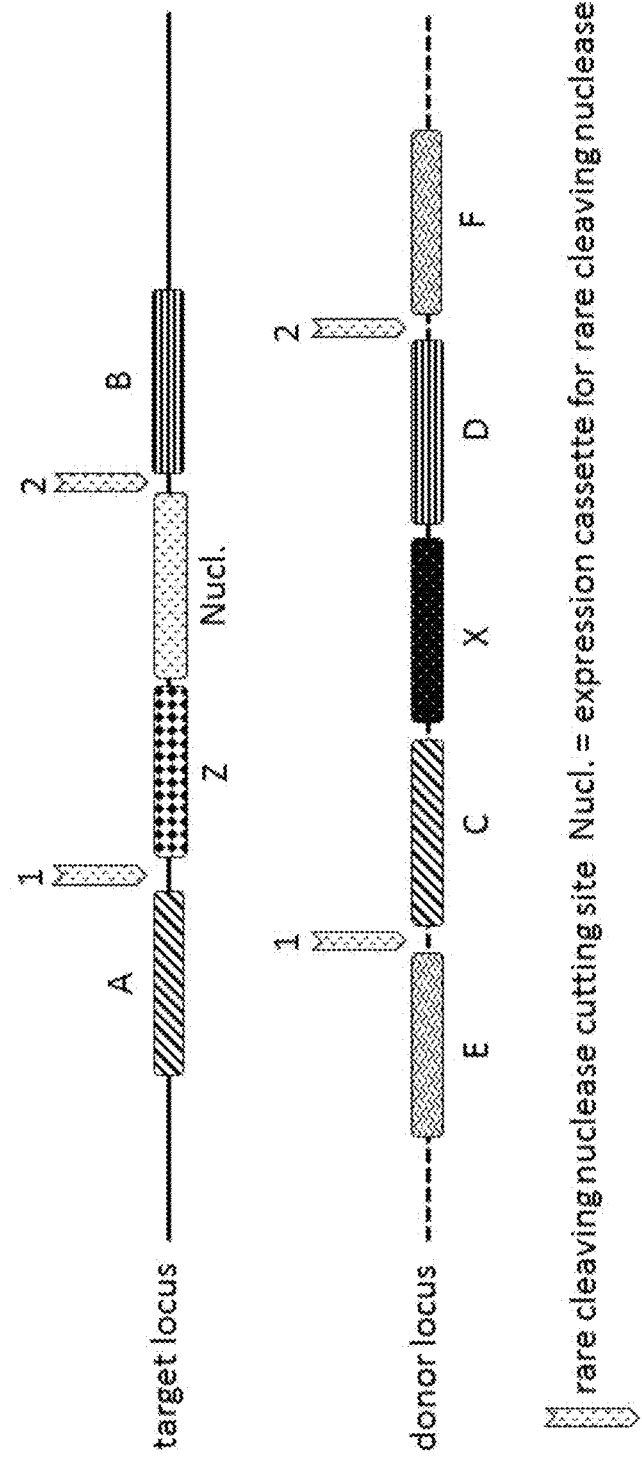
FIG. 11 depicts an exemplary combination of a target locus and a donor locus. The target locus comprises all elements described for the target locus of FIG. 4. In addition thereto it comprises an expression cassette for induced, tissue specific or constitutive expression, preferably induced or tissue specific expression, of a rare cleaving nuclease, located between homologous region A and homologous region B. The donor locus comprises all elements described for the donor locus of FIG. 4.
Figure 12:
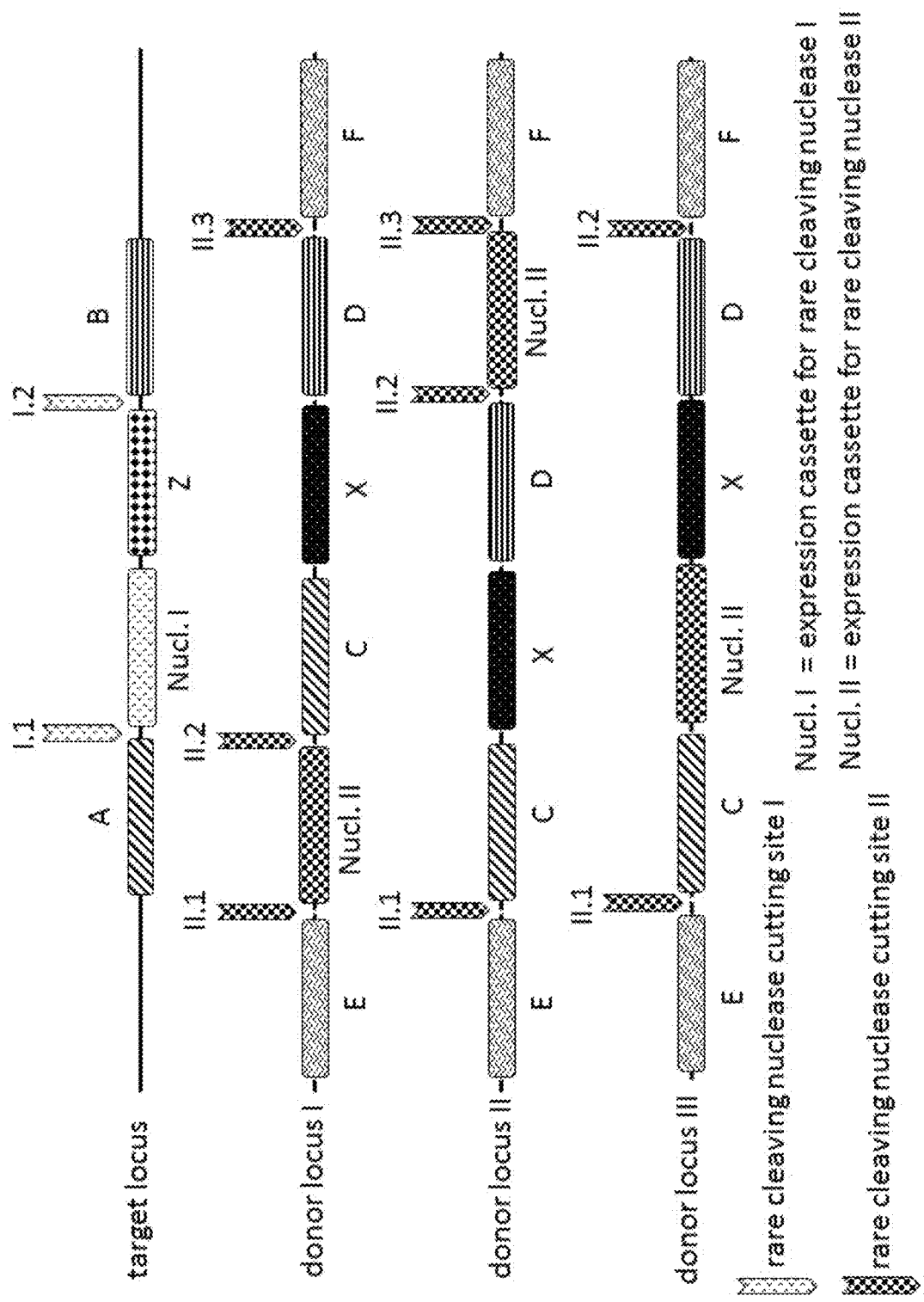
FIG. 12 depicts exemplary combinations of a target locus with three alternative donor loci (donor locus I, donor locus II and donor locus III). The target locus comprises all elements described for the target locus of FIG. 11, showing region Z at an alternative position. All three alternative donor loci comprise all elements described for the donor locus I of FIG. 9, showing the expression cassette for an expression cassette for induced or tissue specific expression, of a rare cleaving nuclease, located between homologous region E and homologous region F. The difference between the three alternative donor loci is the location of the expression cassette for the rare cleaving nuclease. The rare cleaving nuclease expressed from the expression cassette of the target locus (Nucl. I) cuts or nicks preferably the one, two or more rare cleaving nuclease cutting sites of the target locus (I.1 and I.2). The rare cleaving nuclease expressed from the expression cassette of the donor locus (Nucl. II) cuts or nicks preferably the one, two, three or more rare cleaving nuclease cutting sites of the alternative donor loci (II.1, II.2 and if present II.3), wherein the rare cleaving nuclease cutting sites of the alternative donor loci are located between homologous region E and homologous region F, but not between homologous region C and homologous region D.
Figure 13:
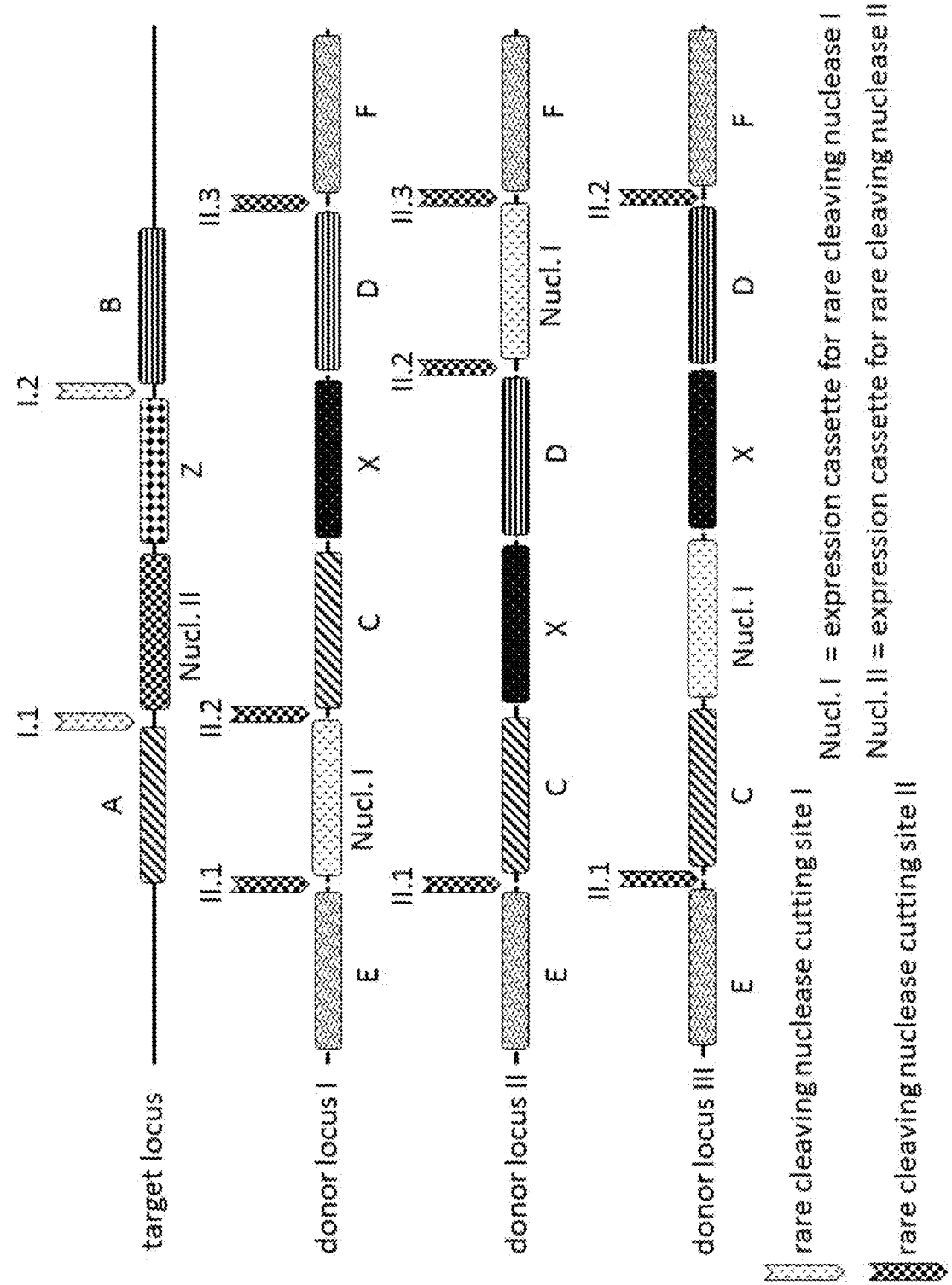
FIG. 13 depicts a similar combination of a target locus with three alternative donor loci (donor locus I, donor locus II and donor locus III) as described for FIG. 12.
Figure 14:
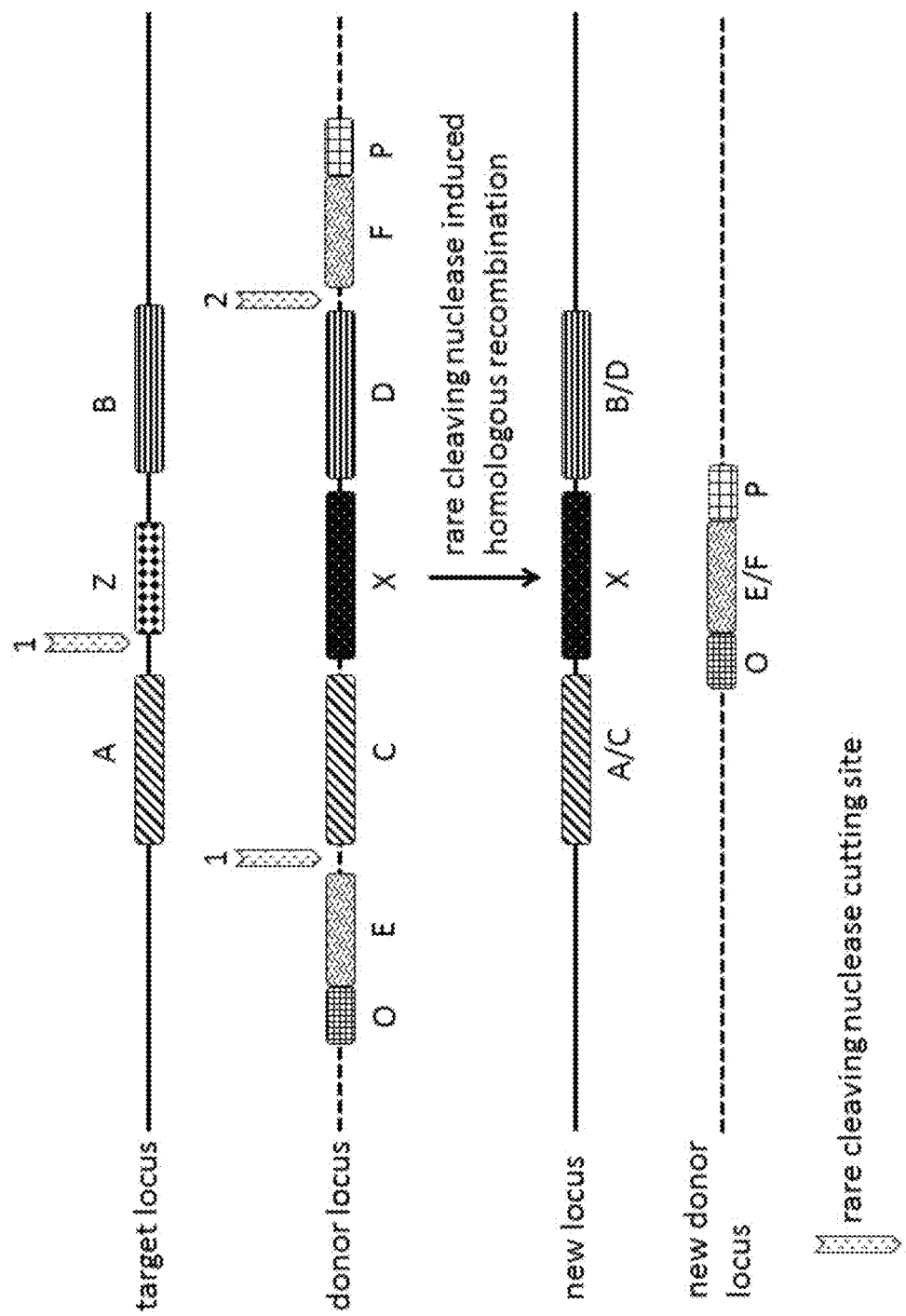
FIG. 14 depicts a similar combination of a target locus and a donor locus, followed by a rare cleaving nuclease induced homologous recombination as already described for FIG. 3.

Especially preferred target loci are described in FIG. 8, including the description of FIG. 8.

Combination of Target Loci, Donor Loci and Nuclease Loci:

The methods for modifying a target locus in a plant cell disclosed herein can be used in combination with a great variety of different donor locus, target locus and nuclease locus designs and combinations. Exemplary designs have been described above, preferred designs of donor locus, target locus and nuclease locus designs are described in FIGS. 1 to 18, as well as in the respective description of FIGS. 1 to 18.

In a preferred combination of donor locus, target locus and nuclease locus combinations used in the methods for modifying a target locus in a plant cell, at least one donor locus, or at least one target locus or at least one nuclease locus comprise an expression cassette for a selective marker, preferably at least one donor locus, or at least one nuclease locus comprises an expression cassette for a selective marker, which is preferably not located between homologous region C and homologous region D of the donor locus, even more preferred, an expression cassette for a selective marker is located between homologous region E and homologous region F but not between homologous region C and homologous region D of a donor locus.

In another preferred embodiment the nuclease locus comprises an expression cassette for a selective marker being located between a homologous region E and a homologous region F.

In a preferred combination of donor locus, target locus and nuclease locus combinations used in the methods for modifying a target locus in a plant cell, at least one donor locus, or at least one target locus or at least one nuclease locus comprise an expression cassette for a HR modifying sequence, preferably at least one donor locus, or at least one nuclease locus comprises an expression cassette for a HR modifying sequence, which is preferably not located between homologous region C and homologous region D of the donor locus, even more preferred, an expression cassette for a HR modifying sequence is located between homologous region E and homologous region F but not between homologous region C and homologous region D of a donor locus.

In another preferred embodiment the nuclease locus comprises an expression cassette for a HR modifying sequence being located between a homologous region E and a homologous region F.

In a preferred combination of donor locus, target locus and nuclease locus combinations used in the methods for modifying a target locus in a plant cell, at least one donor locus, or at least one target locus or at least one nuclease locus comprise an expression cassette for a male fertility restorer gene, preferably at least one donor locus, or at least one nuclease locus comprises an expression cassette for a male fertility restorer gene, which is preferably not located between homologous region C and homologous region D of the donor locus, even more preferred, an expression cassette for a male fertility restorer gene is located between homologous region E and homologous region F but not between homologous region C and homologous region D of a donor locus.

In another preferred embodiment the nuclease locus comprises an expression cassette for a male fertility restorer gene being located between a homologous region E and a homologous region F.

In a preferred combination of donor locus, target locus and nuclease locus combinations used in the methods for modifying a target locus in a plant cell, at least one donor locus, or at least one target locus or at least one nuclease locus comprise an expression cassette for a selective marker and an expression cassette for a HR modifying sequence or an expression cassette for a male fertility restorer or comprises an expression cassette for a selective marker, an expression cassette for a HR modifying sequence and an expression cassette for a male fertility restorer.

In another preferred combination of donor locus and target locus, either the donor locus or the target locus or both comprise an expression cassette for a rare cleaving nuclease. Preferably the expression cassette for the rare cleaving nuclease is not located between homologous region C and homologous region D of a donor locus. Even more preferred is a location of an expression cassette for a rare cleaving nuclease between a homologous region E and homologous region F, but not between homologous region C and homologous region D of a donor locus. Another preferred location for an expression cassette for a rare cleaving nuclease is between homologous region A and homologous region B of a target locus.

In another preferred embodiment of the invention, the region X of the donor locus comprises one or more genes, or the region Z of the target locus comprises one or more genes, or the region X of the donor locus and the region Z of the target locus comprises one or more genes.

These genes can be any genes of interest.

In another preferred embodiment of the invention, the donor locus and the target locus comprise one, two, three or more rare cleaving nuclease cutting sites, which can be nicked or cut by the same rare cleaving nuclease.

In a further embodiment of the invention, a donor locus, a target locus and a nuclease locus comprise one, two, three or more rare cleaving nuclease cutting sites, which can be nicked or cut by the same rare cleaving nuclease.

Preferably at least one donor locus and at least one target locus are located on the same or on homologous chromosomes, or are located on homologous regions of otherwise non-homologous chromosomes. Such homologous regions, may have been originated by translocated chromosomal fragments or may be homologous regions originated by auto- or allopolyploidisation of plant cells. Plant species having homologous chromosomes and homologous regions of non-homologous chromosomes originated by chromosomal translocations and/or auto- or allo-polyploidisations are for example: tetraploid or hexaploid wheat, cotton, brassica, citrus, tobacco, plum, or triticale. Further plant species are known in the art.

In another embodiment of the invention, the plant cell comprises a target locus and a donor locus at allelic positions. In a further embodiment of the invention, the plant cell comprises a target locus and a donor locus on non-allelic positions.

In an even further embodiment of the invention the plant cell used in the methods for modifying a target locus in a plant cell disclosed herein comprises a transgenic target locus, or a transgenic donor locus, or a transgenic target locus and a transgenic donor locus.

In an further embodiment of the invention, the rare cleaving nuclease is expressed via a constitutive promoter, or an inducible promoter, or a tissue specific promoter, or an organ specific promoter, or a developmental stage specific promoter, or transported inside the cell nucleus upon an external, or tissue specific, or organ specific, or developmental stage specific stimulus.

Number and Relationship of Donor Loci and Target Loci:

The methods for modifying a target locus in a plant cell disclosed herein can be used to transfer alternative regions X of different donor loci to one or more target loci. For example, a plant cell may comprise a single target locus, which comprises rare cleaving nuclease cutting sites for different rare cleaving nucleases. Depending on which kind of rare cleaving nuclease is provided this may result in homologous recombination reaction with one donor locus or the other donor locus. It is also possible to employ a reverse situation, in which a region X of one donor locus is transferred to alternative target loci, depending on which rare cleaving nuclease is provided. Further variations, including the parallel transfer of different regions X of different donor loci, to different target loci, which is induced by nicks or cuts with the same rare cleaving nuclease, but directed by compatible sequences of homologous regions A, B, C and D of one target locus/donor locus which differ in form the compatible sequences of homologous regions A, B, C, and D of the other target locus/donor locus combination or combinations comprised by the plant cell.

Accordingly, the invention comprises embodiments, wherein the plant cell comprises two or more target loci each comprising at least one homologous region A and at least one homologous region B, or two or more donor loci each comprising at least one homologous region C and at least one homologous region D, or two or more target loci each comprising at least one homologous region A and at least one homologous region B and two or more donor loci each comprising at least one homologous region C and at least one homologous region D, wherein homologous region(s) A and homologous region(s) C have sufficient sequence identity to be able to recombine via homologous recombination and homologous region(s) B and homologous region(s) D have sufficient sequence identity to be able to recombine via homologous recombination.

Further embodiments of the invention use plant cells, which are homozygous for at least one target locus or are homozygous for at least one donor locus or are homozygous for at least one target locus and are homozygous for at least one donor locus.

The plant cells used in the methods for modifying a target locus of a plant cell being disclosed herein may comprise a proportion of the target locus to the donor loci or the proportion of the target loci to the donor locus or the proportion of the target loci to the donor loci, is 1:1, 1:2, 1:3, 1:4, 1:5, 1:6, or 6:1, 5:1, 4:1, 3:1, 2:1.

A further embodiment of the methods of the invention employ plant cells, wherein the nucleotide sequence between homologous region(s) A and homologous region(s) B of at least two target loci is not identical, or the nucleotide sequence between homologous region(s) C and homologous region(s) D of at least two donor loci is not identical, or the nucleotide sequence between homologous region(s) A and homologous region(s) B of the at least two target loci is not identical and the nucleotide sequence between homologous region(s) C and homologous region(s) D of at least two donor loci is not identical.

Methods to Provide Target Loci, Donor Loci and Rare Cleaving Nucleases.

As described already above, plant cells used in the methods of the invention may comprise naturally occurring target and donor loci, or may comprise at least one transgenic target locus or at least one transgenic donor locus or may comprise at least one transgenic target locus and at least one transgenic donor locus.

In case the plant cell comprises only naturally occurring target and donor loci, it is possible to provide the rare cleaving nuclease being able to cut or nick at least one rare cleaving nuclease cutting site in at least one target locus or at least one donor locus, via stable or transient transformation of the plant cell with an expression cassette for a rare cleaving nuclease, for example using transgenic sequences comprising a nuclease locus as described herein. Another possibility is to provide the rare cleaving nuclease via infection with a viral vector which is able to express the rare cleaving nuclease. Alternatively the rare cleaving nuclease may be provided via a Sec III or SecIV secretion system of a plant infecting bacterium, preferably *Agrobacterium*. A further possibility is to provide the rare cleaving nuclease via particle bombardment or a combination with substances, e.g. peptide sequences, which have the ability to transport proteins via cell membranes.

In case at least one of the target loci or donor loci is a transgenic sequence, it is possible to transform a plant cell comprising at least one target locus with a transgenic construct comprising a donor locus, or to transform a plant cell comprising a donor locus with a transgenic construct comprising a target locus. In these cases, the target locus comprises at least two rare cleaving nuclease cutting sites located between homologous regions A and homologous region B, which can be cut or nicked by the same rare cleaving nuclease.

In a further embodiment of the invention, the plant cell comprises at least one transgenic target and at least one naturally occurring donor locus or comprises at least one naturally occurring target locus and at least one transgenic donor locus, or comprises at least one transgenic target locus and at least one transgenic donor locus, wherein the transgenic target locus or loci and the transgenic donor locus or loci are integrated in the nuclear genome of the plant cell. Such plant cell is then provided with a rare cleaving nuclease being able to nick or cut at least one rare cleaving nuclease cutting site in at least one target locus or at least one donor locus or in at least one target locus and at least one donor locus. The rare cleaving nuclease can be provided by providing an expression cassette for such rare cleaving nuclease, or by inducing expression from an expression cassette for such rare cleaving nuclease, or by growing the plant cell or the plant comprising such plant cell to a developmental stage, in which such rare cleaving nuclease is expressed, or by providing a rare cleaving nuclease by particle bombardment, infection with a viral vector comprising an expression cassette for such rare cleaving nuclease or by providing the rare cleaving nuclease via a Sec III or SecIV secretion system of a plant infecting bacterium, preferably an *Agrobacterium*, or by providing such rare cleaving nuclease via translocation through a the cell membrane e.g. via fusion with peptides having such ability.

In order to provide a plant cell comprising at least one transgenic target and at least one naturally occurring donor locus or comprising at least one naturally occurring target locus and at least one transgenic donor locus, or comprising at least one transgenic target locus and at least one transgenic donor locus, wherein the transgenic target locus or loci and the transgenic donor locus or loci are integrated in the nuclear genome of the plant cell, plant cell can be stably transformed with at least one transgenic target locus or at least one transgenic donor locus, whatever is necessary to create at least one compatible pair of target locus and donor locus in order to allow for homologous recombination between this pair. Alternatively, the plant cell can be co-transformed with several target loci or several target loci or several target loci and donor loci, whatever is necessary to create at least one compatible pair of target locus and donor locus in order to allow for homologous recombination between this pair.

Stably transformed means in this context, that the transgenic target loci or transgenic donor loci or both are integrated in the nuclear genome and transmitted to the progeny cells for at least some cell generations, preferably stably transformed means in this context, that the transgenic target loci or transgenic donor loci or both are integrated in the nuclear genome and transmitted to the progeny plants over one, two or more generations.

Methods for plant transformation and plant regeneration are well known in the art. Target loci, donor loci and nuclease loci, employed in the invention and therefore also referred to as transgenic loci of the invention, or transgenic locus of the invention, may advantageously be introduced into cells using vectors into which said DNA constructs comprising at least one target locus or comprising at least one donor locus or comprising at least one nuclease locus is inserted. Examples of vectors may be plasmids, cosmids, phages, plant viruses, or agrobacteria.

A DNA construct can be introduced into the target plant cells and/or organisms by any of the several means known to those of skill in the art. For instance, the DNA constructs can be introduced into plant cells, either in culture or in the organs of a plant by a variety of conventional techniques. For example, the DNA constructs can be introduced directly to plant cells using ballistic methods, such as DNA particle bombardment, or the DNA construct can be introduced using techniques such as electroporation and microinjection of cell. Particlemediated transformation techniques (also known as "biolistics" or "particle bombardment") are described in, e.g., Klein et al. (1987) Nature 327:70-73; Vasil V et al. (1993) BiolTechnol 11:1553-1558; and Becker D et al. (1994) Plant J 5:299-307. These methods involve penetration of cells by small particles with the nucleic acid either within the matrix of small beads or particles, or on the surface. The biolistic PDS-1000 Gene Gun (Biorad, Hercules, Calif.) uses helium pressure to accelerate DNA-coated gold or tungsten microcarriers toward target cells. The process is applicable to a wide range of tissues and cells from organisms, including plants. Other transformation methods are also known to those of skill in the art. Microinjection techniques are known in the art and are well described in the scientific and patent literature. Also, the cell can be permeabilized chemically, for example using polyethylene glycol, so that the DNA can enter the cell by diffusion. The DNA can also be introduced by protoplast fusion with other DNA-containing units such as minicells, cells, lysosomes or liposomes. The introduction of DNA constructs using polyethylene glycol (PEG) precipitation is described in Paszkowski et al. (1984) EMBO J 3:2717. Liposome-based gene delivery is e.g., described in WO 93/24640; Mannino and Gould-Fogerite (1988) BioTechniques 6(7):682-691; U.S. Pat. No. 5,279,833; WO 91/06309; and Feigner et al. (1987) Proc Natl Acad Sci USA 84:7413-7414). Another suitable method of introducing recombinant sequences is electroporation, where the cells are permeabilized reversibly by an electrical pulse. Electroporation techniques are described in Fromm et al. (1985) Proc Natl Acad Sci USA 82:5824. PEG-mediated transformation and electroporation of plant protoplasts are also discussed in Lazzeri P (1995) Methods Mol Biol 49:95-106. Preferred general methods which may be mentioned are the calcium-phosphate-mediated transfection, the DEAEdextran-mediated transfection, the cationic lipid-mediated transfection, electroporation, transduction and infection. Such methods are known to the skilled worker and described, for example, in Davis et al., Basic Methods In Molecular Biology (1986). For a review of gene transfer methods for plant and cell cultures, see, Fisk et al. (1993) Scientia Horticulturae 55:5-36 and Potrykus (1990) CIBA Found Symp 154:198. Methods for introduction and stable integration of recombinant sequences are known for monocot and dicot plants. See, e.g., U.S. Pat. Nos. 5,633,446, 5,317,096, 5,689,052, 5,159,135, and 5,679,558; Weising et al. (1988) Ann. Rev. Genet. 22: 421-477. Transformation of monocots in particular can use various techniques including electroporation (e.g., Shimamoto et al. (1992) Nature 338: 274-276; biolistics (e.g., EP-A1 270,356); and *Agrobacterium* (e.g., Bytebier et al. (1987) Proc Natl Acad Sci USA 84:5345-5349).

In plants, methods for transforming and regenerating plants from plant tissues or plant cells with which the skilled worker is familiar are exploited for transient or stable transformation. Suitable methods are especially protoplast transformation by means of poly-ethylene-glycol-induced DNA uptake, biolistic methods such as the gene gun ("particle bombardment" method), electroporation, the incubation of dry embryos in DNA-containing solution, sonication and microinjection, and the transformation of intact cells or tissues by micro- or macro-injection into tissues or embryos, tissue electroporation, or vacuum infiltration of seeds. In the case of injection or electroporation of DNA into plant cells, the plasmid used does not need to meet any particular requirement. Simple plasmids such as those of the pUC series may be used. If intact plants are to be re-generated from the transformed cells, the presence of a selectable marker on at least one of the target loci, donor loci or nuclease loci is useful.

In addition to these "direct" transformation techniques, transformation can also be carried out by bacterial infection, preferably by means of disarmed *Agrobacterium tumefaciens* or *Agrobacterium rhizogenes* strains. These strains contain a plasmid (Ti or Ri plasmid). Part of this plasmid, termed T-DNA (transferred DNA), is transferred to the plant following *Agrobacterium* infection and integrated into the genome of the plant cell.

For *Agrobacterium*-mediated transformation of plants, a DNA construct of the invention may be combined with suitable T-DNA flanking regions and introduced into a conventional *Agrobacterium* host. The virulence functions of the *Agrobacterium* host will direct the insertion of a transgene and adjacent marker gene(s) (if present) into the plant cell DNA when the cell is infected by the bacteria. *Agrobacterium* mediated transformation techniques are well described in the scientific literature. See, for example, Horsch et al. (1984) Science 233:496-498, Fraley et al. (1983) Proc Natl Acad Sci USA 80:4803-4807, Hooykaas (1989) Plant Mol Biol 13:327-336, Horsch R B (1986) Proc Natl Acad Sci USA 83(8):2571-2575), Bevans et al. (1983) Nature 304:184-187, Bechtold et al. (1993) Comptes Rendus De L'Academie Des Sciences Serie III-Sciences De La Vie-Life Sciences 316:1194-1199, Valvekens et al. (1988) Proc Natl Acad Sci USA 85:5536-5540.

Transgenic locus of the invention is preferably integrated into specific plasmids, either into a shuttle, or intermediate, vector or into a binary vector). If, for example, a Ti or Ri plasmid is to be used for the transformation, at least the right border, but in most cases the right and the left border, of the Ti- or Ri-plasmid T-DNA is linked with the recombinant sequence to be introduced as a flanking region. Binary vectors are preferably used. Binary vectors are capable of replication both in E. coli and in Agrobacterium. As a rule, they contain a selection marker gene and a linker or polylinker flanked by the right or left T-DNA flanking sequence. They can be transformed directly into Agrobacterium (Holsters et al. (1978) Mol Gen Genet 163:181-187). The selection marker gene permits the selection of transformed Agrobacteria and is, for example, the nptII gene, which imparts resistance to kanamycin. The Agrobacterium, which acts as host organism, should already contain a vir-region. The latter is required for transferring the T-DNA to the plant cell. An Agrobacterium thus transformed can be used for transforming plant cells.

Many strains of Agrobacteria are capable of transferring genetic material—for example a transgenic locus of the invention—, such as, for example, the strains EHA101 (pEHA101) (Hood E E et al. (1996) J Bacteriol 168(3): 1291-1301), EHA105(pEHA105) (Hood et al. 1993, Transgenic Research 2, 208-218), LBA4404(pAL4404) (Hoekema et al. (1983) Nature 303:179-181), C58C1 (pMP90) (Koncz and Schell (1986) Mol Gen Genet 204, 383-396) and C58C1(pGV2260) (Deblaere et al. (1985) Nucl Acids Res. 13, 4777-4788). Various binary vectors are known, some of which are commercially available such as, for example, pBIN19 (Clontech Laboratories, Inc. USA).

To transfer at least one transgenic locus of the invention to the plant cell, plant explants are co-cultured with Agrobacterium. Starting from infected plant material (for example leaf, root or stalk sections, but also protoplasts or suspensions of plant cells), intact plants can be regenerated using a suitable medium which may contain, for example, antibiotics or biocides for selecting transformed cells. The plants obtained can then be screened for the presence of the DNA introduced, in this case a transgenic locus of the invention. As soon as the DNA has integrated into the nuclear genome of the plant cell, the genotype in question is, as a rule, stable and the insertion in question is also found in the subsequent generations. Transformed plant cells, i.e. those which comprise at least one transgenic target locus, donor locus and/or nuclease locus integrated into the nuclear genome of the plant cell, can be selected from untransformed cells if a selectable marker is part of the introduced transgenic locus of the invention. As soon as a transformed plant cell has been generated, an intact plant can be obtained using methods known to a person skilled in the art. For example, callus cultures are used as starting material. The formation of shoots and roots can be induced in this as yet undifferentiated cell biomass in the known fashion. The shoots obtained can be planted and cultured. Transformed plant cells, derived by any of the above transformation techniques, can be cultured to regenerate a whole plant which possesses the transformed locus of the invention stably integrated in the nuclear genome. Such regeneration techniques typically rely on manipulation of certain phytohormones in a tissue culture growth medium, typically also relying on a selection marker which has been introduced together with the transgenic locus of the invention. Plant regeneration from cultured protoplasts is described in Evans et al., Protoplasts Isolation and Culture, Handbook of Plant Cell Culture, pp. 124176, Macmillian Publishing Company, New York (1983); and in Binding, Regeneration of Plants, Plant Protoplasts, pp. 21-73, CRC Press, Boca Raton, (1985). Regeneration can also be obtained from plant callus, explants, somatic embryos (Dandekar et al. (1989) J Tissue Cult Meth 12:145; McGranahan et al. (1990) Plant Cell Rep 8:512), organs, or parts thereof. Such regeneration techniques are described generally in Klee et al. (1987) Ann Rev Plant Physiol 38:467-486.

In a preferred embodiment of the invention at least one donor locus and at least one target locus are combined via crossing of plants. In case the rare cleaving nuclease is provided via an expression cassette for a rare cleaving nuclease located in a nuclease locus, it is possible to cross a plant comprising at least one target locus and comprising at least one nuclease locus with a plant comprising at least one donor locus, or to cross a plant comprising at least one target locus with a plant comprising at least one donor locus and at least one nuclease locus, or to co-transform at least one nuclease locus with at least one nuclease locus in a plant cell comprising at least one donor locus, of to co-transform at least one nuclease locus with at least one donor locus in a plant cell comprising at least one target locus.

Preferably the plant cell or plant is checked for integrity of the at least one target locus or the at least one donor locus or for integrity of the at least one target locus and the at least one donor locus, before such plant cells or plants are used for crossing to combine the at least one target locus and the at least one donor locus.

In a further embodiment of the invention, the plant cell or plant comprising at least one target locus and at least one donor locus is checked for integrity of the at least one target locus and the at least one donor locus before the rare cleaving nuclease used for induction of the homologous recombination is provided, e.g. by expression from a nuclease locus or a target locus or donor locus comprising an expression cassette for such rare cleaving nuclease.

Checked for integrity means in this context, that the at least one donor locus or the at least one target locus, preferably the at least one donor locus and the at least one target locus are checked for unwanted sequence truncations or mutations. Preferably, they are also checked for copy number and location of the integration sites. Information on the integration sites of the at least one target locus and the at least one donor locus, may be important to select plant cells or plants having a preferred location of the at least one target locus, which may be important for further breeding purposes, or to select plants or plant cells comprising at least one target locus and at least one donor locus on the same chromosome, or on homologous chromosomes or are located on homologous regions of otherwise non-homologous chromosomes, or to select plant cells or plants having a preferred proportion of target locus to donor loci, or a preferred proportion of target loci to donor locus, or a preferred proportion of target loci to donor loci.

In a further embodiment of the invention, the plant cell or plant comprising at least one target locus and at least one donor locus is checked for homozygosity of the at least one target locus or the at least one donor locus or the at least one target locus and the at least one donor locus before the rare cleaving nuclease used for induction of the homologous recombination is provided, e.g. by expression from a nuclease locus or a target locus or donor locus comprising an expression cassette for such rare cleaving nuclease.

Methods to check plant cells for integrity or homozygosity or integrity and homozygosity of any genomic sequence are available in the art and can readily applied to check for integrity or homozygosity or integrity and homozygosity of the target loci, donor loci, nuclease loci of the inventions as well as the loci produced by the homologous recombination between a target locus and a donor locus.

The methods for modifying a target locus in a plant cell being disclosed herein may comprise a further step in which double haploid cells are produced, in order to produce plant cells or plants being homozygous for at least one target locus or at least one donor locus, or being homozygous for at least one target locus and at least one donor locus.

Further Use of Plant Cells Comprising at Least One Recombined Target Locus:

The methods for modifying a target locus in a plant cell being disclosed herein may comprise a further step in order to grow, respectively regenerate, plants from these cells and to use them for further purposes, e.g. for breeding of new plant varieties or production of food or feed from these plants or from harvestable plant parts of these plants, like seeds, fruits, roots, tubers or biomass.

Accordingly, the current invention encompasses methods for modifying a target locus in a plant cell, comprising one ore more additional steps of growing plants or regenerating plant cells to a plant in which at least one target locus has been undergone homologous recombination with at least one donor locus, by recombining homologous region A of the at least one target locus with homologous region C of at least one donor locus and recombining homologous region B of the at least one target locus with homologous region D of the at least one donor locus. Preferable these plants are allowed to set seed or are used crossed with other plants. Preferably the seeds produced thereby are collected or harvested. Collected or harvested seeds may further be used to grow further generations of plants, which may be used in further crossings, which may be back-crossings, selfings, crossing to other plants, crossings for production of hybrid plants. Haploid cells of any of those plant generations may be used to produce double haploid plant cells or double haploid plants. Those further crossing steps or steps to produce double haploid plant cells or double haploid plants may also be used to eliminate superfluous or remaining target loci, donor loci, nuclease loci or remaining sequences which are produced at a former donor locus after homologous recombination or non-homologous-end-joining, being induced by cuts or nicks of at least one rare nuclease cutting site of such donor locus. Such remaining sequences are for example described by the new donor locus depicted in any one of FIG. 1, 2, 3, 4 or 14.

The methods and designs of donor loci, target loci and nuclease loci disclosed herein can be used, in principle, to modify any target locus for any purpose. However, they are especially utile when used to transfer a particular region X of a donor locus to the same genetic locus in different plant lines, for example to test its effect at the same modified target locus in different genetic backgrounds. Another application is to transfer one particular region X of a donor locus to alternative target loci in the same genetic background, in order to test its effect at different genomic locations or to compare the frequency of modification of different target loci, based on a constant proportion of target loci to donor loci, or to test the effect of modifications of individual members of gene families. Another application of the methods and donor loci, target loci and nuclease loci disclosed herein would be to test the effect of different regions X provided by different donor loci at the same target locus, e.g. to compare the effects of different gene variants or allelic genes at the same genetic location, or to determine different frequency of target locus modifications based on a constant proportion of donor loci to target loci. The methods and donor loci, target loci and nuclease loci disclosed herein to combine large region X with larger regions at the target locus, in order to create new linkage groups. This technology will be especially useful, to create or modify complex genetic networks, e.g. to modify signaling pathways or to modify metabolic pathways, thereby to avoiding repeated transformations, which will lead to independent genetic integration sites being are hard to control in following breeding applications, or repeated targeted integration approaches using single genes, or transformations with very large constructs, which will lead to instability problems during cloning and transformation of these constructs. Because many variations of the methods to modify a target locus disclosed herein rely rather on crossing of plants than on tissue culture techniques, they are especially suited to form part of crossing schemes usually employed by plant breeders to produce new plant varieties. A particular utile application of the methods disclosed herein is to integrate them in breeding schemes used to produce male-sterile or male fertile plant lines used in hybrid breeding.

Thus, a further application of the methods and designs of donor loci, target loci and nuclease loci disclosed herein is to produce plant lines for hybrid breeding, e.g. to produce male sterile breeding lines and male fertile breeding lines, by using target loci and or donor loci comprising an expression cassette for a functional or non-functional male fertility gene, in order to produce plant lines differing only in a functional or non-functional male fertility gene at the same genetic locus. Because many variations of the methods to modify a target locus disclosed herein rely rather on crossing of plants than on tissue culture techniques, they are also especially suited to be used for plant species or plant varieties which are hard to handle during transformation or plant regeneration. Another particular useful application of the methods of the invention is to use two or more donor loci comprising different regions X to modify a particular target locus. For example, to produce heterozygous genotypes at a particular genetic location, which comprise sequences, e.g. genes, having a complementary or synergistic effect. One example for those situations may be if, a par one region X of a recombined target locus comprises a toxic gene, e.g. Barnase, while an inhibitor of the lethal gene, e.g. Barstar, is transferred to the region of the allelic recombined target locus. The effect in future crossings would be that plant cells being homozygous for the lethal gene would be killed, while heterozygous plant cells or homozygous plant cells for the inhibitor of the lethal gene would be able to survive.

However, in some situations it is of advantage not to perform further crossings of plants, e.g. to preserve a particular genetic background of a certain plant, for example in plant species which are usually multiplied and marketed as clones, like many tuber crops, like potato, cassava or Jerusalem artichoke or other clonal multiplied and marketed plants, like fruit bearing trees, grapes, or sugar cane. In some cases it may even not be possible to perform further crossings because of sterility of the plants of interest. Such plants or for example triploidic variants of plant species, which occur for example, like banana, seedless watermelon, citrus, asparagus or beets.

Thus, in situations in which it is of advantage not to perform further crossings of plants, those methods of the invention are of particular advantage, which use one or more target loci comprising an expression cassette for a rare cleaving nuclease and/or an expression cassette for a selection marker, and/or an expression cassette for a HR modifying sequence located between homologous region A and homologous region B, or which use one or more donor loci, comprising an expression cassette for a rare cleaving nuclease and/or an expression cassette for a selection marker, and/or an expression cassette for a HR modifying sequence not being located between homologous region D and homologous region D, and preferably located between homologous region E and homologous region F, or which use one or more nuclease loci, comprising an expression cassette for a selection marker, and/or an expression cassette for a HR modifying sequence located between homologous region I and a homologous region J, or methods of the invention using co-transformation methods to provide transgenic loci of the invention.

Accordingly, methods used for the above described situations and purposes form also part of the invention.

Another embodiment of the invention are DNA constructs and plant chromosomes comprising one or more target loci, and/or one or more donor loci, and/or one or more nuclease loci, and/or one or more recombined loci, described above, as well as plant cells, plant nuclei, plant parts and plants comprising one or more target loci, and/or one or more donor loci, and or one or more nuclease loci, and/or one or more recombined loci. In an preferred embodiment of the invention the DNA constructs, plant chromosomes, plant cells, plant nuclei, plant parts and plants comprise one or more target loci, and/or one or more donor loci, and/or one or more nuclease loci, and/or one or more recombined loci, described in FIGS. 1 to 18, including the description of FIGS. 1 to 18. A further embodiment are plant chromosomes, plant cells, plant nuclei, plant parts and plants comprising a combination of target loci, donor loci and/or nuclease loci as described in FIGS. 19 to 22, including the description of FIGS. 19 to 22.

Figure 15:
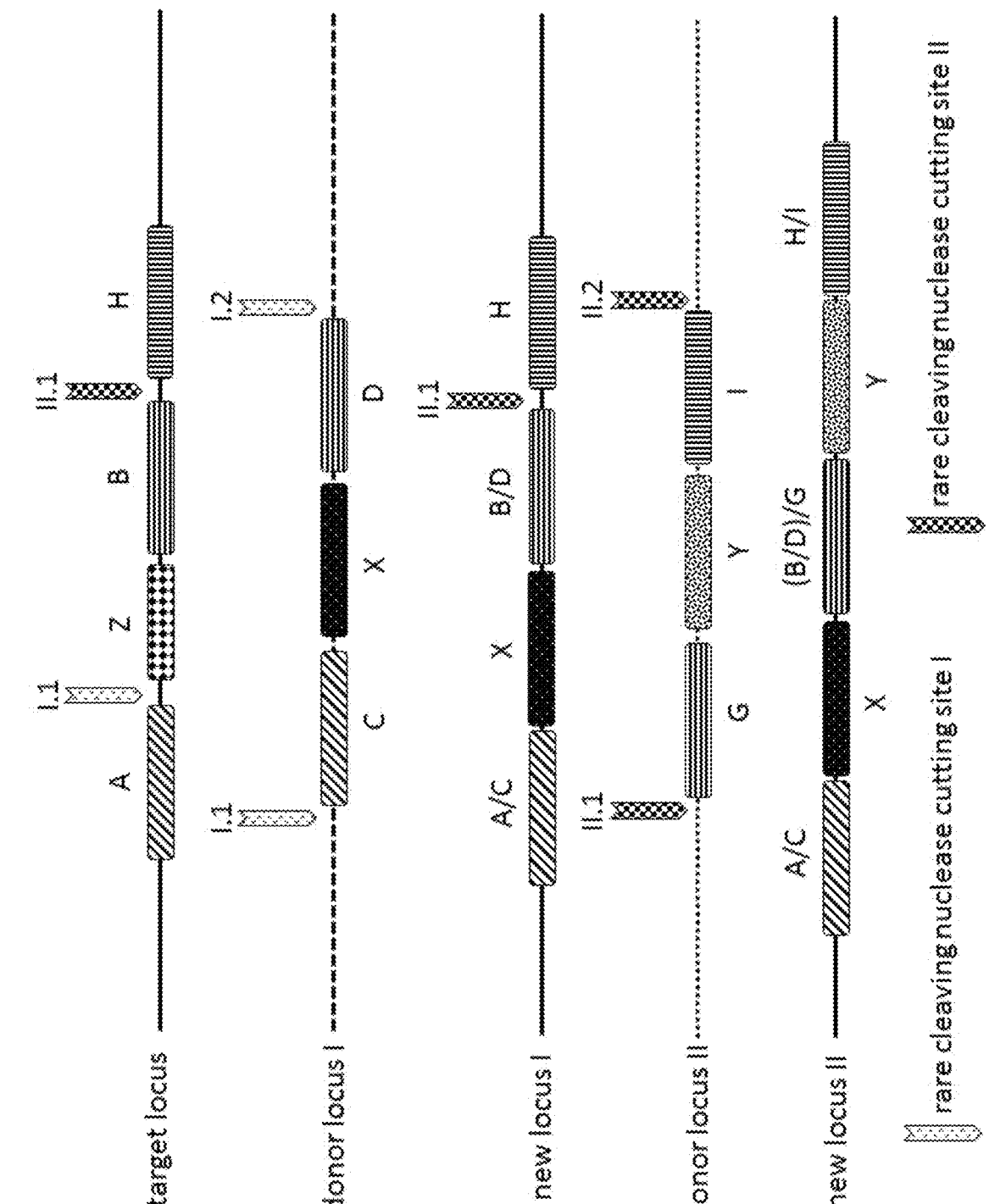
FIG. 15 depicts a schematic diagram of a method to stack polynucleotide sequences at one target locus and exemplary designs of a target locus and two different donor loci (donor locus I and donor locus II) as well as a new locus I as intermediate step to reach a design as depicted for new locus II of FIG. 15. The target locus comprises a homologous region A and a homologous region B, as well as a region Z and a rare cleaving nuclease cutting site for a first rare cleaving nuclease (I.1). Thus, the target locus of FIG. 15 comprises all elements as the target locus described for FIG. 1. In addition to that, the target locus of FIG. 15 comprises an additional homologous region H, has sufficient sequence identity to allow for homologous recombination with homologous region I of donor locus II. The target locus of FIG. 15 comprises also an additional rare cleaving nuclease cutting site (II.1), being located between homologous region H and homologous regions A and B, but not between homologous region A and homologous region B. The target locus of FIG. 15 is used in combination with a donor locus I, comprising all elements as described for the donor locus of FIG. 1, and a rare cleaving nuclease, which is able to nick or cut the rare cleaving nuclease cutting site I.1, but does not nick or cut the rare cleaving nuclease cutting site II.1 or nicks or cuts the rare cleaving nuclease cutting site II.1 at a lower frequency if compared to the frequency of nicks or cuts at the rare cleaving nuclease cutting site I.1. After homologous recombination between homologous region A and homologous region C as well as homologous recombination between homologous region B and homologous region D a new locus is created (new locus I), comprising the resulting sequences of homologous recombination between homologous region A and homologous region C (homologous region A/C) and homologous recombination between homologous region B and homologous region D, being homologous region B/D. The new locus I comprises also homologous region H and the rare cleaving nuclease cutting site II.1 already described above. Following this, new locus I is used in combination with donor locus II, comprising a homologous region G having sufficient sequence identity to homologous region B/D to allow for homologous recombination between homologous region G and homologous region B/D and a homologous region I having sufficient sequence identity to homologous region H to allow for homologous recombination between homologous region I and homologous region H. Donor locus II comprises also a region Y and one, two or more rare cleaving nuclease cutting sites (II.1 and II.2) located close to homologous region G or homologous I, preferably located close to homologous region G and homologous region 1, but not located between homologous region G and homologous region I. After a rare cleaving nuclease being able to cut rare cleaving nuclease cutting sites (II.1 and II.2) has been provided and homologous recombination between homologous regions B/D and G and homologous regions H and I has been induced, a new locus II is created, comprising homologous region A/C, region X, homologous region (B/D)/G, region Y and homologous region H/I, wherein homologous region (B/D)/G is the resulting sequence after homologous recombination between homologous region B/D and homologous region G and homologous region H/I is the resulting sequence after homologous recombination between homologous region H and homologous region 1.
Figure 16:
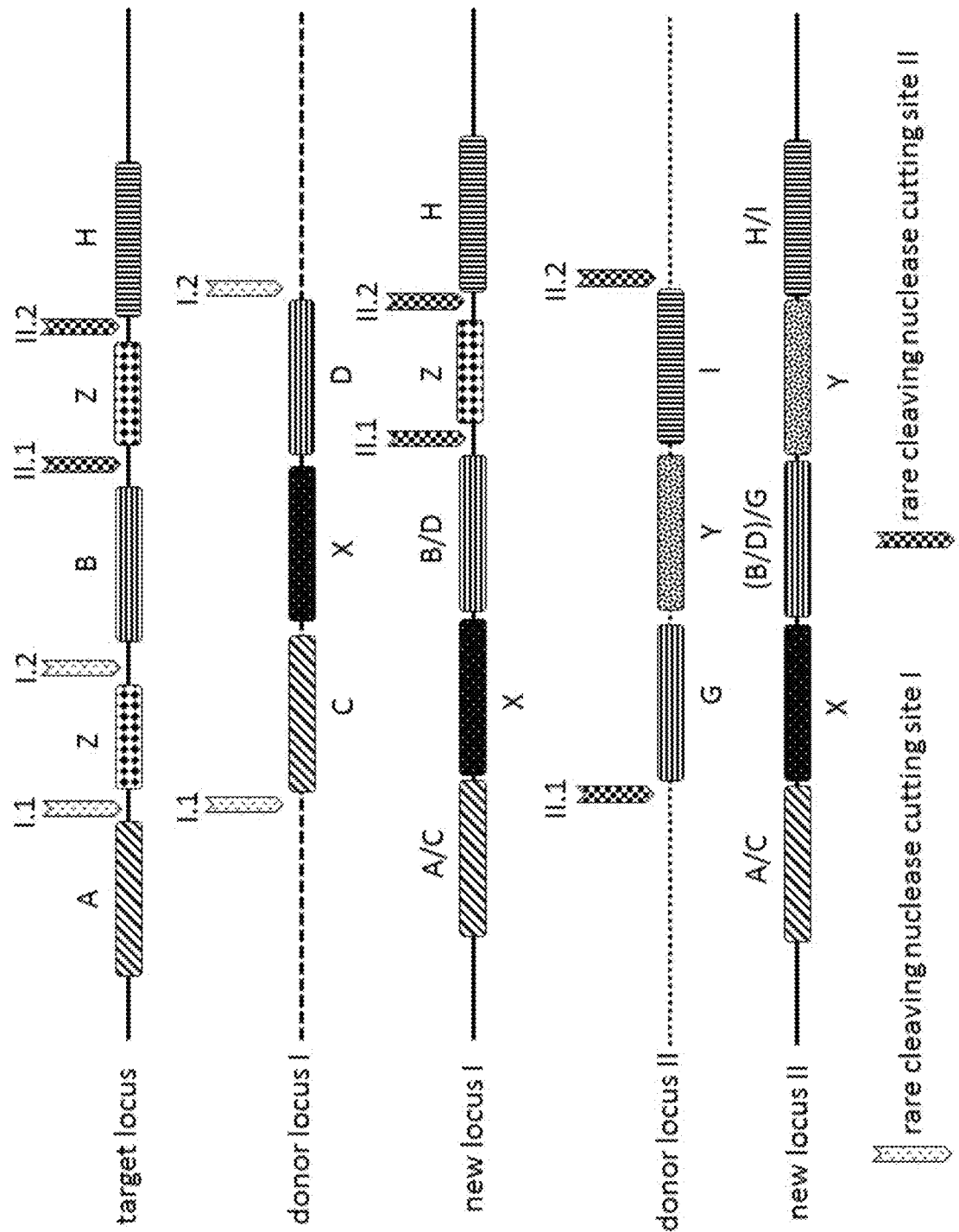
FIG. 16 depicts a schematic diagram of a method to stack polynucleotide sequences at one target locus and exemplary designs of a target locus and two different donor loci (donor locus I and donor locus II) as well as a new locus I as intermediate step to reach a design as depicted for new locus II quite similar to the method and designs described by FIG. 15. Donor locus I and donor locus II as well as new locus II of FIG. 16 have an identical design to donor locus I, donor locus II and new locus II of FIG. 15. The target locus of FIG. 16 differs from the target locus of FIG. 15 by having two regions Z, one located between homologous regions A and B and another one located between homologous regions B and H. The polynucleotide sequence of these two regions Z may or may not be identical. The target locus of FIG. 16 comprises also one, two or more rare cleaving nuclease cutting sites (I.1 and I.2) which are located between homologous region A and homologous region B and are suited to be nicked or cut by a first rare cleaving nuclease. In addition to that, the target locus of FIG. 16 comprises also one, two or more rare cleaving nuclease cutting sites (II.1 and II.2) which are located between homologous region B and homologous region H and are suited to be nicked or cut by a second rare cleaving nuclease. After induced homologous recombination with donor locus I, the design of the target locus of Figure II will result in a different design of new locus I, if compared to the new locus I of FIG. 15. New locus I of FIG. 16 comprises a remaining region Z, located between homologous region B/D and homologous region H. After induced homologous recombination between new locus I and donor locus II, a new locus II is created which has an identical design to the new locus II of FIG. 15.
Figure 17:
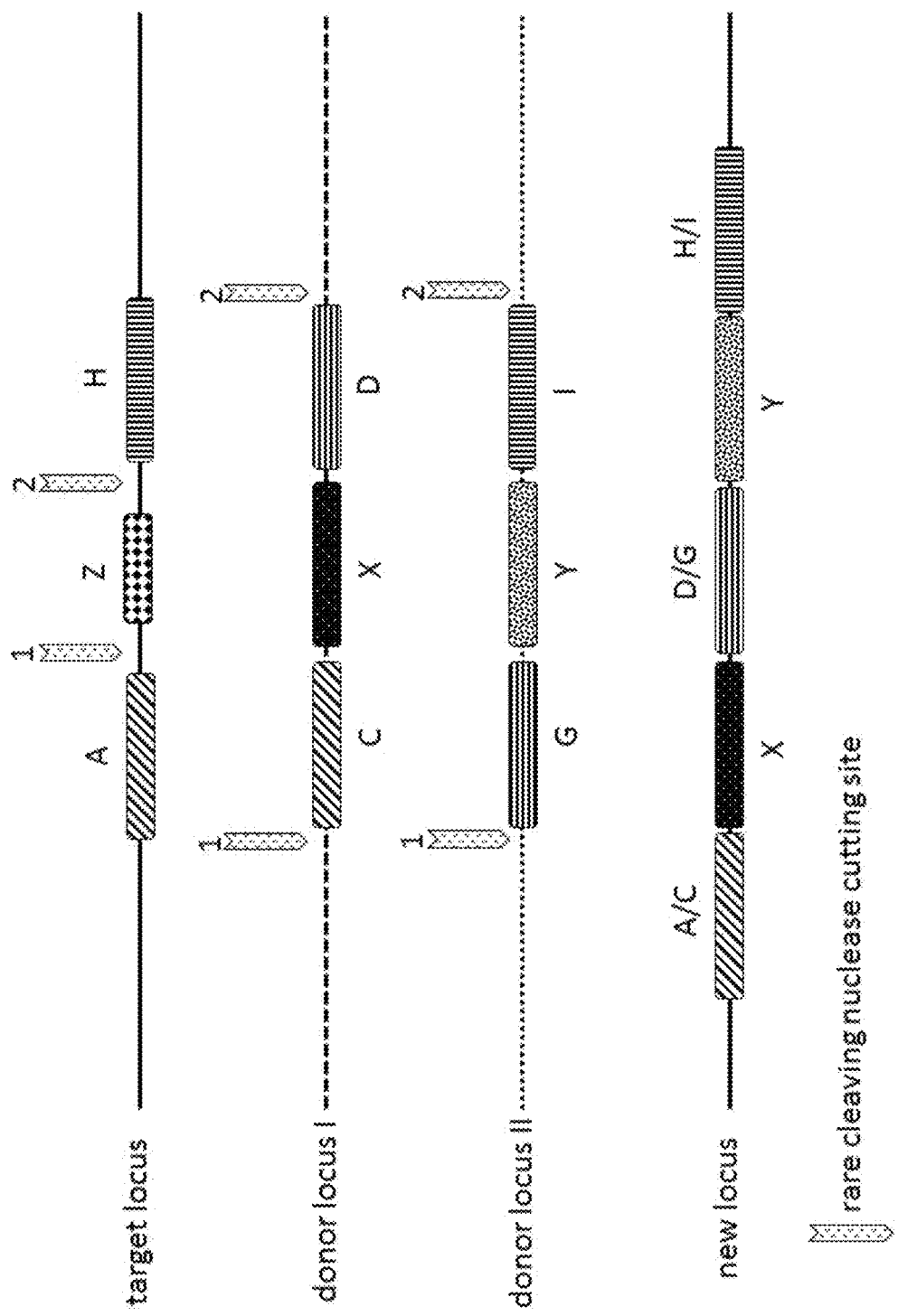
FIG. 17 depicts a schematic diagram of a method to stack polynucleotide sequences at one target locus and exemplary designs of a target locus and two different donor loci (donor locus I and donor locus II). The target locus comprises a homologous region A and a homologous region H, a region Z and one, two or more rare cleaving nuclease cutting sites located between homologous region A and homologous region H. Donor Locus I comprises a homologous region C, a region X and a homologous region D, as well as one, two or more rare cleaving nuclease cutting sites, located close to homologous region C or homologous region D or close to homologous region C and homologous region D, but not between homologous region C and homologous region D. Donor locus II comprises a homologous region G, a region Y and a homologous region I, as well as one, two or more rare cleaving nuclease cutting sites, located close to homologous region G or homologous region I or close to homologous region G and homologous region I, but not between homologous region G and homologous region I. The homologous region A has sufficient sequence identity to homologous region C to allow for homologous recombination between these regions, likewise, homologous region D has sufficient sequence identity to homologous region G to allow for homologous recombination between each other. Further, homologous region H has sufficient sequence identity to homologous region I to allow for homologous recombination between these sequences. After a rare cleaving nuclease, being able to nick or cut the rare cleaving nuclease cutting sites of the target locus, donor locus I and donor locus II, has been provided, the induced homologous recombination results in recombination between homologous region A and homologous region C, homologous region D and homologous region G and homologous region H and homologous region I, resulting in the design of the new locus, comprising the region X of former donor locus I and region Y of former donor locus II, as well as homologous region A/C, being the result of homologous recombination between homologous regions A and C, and homologous region D/G, being the result of homologous recombination between homologous regions D and G, and homologous region H/I, being the result of homologous recombination between homologous regions H and I.
Figure 18:
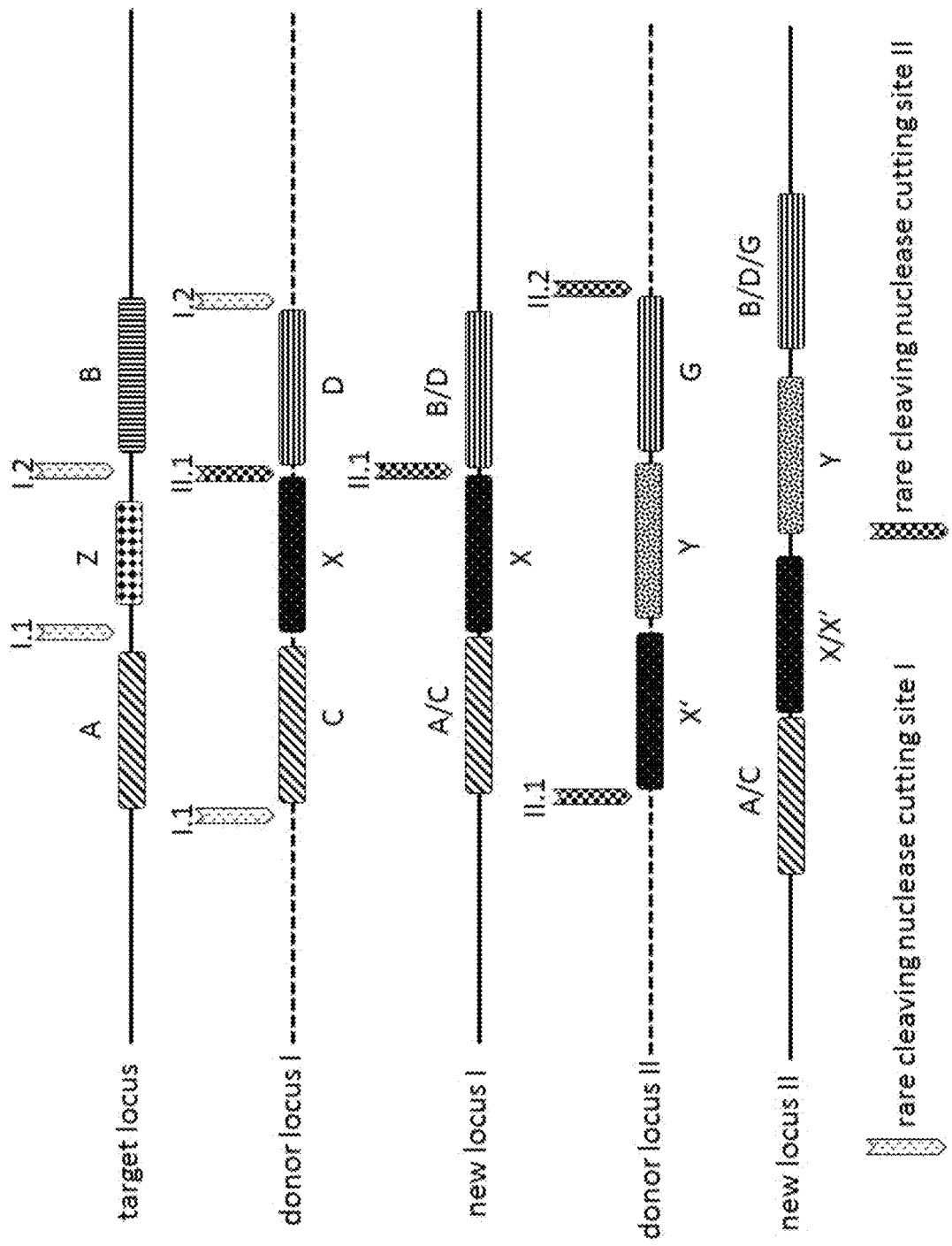
FIG. 18 depicts a schematic diagram of a method to stack polynucleotide sequences at one target locus and exemplary designs of a target locus and two different donor loci (donor locus I and donor locus II). The target locus of FIG. 18 comprises all elements of the target locus of FIG. 4, while the donor locus I of FIG. 18 comprises all elements of the donor locus of FIG. 2 and one, two or more additional rare cleaving nuclease cutting sites (II.1) located between homologous region C and homologous region D, which can be nicked or cut by a second rare cleaving nuclease, which is not able to nick or cut the rare cleaving nuclease cutting sites of a first rare cleaving nuclease (I.1 and I.2), or nicks or cuts the rare cleaving nuclease cutting site I.1 and I.2 at a lower frequency if compared to the frequency of nicks or cuts at the rare cleaving nuclease cutting site II.1. After a first rare cleaving nuclease, which is able to nick or cut the rare cleaving nuclease cutting 1.1 and I.2, but does nor nick or cut the rare cleaving nuclease cutting sites of the second rare cleaving nuclease (II.1), or nicks or cuts the rare cleaving nuclease cutting sites 1.1 and I.2 at a higher frequency if compared to the frequency of nicks or cuts at the rare cleaving nuclease cutting sites of the second rare cleaving nuclease, has been provided, a homologous recombination reaction is induced, which results in homologous recombination between homologous region A and homologous region C and between homologous region B and homologous region D, resulting in homologous region A/C and homologous region B/D. The resulting new locus I comprises homologous region A/C and homologous region B/D, as well as region X and the rare cleaving nuclease cutting sites of former donor locus I. The new locus I is then used in combination with donor locus II, which comprises a homologous region X' which has sufficient sequence identity to region X of the new locus I to allow for homologous recombination between each other. Donor locus II does also comprise a region Y, a homologous region G and one, two or more rare cleaving nuclease cutting sites, which can be nicked or cut by a second rare cleaving nuclease. Homologous region G has sufficient sequence identity to homologous region B/D to allow for homologous recombination between these two sequences. After a second rare cleaving nuclease has been provided, the rare cleaving nuclease cutting sites of the new locus I and the donor locus II will be nicked or cut and a homologous recombination reaction will be induced. This reaction will recombine homologous region X and X' thereby producing a homologous region X/X' and will recombine homologous region B/D with homologous region G, resulting in homologous region B/D/G, thereby producing new locus II, which comprises homologous region A/C, homologous region X/X', region Y and homologous region B/D/G.
Figure 19:
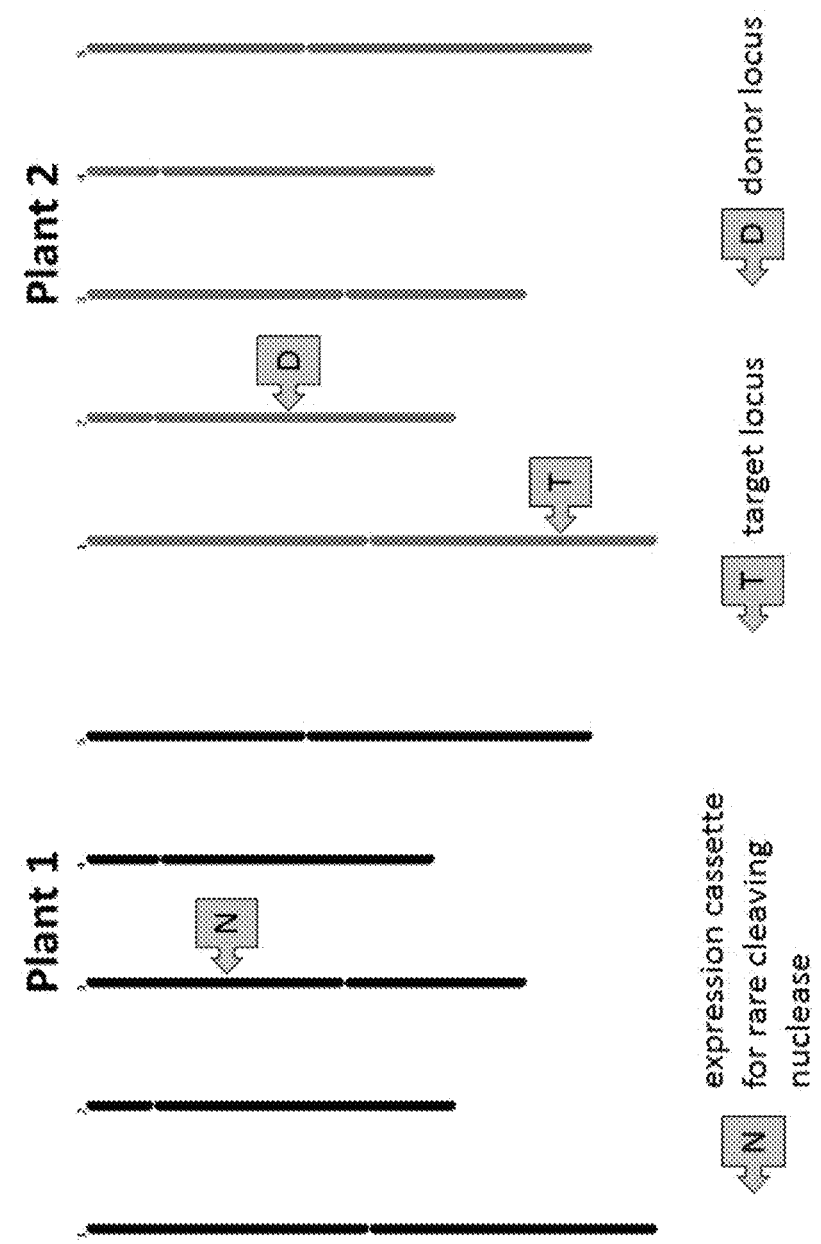
FIG. 19 depicts the nuclear genome of two exemplary plant cells, one plant cell of Plant 1 and one plant cell of Plant 2. Both plant cells comprise five chromosomes. The plant cell of Plant 1 comprises an expression cassette for a rare cleaving nuclease located on one chromosome. The plant cell of Plant 2 comprises at least one target locus and at least one donor locus located on the chromosomes of the plant cells. The at least one target locus and the at least one donor locus may have any design of a target locus or donor locus described herein, as long as the at least one donor locus comprises a homologous region C and a homologous region D, which have sufficient sequence identity to a homologous region A and a homologous region B of the at least one target locus in order to allow for homologous recombination between homologous region A and homologous region C and homologous region B and homologous region C, respectively, after homologous recombination has been induced by a nick or cut, of one or more rare cleaving nuclease cutting sites comprised in the at least one target locus and/or located in the at least one donor locus, by a nuclease provided via the expression cassette for a rare cleaving nuclease of the plant cell of Plant 1. This rare cleaving nuclease can be provided by fusion of the plant cell of Plant 1 and a plant cell of Plant 2 or by forming a zygote of a plant cell of Plant 1 and a plant cell of Plant 2.
Figure 20:
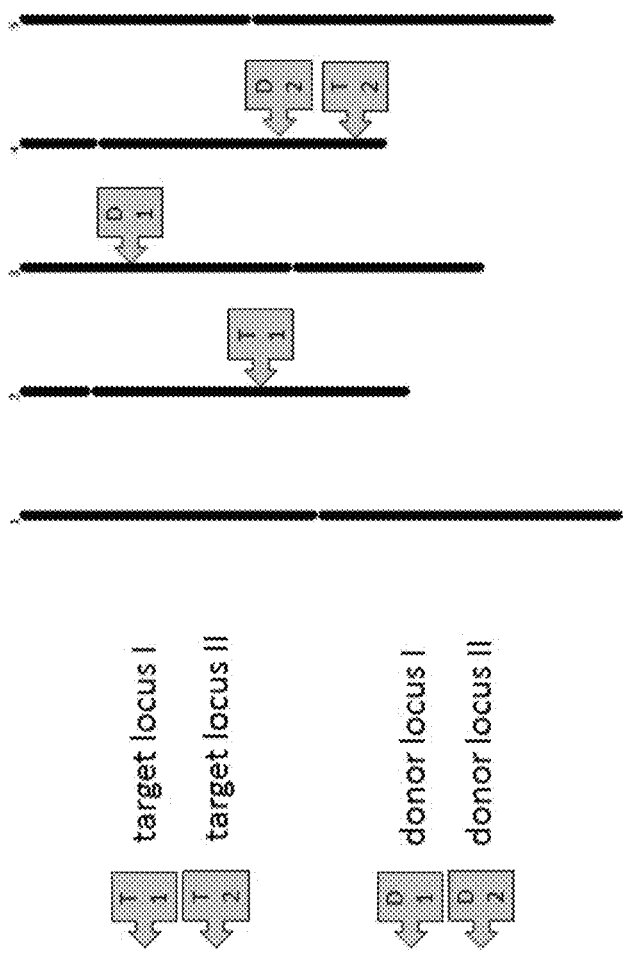
FIG. 20 depicts a nuclear genome of a plant cell having several chromosomes as well as at least two target loci (target locus I and target locus II) and at least two donor loci (donor locus I and donor locus II) located at different locations in the nuclear genome. The at least two target loci and the at least two donor loci may have any design of a target locus or donor locus described herein, as long as the donor loci comprise a homologous region C and a homologous region D, which have sufficient sequence identity to a homologous region A and a homologous region B of the target loci, in order to allow for homologous recombination between homologous region A and homologous region C and homologous region B and homologous region C, respectively. The target loci may have the same design, or may have different designs. The donor loci may have the same design or may have different designs as well. The target loci may even be identical in sequence, e.g. being multiple inserts of the same transgene. The same may be true for the donor loci.
Figure 21:
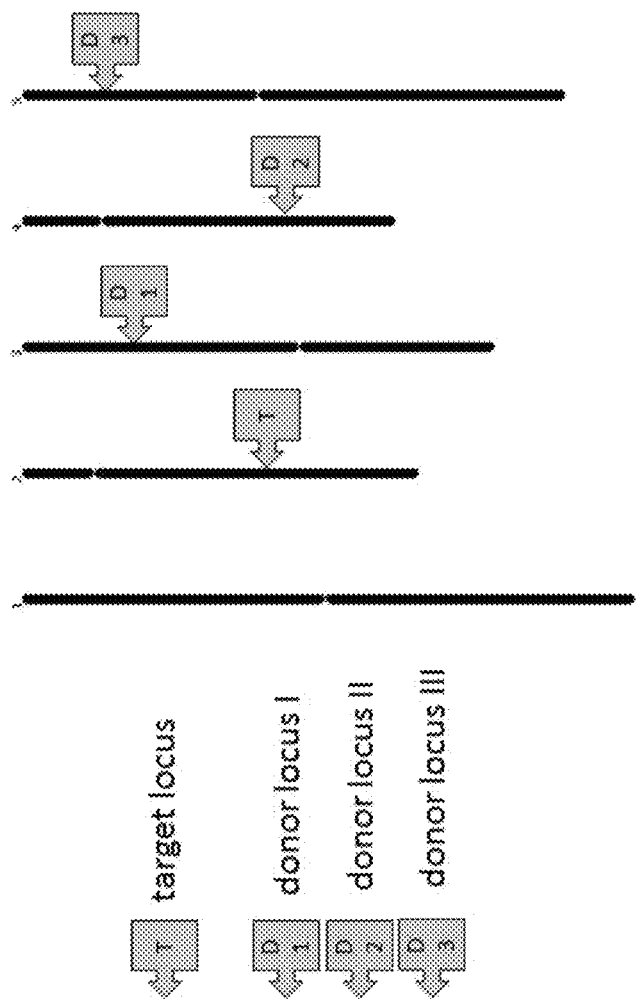
FIG. 21 depicts a nuclear genome of a plant cell having several chromosomes as well as at least one target locus (target locus I) and two or more donor loci (donor locus I, donor locus II and donor locus III) located at different locations in the nuclear genome. The different donor loci may represent multiple copies of the same insert, or represent donor loci having a different sequence e.g. having a different region X, but having homologous regions C and D, which all allow for homologous recombination with homologous regions A and B of the target locus.
Figure 22:
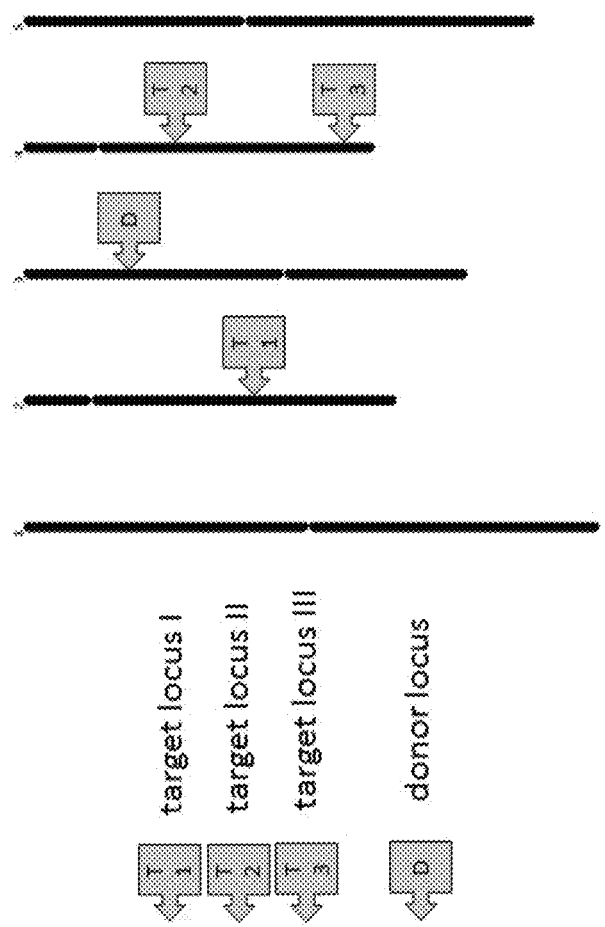
FIG. 22 depicts a nuclear genome of a plant cell having several chromosomes as well as two or more target loci (target locus I, target locus II and target locus III) located at different locations in the nuclear genome, but only one donor locus (donor locus I). The target loci may represent multiple copies of the same insert, or represent target loci having a different sequence e.g. having a different region Z, but having homologous regions A and B, which all allow for homologous recombination with homologous regions C and D of the donor locus I.

An additional embodiment of the invention are methods for gene stacking as described by FIGS. 15, 16 and 18, including the description of FIGS. 15, 16, and 18.

A further embodiment of the invention are plant chromosomes, plant cells, plant nuclei, plant parts and plants produced by any one of the methods described herein.

EXAMPLES

T-DNA Constructs

The DNA construct comprising the target locus, VC-SBT359-6qcz, contains the following elements from LB to RB: 35SpA[AS] (polyadenylation signal of the CaMV 35S gene in antisense orientation)—DsRed2[AS] (coding sequence (cds) of the DsRed2 fluorescent protein in antisense orientation)—bidirectional promoter (OAS/FD promoter: genomic DNA sequence located between the *Arabidopsis* Ferredoxin and O-acetyl-serine genes, able to drive expression of both flanking ORFs. In this construct it is driving the expression of the DsRed and the Npt2 genes)—Npt2 (kanamycin-resistance gene)—CatpA (polyadenilation signal of the *Solanum tuberosum* cathepsin D gene)—US (truncated, non-functional fragment of the GUS gene lacking part of the 5' end of the cds)—NOS terminator (terminator of the *Agrobacterium tumefasciens* nopaline synthase gene). The different elements were cloned into a binary vector backbone using standard molecular biology techniques and validated by sequencing.

The donor construct, VC-SBT366-12qcz, contains a phosphinotricin resistance expression cassette next to the LB followed by a targeting cassette. The phosphinotricin expression cassette consist of the NOS promoter (promoter of the of the *Agrobacterium* tumefasciens nopaline synthase gene), the pat cds (phosphinotricin acetyltransferase gene from *Streptomyces viridochromogenes*) and the NOS terminator (terminator of the *Agrobacterium tumefasciens* nopaline synthase gene).

The DNA construct comprising the donor locus contains the following elements: SP (superpromoter: reference Ni, M., Cui, D., Einstein, J., Narasimhulu, S., Vergara, C. E., and Gelvin, S. B. (1995). Plant J. 7, 661-676)—ZsGree (truncated, non-functional fragment of the Zoanthus sp. Green fluorescent protein gene missing 94 bp at the 3' end of the cds)—35SpA[AS] (polyadenilation signal of the CaMV 35S gene in antisense orientation)—DsRed2[AS] (cds of the DsRed2 fluorescent protein in antisense orientation)—pLEB4[AS] (seed-specific promoter of the *Vicia faba* legumin B4 gene)—35S promoter (promoter of the of the CaMV 35S gene)—GU (truncated, non-functional fragment of the GUS gene lacking part of the 3' end of the coding sequence)—een (truncated, non-functional fragment of the Zoanthus sp. Green fluorescent protein gene missing 9 bp at the 5' end of the cds)—LB3UT (terminator of the *Vicia faba* legumin 1B3 gene). The different elements were cloned into a pSUN3 backbone using standard molecular biology techniques and validated by sequencing.

A codon optimized I-SceI-open reading frame driven by the Petroselinum crispum Ubiquitin4-2 promoter was cloned in the binary vector pPZP221 (Kawalleck etas., 1993).

The three resulting binary vectors were electroporated into *Agrobacterium* strain GV3101 for plant transformation.

Plant Transformation

*Agrobacterium*-mediated transformation of *Arabidopsis* plants (Columbia-0 background) was performed with the floral dip protocol as described by Clough and Bent (1998). Plants resistant to the selection applied (target locus: kanamycin, donor locus: phosphinotricin and for the Ubi:: I-SceI nuclease locus: gentamycin) were checked for a 3:1 segregation in the next generation to obtain lines in which the transgene was only inserted at a single locus. Single copy plant lines were identified by Southern blot analysis and further characterized to assure that only lines with an intact T-DNA were used for further analysis. Insertion junctions were determined using the SiteFinder (Tan et al., 2005), inverse PCR (Ochman et al., 1988; Triglia et al., 1988) or Adapter ligation-mediated PCR protocol (O'Malley et al., 2007).

β-Glucuronidase Assay

β-glucuronidase assays to determine the recombination frequencies per plant and for analysis of segregation of the recombined locus were performed as described (Orel et al, 2003). Determination of GT events that entered the germline were carried out with 10 days old seedlings (F2'-generation), cultured on sand as described (Davis et al, 2009). After 14 days the seedlings were covered with a staining solution as described by Orel et al., 2003 except for sodium azide and incubated over night at room temperature. Plants with bluish roots were first transferred to agar plates and some days later to soil. Identification of recombinants for Southern blotting and PCR analysis was done with plants cultivated on GM medium (F3'-generation).

Plant DNA Extraction and Southern Analysis

DNA was extracted from a batch of 60 F3' siblings representing the progeny of the respective recombinant F2' plant. DNA extraction from plants was done as described (Salomon und Puchta, 1998). Southern blotting of EcoRI, HindIII or MfeI-digested DNA (F3' generation) using the hybridization membrane "Hybond N+" (GE Healthcare Europe GmbH, Freiburg, Germany) was performed as described (Salomon und Puchta, 1998). The DNA probes were labeled as described (Pacher et al., 2007). As DNA templates probe A was isolated by PCR using the oligonucleotides 5'-GTT GTG GGA GGT GAT GTC-3' (SEQ ID NO: 14) and 5'-CCG AGA ACG TCA TCA CCG-3' (SEQ ID NO: 15), probe B using the oligonucleotides 5'-CTT GGA TTG AAC AAG ATG GAT TGC-3' (SEQ ID NO: 16) and 5'-CAG AAG AAC TCG TCA AGA AGG CG-3' (SEQ ID NO: 17) and the kanamycin-specific probe using the oligonucleotides 5'-CTA GAT TCG ACG GTA TCG ATA AGC-3' (SEQ ID NO: 18) and 5'-GAT TGG TTA TGA AAT TCA GAT GC-3' (SEQ ID NO: 19). As template VC-SBT359-6qcz was used for probe A and the kanamycin probe, VC-SBT366-6qcz was used for probe B, respectively. Hybridizations were performed at 60° C.

PCR and Sequence Analysis

Genomic DNA (F3' generation) was analyzed by PCR using the oligonucleotides 5-GAC CAC TTC GTA CAA CAC TAG-3' (SEQ ID NO: 20) and 5"-CTA CTA ATC ATC ATC TAT CTG TG-3' (SEQ ID NO: 21) for detection of the upstream HR-mediated integration of the GT cassette and subsequent sequencing. Oligonucleotides 5"-GTT CAT TTC ATT TGG AGA GG-3' (SEQ ID NO: 22) and 5"-GAC GAC CAA AGC CAG TAA AG-3" (SEQ ID NO: 23) were used to amplify the restored GUS gene and sequencing. Oligonucleotides 5'-CAC TAG TCT AGA GTC GAT CGA C-3' (SEQ ID NO: 24) and 5'-GGG CAA TGC AGA TCC GGA TGC-3' (SEQ ID NO: 25) were used to amplify the restored donor region and sequencing. PCR reactions and sequencing were done as described (Hartung und Puchta, 2000).

Figure 23:
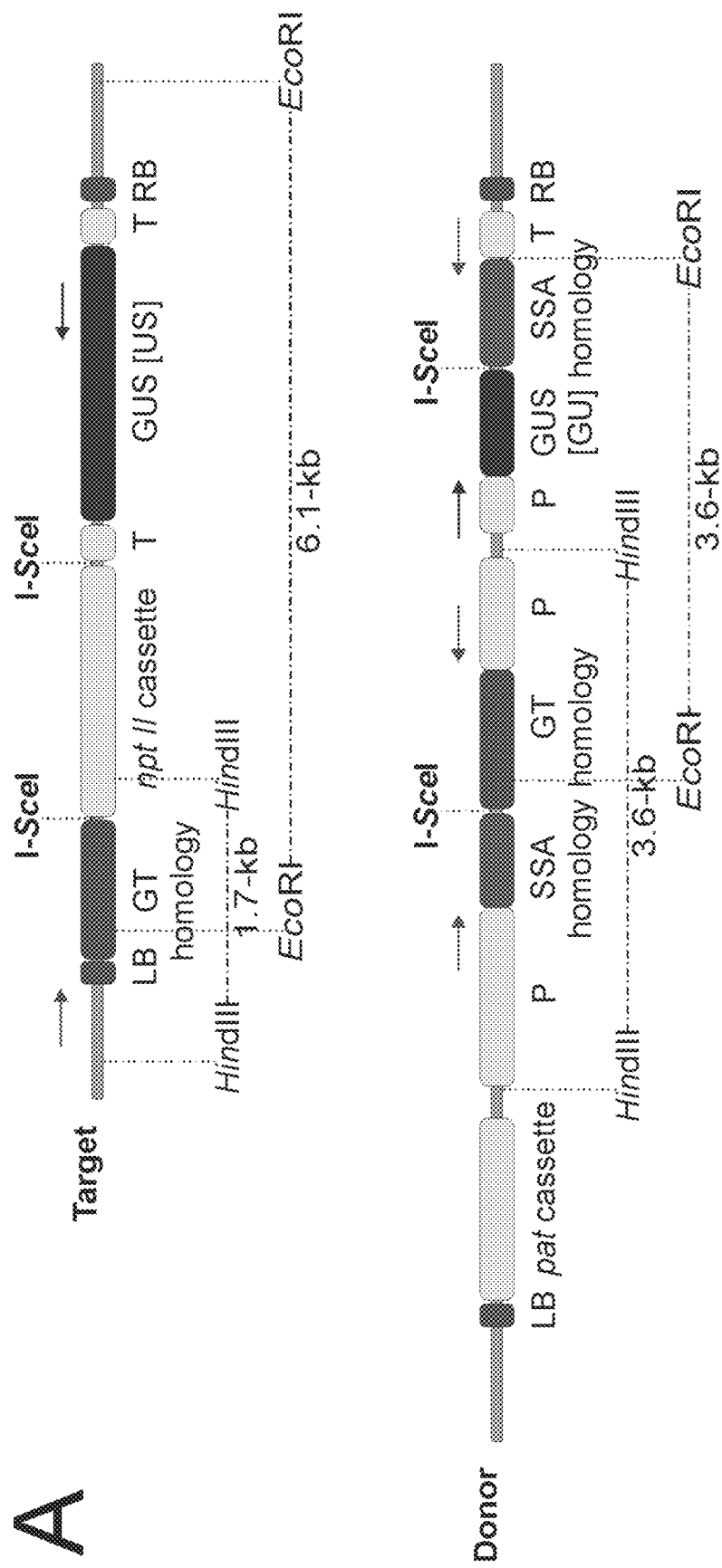
FIG. 23 depicts a schematic representation of the T-DNA constructs used to provide the donor locus and target locus, respectively to the nuclear genome of the plant cells. Target and donor T-DNA carry each two I-SceI recognition sites flanking the donor locus or a kanamycin-resistance cassette (region X) of the target locus. The target locus contains a truncated beta-glucuronidase gene (GUS [US]) that can be restored via homologous recombination subsequent to DNA double strand break induction at two I-SceI recognition sites that are flanking the kanamycin resistance gene (npt II cassette). The DNA fragment able to complement the truncated beta-glucuronidase gene of the target locus, is a truncated beta-glucuronidase gene (GUS [GU]) comprising a promoter (P) and being located between two I-SceI recognition sites of the donor locus. The regions "SSA homology" of the donor locus comprise sufficient sequence identity to allow for homologous recombination between each other after DNA double strand break induction. The same is true for the region "GT-homology" of the target locus and the "GT-homology" region of the donor locus. The regions "LB" and "RB" represent the left and right border region of the T-DNA of the target and donor loci constructs.
Figure 24:
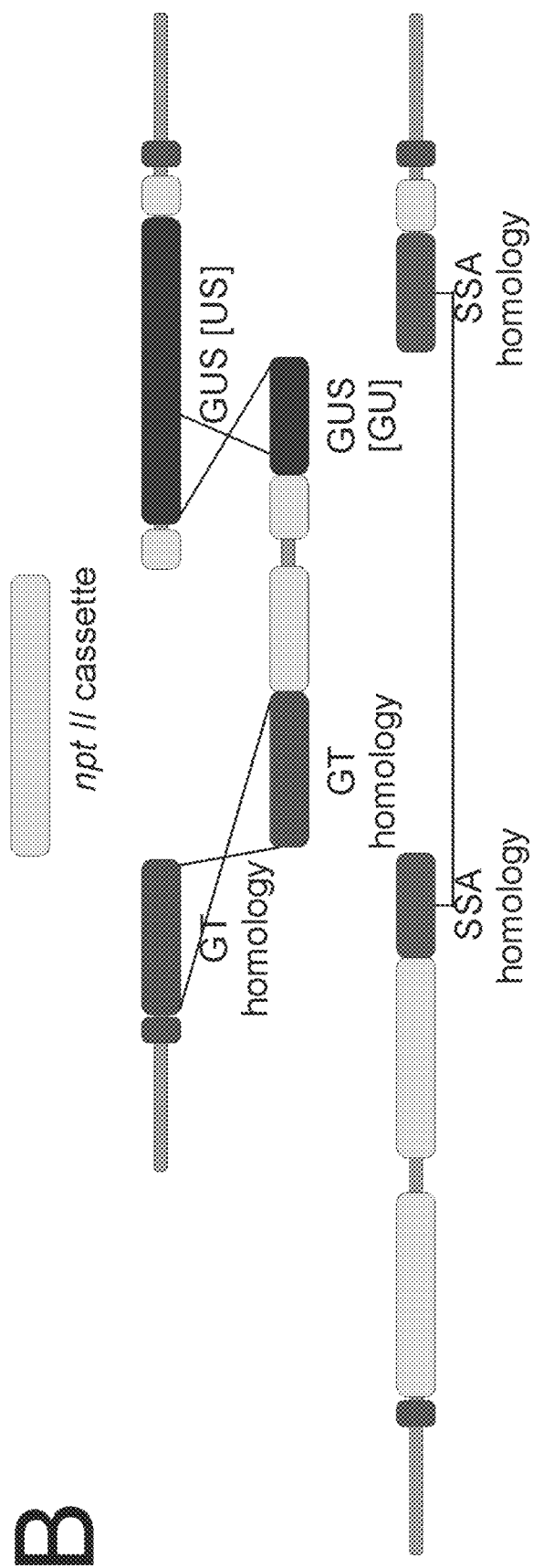
FIG. 24 depicts an intermediate stage of the donor and target loci depicted in FIG. 23 after DNA double strand break induction at the I-SceI recognition sites. The ntp II cassette (region Z) of the target locus is lost, while regions "GT-homology" and "GUS [GU]" and "GUS [US]" as well as regions "SSA homology" undergo homologous recombination.
Figure 25:
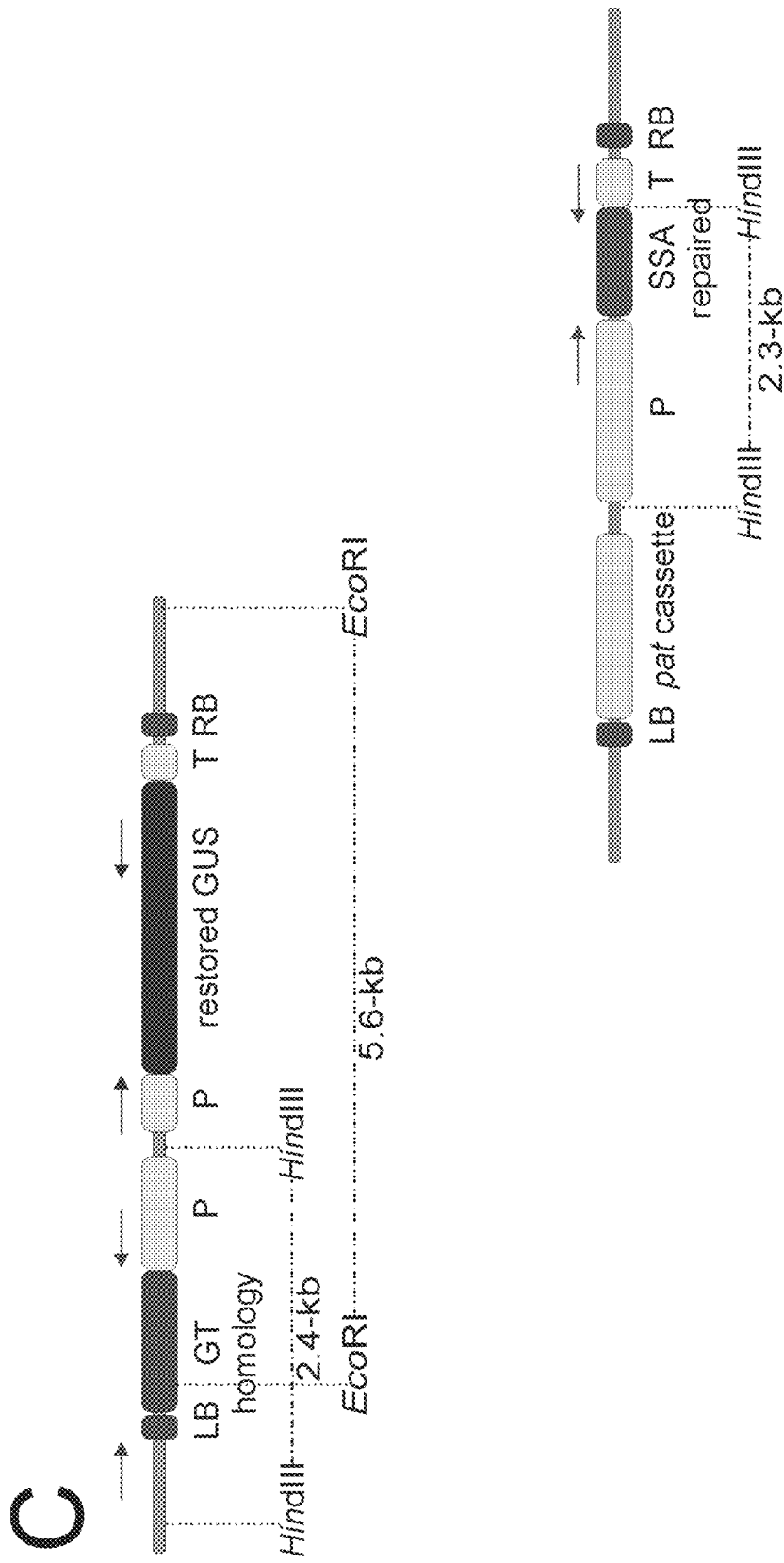
FIG. 25 depicts an the final stage of the donor and target loci depicted in FIG. 23 after homolgous recombination depicted in FIG. 24. The new locus created at the former target locus comprises a restored beta-glucuronidas gene (GUS) that can be detected via histochemical staining, while the new donor locus comprises a repaired SSA region.

Plant Experiments:

The in planta gene targeting system is based on two different constructs (FIG. 23) that were established independently by *Agrobacterium tumefaciens*-mediated transformation. The target locus contains a truncated β-glucuronidase gene (GUS) that can be restored via TE subsequent to DSB induction at two I-SceI recognition sites that are flanking a kanamycin resistance gene. Following DSB induction the kanamycin marker would be excised, thus activating the target for homologous recombination (FIG. 24). The donor locus contains the region X that is also flanked by two I-SceI recognition sites releasing the linear donor locus after I-SceI expression. Homology between the activated target site and the released donor locus is on one end 942 bp and on the other end 614 bp, respectively. Upstream and downstream of the I-SceI sites 599 bp of sequence homology were placed within the donor locus DNA construct so that after excision of the linear donor locus the resulting DNA-double strand break (DSB) could be repaired either by NHEJ or by single-strand annealing using this homology. Single copy lines for each construct were generated (four for the target, three for the donor) and crossed in all possible combinations of target/donor loci. Subsequently, lines homozygous for both constructs were established. Then, the I-SceI expression plant line Ubi::I-SceI #10 was crossed with all 12 different target/donor lines and the F1' generation was screened for somatic DSB-induced GT events which can easily be visualized as blue sectors after histochemical staining.

Figure 26:
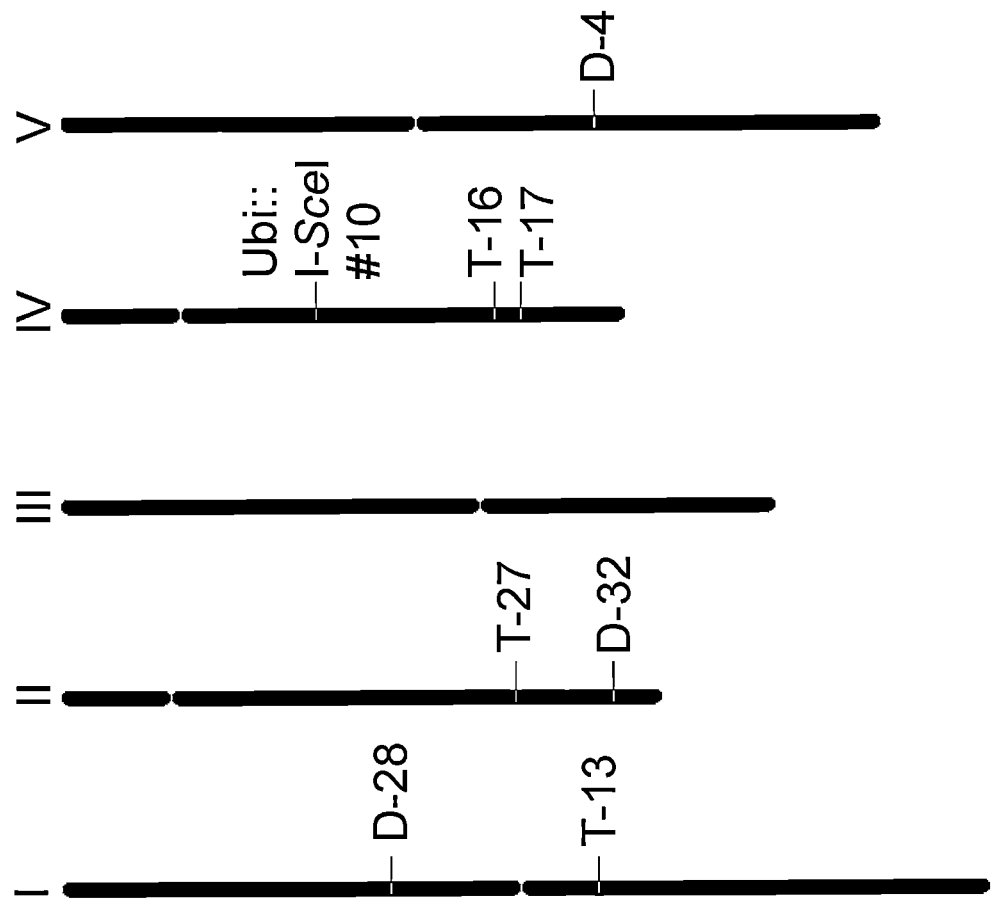
FIG. 26 depicts the genomic location of donor loci (D4, D28, D32) and the different genomic location of the target loci (T13, T16, T17, T27) used in the Examples described below.
Figure 27:
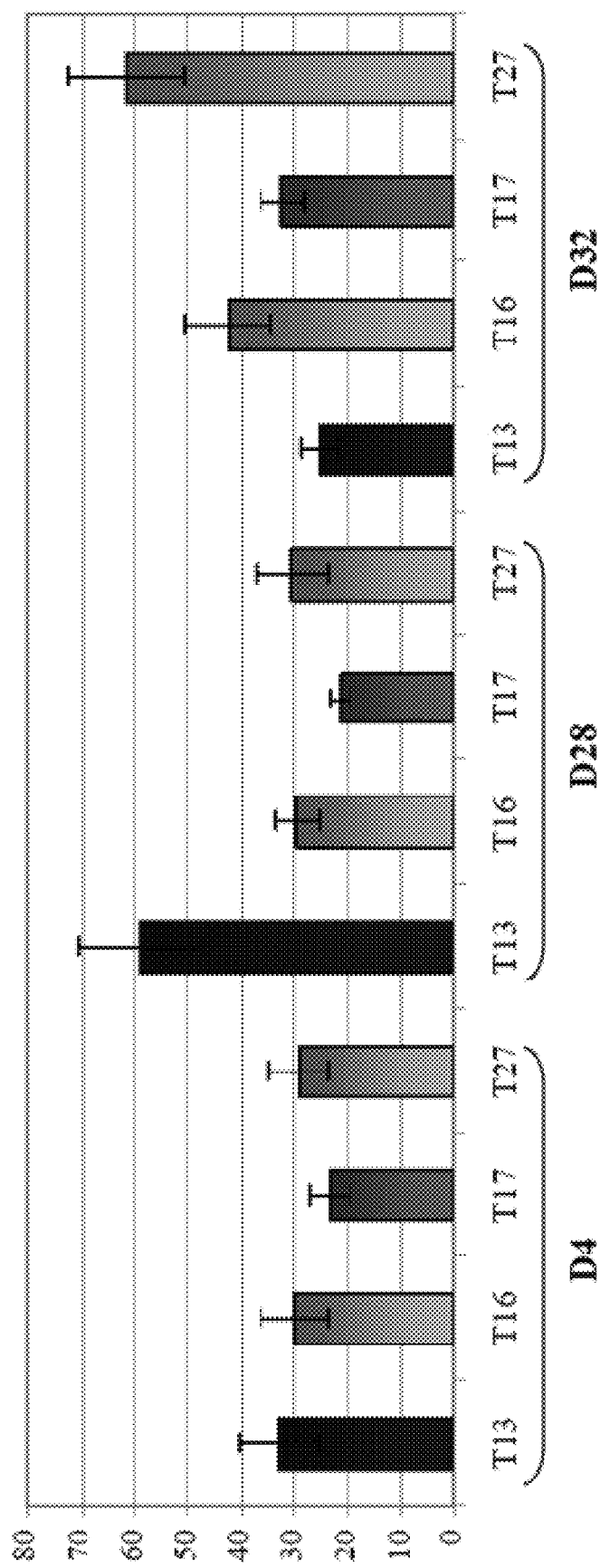
FIG. 27 depicts the frequency of homologous recombination for 12 different target locus/donor locus combinations of the donor and target loci described in the Examples below and in FIG. 26 and crossing with the I-SceI expression plant line Ubi::I-SceI #10. The frequency of homologous recombination was screened in the F1' generation and visualized as blue sectors after histochemical staining. Depicted are the numbers of blue sectors per plant (mean of 30 seedlings per combination, each value is the mean of three independent experiments)

Somatic TE events in the F1' generation of different target/donor combinations were quantified. Indeed, we were able to detect 20 to 60 blue spots or sectors per 7 days old seedling in contrast to controls without I-SceI expression where no somatic TE events were found, indicating that TE can be enhanced in planta by orders of magnitude via DSB induction. We also noticed that there are positive effects on the recombination frequencies if the target and the donor constructs are located on the same chromosome (see FIGS. 26 and 27). After demonstrating that in plants GT is possible with this system, we tested whether TE events could be transferred to the germline, too. We choose the line T-13/D-28 as target/donor combination and screened the F2' generation for completely stained plants. In 4 independent experiments we have screened about fifty thousand seeds and obtained over 350 blue seedlings (see Table 2).

This relates to a GT frequency of $6,9 \times 10^{-3}$.

TABLE 2

| Experiment | Total number of seedlings | Blue seedlings | Blue seedlings/total number of seedlings |
|---|---|---|---|
| 1 | $1.3 \times 10^4$ | 114 | 1:112 |
| 2 | $1.3 \times 10^4$ | 93 | 1:136 |
| 3 | $1.2 \times 10^4$ | 67 | 1:184 |
| 4 | $1.3 \times 10^4$ | 80 | 1:157 |

To confirm that TE events detected by histochemical staining are of the expected molecular nature, F3' progeny of TE plants was characterized by Southern blotting. To avoid the standard histochemical staining procedure that is lethal to plants, batches of seeds of respective transgenic line were grown on agar plates, which were stained 7 days postgermination for a short while by covering the agar plates with buffer solution containing the histochemical staining substrate X-Gluc. As soon as roots of some individual seedlings became bluish we transferred the respective plants to new plates and grew them further. To sustain the beta-glucuronidase expression we cut single leaves for the standard histochemical staining procedure to confirm the primary results. By this means 20 individual plants of the F2' generation with abundant GUS activity could be obtained for further molecular analysis by PCR and Southern blotting.

Southern blot analysis confirmed that the detected beta-glucuronidase activity arose due to the HR-mediated restoration of the GUS gene in the target locus. To further sustain our results we PCR amplified the recombined GUS fragment out of all 20 lines. Sequence analysis revealed the presence of the restored GUS sequence without any mutation, demonstrating that the gene was indeed restored by homologous recombination.

It has been shown before that homologous recombination often occurs only at one but not the other side of the DSB (Puchta, 1998; Puchta, 2005). Therefore, Southern analysis was also applied for the other end, which was not selected for HR-mediated repair by marker gene restoration. Indeed, in all 6 lines in the figure this GT specific fragment could be detected. Moreover, in the same two lines as observed before (GT-2 and GT-3) a fragment indicating the presence of the original donor construct was present, too. All in all, we were able to detect the respective 2,4 kb fragment in 19 of 20 lines. Thus, one-side events occur rarely. To confirm these results on the sequence level, we also performed PCR analysis with the 19 positive lines. Sequence analysis verified that in all 19 lines accurate homologous integration occurred at this end of the break.

It is noteworthy that no fragments of other sizes could be detected in all recombinant lines. This indicates that in all cases the excised donor locus was not integrated elsewhere in the genome by non-homologous end joining (NHEJ).

To test whether the excised kanamycin gene originating from the target transgene was still present in the genome further Southern analysis were performed, using a membrane carrying MfeI digested genomic DNA with a kanamycin-specific probe. However, a signal with the target locus in T-13 control plants could be detected. Thus, in no case the excised resistance cassette was re-integrated in the genome by NHEJ. This is reminiscent to the fact that we also could not detect randomly integrated copies of the excised donor locus in any recombinant line. To test whether the break in the donor construct was repaired by NHEJ or single strand annealing (SSA) following excision of the donor locus we amplified the fragment out of the lines that still harboured the repaired donor locus T-DNA. In all lines tested we found that the break was repaired by the use of homology, thus by SSA.

To test if the restored GUS reporter gene is inherited like an endogenous locus the segregation of the restored beta-glucuronidase ORF in the F3' generation was checked. In all cases tested, a Mendelian segregation pattern of the gene was detected.

Davis, A. M., A. Hall, A. J. Millar, C. Darrah und S. J. Davis (2009). "Protocol: Streamlined sub-protocols for floral-dip transformation and selection of transformants in *Arabidopsis thaliana.*" Plant methods 5: 3.

Hartung, F. und H. Puchta (2000). "Molecular characterisation of two paralogous SPO11 homologues in *Arabidopsis thaliana.*" Nucleic Acids Res 28(7): 1548-54.

Kawalleck, P., I. E. Somssich, M. Feldbrugge, K. Hahlbrock und B. Weisshaar (1993). "Polyubiquitin gene expression and structural properties of the ubi4-2 gene in Petroselinum crispum." Plant molecular biology 21(4): 673-84.

O'Malley, R. C., J. M. Alonso, C. J. Kim, T. J. Leisse und J. R. Ecker (2007). "An adapter ligation-mediated PCR method for high-throughput mapping of T-DNA inserts in the *Arabidopsis* genome." Nat Protoc 2(11): 2910-7.

Ochman, H., A. S. Gerber und D. L. Hartl (1988). "Genetic applications of an inverse polymerase chain reaction." Genetics 120(3): 621-3.

Orel, N., A. Kyryk und H. Puchta (2003). "Different pathways of homologous recombination are used for the repair of double-strand breaks within tandemly arranged sequences in the plant genome." Plant J 35(5): 604-12.

Pacher, M., W. Schmidt-Puchta und H. Puchta (2007). "Two unlinked double-strand breaks can induce reciprocal exchanges in plant genomes via homologous recombination and nonhomologous end joining." Genetics 175(1): 21-9.

Salomon, S. und H. Puchta (1998). "Capture of genomic and T-DNA sequences during double-strand break repair in somatic plant cells." EMBO J 17(20): 6086-95.

Tan, G., Y. Gao, M. Shi, X. Zhang, S. He, Z. Chen und C. An (2005). "SiteFinding-PCR: a simple and efficient PCR method for chromosome walking." Nucleic Acids Res 33(13): e122.

Triglia, T., M. G. Peterson und D. J. Kemp (1988). "A procedure for in vitro amplification of DNA segments that lie outside the boundaries of known sequences." Nucleic Acids Res 16(16): 8186.

The invention claimed is:

1. A method for modifying at least one target locus in a plant cell, comprising:
 a) providing a plant cell comprising at least one target locus comprising at least one homologous region A and at least one homologous region B and comprising at least one nucleotide sequence Z located between at least one homologous region A and at least one homologous region B and comprising at least one donor locus comprising at least one homologous region C and at least one homologous region D and comprising at least one nucleotide sequence X located between at least one homologous region C and at least one homologous region D, wherein homologous region(s) A and homologous region(s) C have sufficient sequence identity to be able to recombine via homologous recombination and homologous region(s) B and homologous region(s) D have sufficient sequence identity to be able to recombine via homologous recombination, and wherein nucleotide sequence Z has a length of 1 to 50,000 base pairs and nucleotide sequence X has a length of 1 to 50,000 base pairs;

wherein the at least one target locus and the at least one donor locus are integrated in the chromosomal DNA of the plant cell;

wherein the at least one target locus comprises one or more LAGLIDADG endonuclease cutting site(s) located between at least one homologous region A and at least one homologous region B; and wherein the at least one donor locus comprises at least two LAGLIDADG endonuclease cutting sites flanking a nucleotide sequence of the donor locus comprising at least one homologous region C and at least one homologous region D;

b) providing the plant cell of step a) with at least one LAGLIDADG endonuclease being able to nick or cut at least one LAGLIDADG endonuclease cutting site located in the at least one target locus or located in the at least one donor locus or located in the at least one target locus and at least one donor locus;

wherein the at least one LADLIDADG endonuclease is selected from I-SceI, I-CreI, I-MsoI, I-CeuI, I-DmoI, I-AnlI, PI-SceI, and engineered variants thereof;

c) allowing the LAGLIDADG endonuclease to nick or cleave at least two of the LAGLIDADG endonuclease cutting sites of step a), wherein the at least two LAGLIDADG endonuclease cutting sites flanking the nucleotide sequence of the donor locus are nicked or cleaved; and d) allowing homologous region A and homologous region C of step a) to recombine and allowing homologous region B and homologous region D of step a) to recombine.

2. A method for modifying at least one target locus in a plant cell, comprising:

a) providing a plant cell comprising at least one target locus integrated in the chromosomal DNA of the plant cell wherein the at least one target locus comprises at least one homologous region A and at least one homologous region B and comprising at least one nucleotide sequence Z located between at least one homologous region A and at least one homologous region B and wherein nucleotide sequence Z is flanked by at least one LAGLIDADG endonuclease cutting site on each side of nucleotide sequence Z;

b) providing the plant cell of step a) with at least one donor locus comprising at least one homologous region C and at least one homologous region D and comprising at least one nucleotide sequence X located between at least one homologous region C and at least one homologous region D, wherein homologous region(s) A and homologous region(s) C have sufficient sequence identity to be able to recombine via homologous recombination and homologous region(s) B and homologous region(s) D have sufficient sequence identity to be able to recombine via homologous recombination and wherein the at least one donor locus comprises at least two LAGLIDADG endonuclease cutting sites flanking a nucleotide sequence of the donor locus comprising at least one homologous region C and at least one homologous region D;

c) providing the plant cell of step a) or step b) with at least one LAGLIDADG endonuclease being able to nick or cut at least one LAGLIDADG endonuclease cutting site located in the at least one target locus or located in the at least one donor locus or located in the at least one target locus and at least one donor locus;

wherein the at least one LADLIDADG endonuclease is selected from I-SceI, I-CreI, I-MsoI, I-CeuI, I-DmoI, I-AnlI, PI-SceI, and engineered variants thereof;

d) allowing the LAGLIDADG endonuclease to nick or cleave at least one of the LAGLIDADG endonuclease cutting sites of step a) and step b); and e) allowing homologous region A and homologous region C of step a) and step b) to recombine and allowing homologous region B and homologous region D of step a) and step b) to recombine.

3. The method of claim 1, wherein the at least one LAGLIDADG endonuclease of step b) is provided by:

a) crossing or fusion with another plant cell comprising at least one expression cassette being able to express at least one LAGLIDADG endonuclease in the plant cell of step a) of claim 1 or a progeny cell thereof;

b) stable or transient transformation with at least one expression cassette being able to express at least LAGLIDADG endonuclease in the in the plant cell of step a) or a progeny cell thereof;

c) infection with a viral vector comprising at least one expression cassette being able to express at least one LAGLIDADG endonuclease in the plant cell of step a) or a progeny cell thereof;

d) inducing expression of at least one LAGLIDADG endonuclease in the plant cell of step a) of claim 1 or a progeny cell thereof;

e) introducing of m-RNA coding for at least one LAGLIDADG endonuclease in the plant cell of step a) of claim 1 or a progeny cell thereof; or f) introducing at least one LAGLIDADG endonuclease via particle bombardment or bacterial SecIII or SecIV secretion systems, or peptide mediated cell-membrane transfer in the plant cell of step a) or a progeny cell thereof.

4. The method of claim 1, wherein at least two LAGLIDADG endonucleases are provided in step b), wherein one LAGLIDADG endonuclease is able to nick or cut at least one LAGLIDADG endonuclease cutting site of the at least one target locus and the other LAGLIDADG endonuclease is able to nick or cut at least one LAGLIDADG endonuclease cutting site of the at least one donor locus, and wherein the at least two LADLIDADG endonucleases are independently selected from I-SceI, I-CreI, I-MsoI, I-CeuI, I-DmoI, I-AnlI, PI-SceI, and engineered variants thereof.

5. The method of claim 1, wherein a) the target locus is provided together with at least one LAGLIDADG endonuclease being able to cut or nick at least one LAGLIDADG endonuclease cutting site located in the at least one donor locus, but is not being able to cleave or nick a LAGLIDADG endonuclease cutting site located in the at least one target locus;

b) the donor locus is provided together with at least one LAGLIDADG endonuclease being able to cut or nick at least one LAGLIDADG endonuclease cutting site located in the at least one target locus, but not being able to cut or nick a LAGLIDADG endonuclease cutting site located in the at least one donor locus; or c) a combination of a) and b).

6. The method of claim 1, wherein the LAGLIDADG endonuclease cutting site(s) of at least one target locus and the LAGLIDADG endonuclease cutting sites of the at least one donor locus, can be nicked or cut with a LAGLIDADG endonuclease provided in step b).

7. The method of claim 1, wherein at least one target locus and at least one donor locus are located on homologous chromosomes, or in homologous regions of non-homologous chromosomes.

8. The method of claim 1, wherein at least one target locus or at least one donor locus or wherein at least one target locus and at least one donor locus comprise an expression cassette for the LAGLIDADG endonuclease of step b).

9. The method of claim 1, wherein the at least one donor locus comprises at least one homologous region E and at least one homologous region F, wherein homologous region(s) E and homologous region(s) F have sufficient sequence identity to be able to recombine via homologous recombination and wherein the at least one homologous region E and the at least one homologous region F flank the at least one homologous region C and the at least one homologous region D and
wherein the expression cassette for the LAGLIDADG endonuclease of step b) is located
a) between at least one homologous region A and at least one homologous region B;
b) outside of at least one homologous region A and at least one homologous region B;
c) between at least one homologous region C and at least one homologous region D;
d) between at least one homologous region E and at least one homologous region F, but outside of at least one homologous region C and at least one homologous region D;
e) outside of at least one homologous region E and at least one homologous region F; or
f) neither in a target nor in a donor locus.

10. The method of claim 1, wherein the plant cell comprises:
a) two or more target loci each comprising at least one homologous region A and at least one homologous region B;
b) two or more donor loci each comprising at least one homologous region C and at least one homologous region D; or
c) two or more target loci each comprising at least one homologous region A and at least one homologous region B and two or more donor loci each comprising at least one homologous region C and at least one homologous region D;
wherein homologous region(s) A and homologous region(s) C have sufficient sequence identity to be able to recombine via homologous recombination and homologous region(s) B and homologous region(s) D have sufficient sequence identity to be able to recombine via homologous recombination.

11. The method of claim 1, wherein the plant cell is homozygous for at least one target locus or is homozygous for at least one donor locus or is homozygous for at least one target locus and is homozygous for at least one donor locus.

12. The method of claim 1, wherein the proportion of the target locus to the donor loci or the proportion of the target loci to the donor locus or the proportion of the target loci to the donor loci, is 1:1, 1:2, 1:3, 1:4, 1:5, 1:6, or 6:1, 5:1, 4:1, 3:1, 2:1.

13. The method of claim 1, wherein at least one target locus, at least one donor locus, or at least one target locus and at least one donor locus is: a) a transgenic locus; or b) a naturally occurring locus.

14. The method of claim 1, wherein the at least one target locus and the at least one donor locus of the plant cell of step a) are combined via crossing of a plant comprising the least one target locus with another plant comprising the at least one donor locus.

15. The method of claim 2, wherein the at least one LAGLIDADG endonuclease of step b) is provided by:
a) crossing or fusion with another plant cell comprising at least one expression cassette being able to express at least one LAGLIDADG endonuclease in the plant cell of step a) of claim 1 or a progeny cell thereof;
b) stable or transient transformation with at least one expression cassette being able to express at least LAGLIDADG endonuclease in the in the plant cell of step a) or a progeny cell thereof;
c) infection with a viral vector comprising at least one expression cassette being able to express at least one LAGLIDADG endonuclease in the plant cell of step a) or a progeny cell thereof;
d) inducing expression of at least one LAGLIDADG endonuclease in the plant cell of step a) of claim 1 or a progeny cell thereof;
e) introducing of m-RNA coding for at least one LAGLIDADG endonuclease in the plant cell of step a) of claim 1 or a progeny cell thereof; or
f) introducing at least one LAGLIDADG endonuclease via particle bombardment or bacterial SecIII or SecIV secretion systems, or peptide mediated cell-membrane transfer in the plant cell of step a) or a progeny cell thereof.

16. The method of claim 2, wherein at least two LAGLIDADG endonucleases are provided in step b), wherein one LAGLIDADG endonuclease is able to nick or cut at least one LAGLIDADG endonuclease cutting site of the at least one target locus and the other LAGLIDADG endonuclease is able to nick or cut at least one LAGLIDADG endonuclease cutting site of the at least one donor locus, and wherein the at least two LADLIDADG endonucleases are independently selected from I-SceI, I-CreI, I-MsoI, I-CeuI, I-DmoI, I-AnII, PI-SceI, and engineered variants thereof.

17. The method of claim 2, wherein
a) the target locus is provided together with at least one LAGLIDADG endonuclease being able to cut or nick at least one LAGLIDADG endonuclease cutting site located in the at least one donor locus, but is not being able to cleave or nick a LAGLIDADG endonuclease cutting site located in the at least one target locus;
b) the donor locus is provided together with at least one LAGLIDADG endonuclease being able to cut or nick at least one LAGLIDADG endonuclease cutting site located in the at least one target locus, but not being able to cut or nick a LAGLIDADG endonuclease cutting site located in the at least one donor locus; or
c) a combination of a) and b).

18. The method of claim 2, wherein the LAGLIDADG endonuclease cutting site(s) of at least one target locus and the LAGLIDADG endonuclease cutting sites of the at least one donor locus, can be nicked or cut with a LAGLIDADG endonuclease provided in step b).

19. The method of claim 2, wherein at least one target locus and at least one donor locus are located on homologous chromosomes, or in homologous regions of non-homologous chromosomes.

20. The method of claim 2, wherein at least one target locus or at least one donor locus or wherein at least one target locus and at least one donor locus comprise an expression cassette for the LAGLIDADG endonuclease of step b).

21. The method of claim 2, wherein the at least one donor locus comprises at least one homologous region E and at least one homologous region F, wherein homologous region(s) E and homologous region(s) F have sufficient sequence identity to be able to recombine via homologous recombination and wherein the at least one homologous region E and the at least one homologous region F flank the at least one homologous region C and the at least one homologous region D and
   wherein the expression cassette for the LAGLIDADG endonuclease of step b) is located
   a) between at least one homologous region A and at least one homologous region B;
   b) outside of at least one homologous region A and at least one homologous region B;
   c) between at least one homologous region C and at least one homologous region D;
   d) between at least one homologous region E and at least one homologous region F, but outside of at least one homologous region C and at least one homologous region D;
   e) outside of at least one homologous region E and at least one homologous region F; or
   f) neither in a target nor in a donor locus.

22. The method of claim 2, wherein the plant cell comprises:
   a) two or more target loci each comprising at least one homologous region A and at least one homologous region B;
   b) two or more donor loci each comprising at least one homologous region C and at least one homologous region D; or
   c) two or more target loci each comprising at least one homologous region A and at least one homologous region B and two or more donor loci each comprising at least one homologous region C and at least one homologous region D;
   wherein homologous region(s) A and homologous region(s) C have sufficient sequence identity to be able to recombine via homologous recombination and homologous region(s) B and homologous region(s) D have sufficient sequence identity to be able to recombine via homologous recombination.

23. The method of claim 2, wherein the at least one target locus and the at least one donor locus of the plant cell of step a) are combined via crossing of a plant comprising the least one target locus with another plant comprising the at least one donor locus.

* * * * *